United States Patent
Tojo et al.

(10) Patent No.: US 6,262,210 B1
(45) Date of Patent: Jul. 17, 2001

(54) PROCESS FOR PRODUCING AROMATIC CARBONATES

(75) Inventors: Masahiro Tojo; Kazuhiro Oonishi; Kyosuke Komiya, all of Kurashiki (JP)

(73) Assignee: Asahi Kasei Kogyo Kabushiki Kaisha, Osaka (JP)

( * ) Notice: Subject to any disclaimer, the term of this patent is extended or adjusted under 35 U.S.C. 154(b) by 0 days.

(21) Appl. No.: 09/445,982
(22) PCT Filed: Sep. 16, 1998
(86) PCT No.: PCT/JP98/04152
 § 371 Date: Dec. 15, 1999
 § 102(e) Date: Dec. 15, 1999
(87) PCT Pub. No.: WO99/14183
 PCT Pub. Date: Mar. 25, 1999

(30) Foreign Application Priority Data

Sep. 16, 1997 (JP) .................................. 9-250575

(51) Int. Cl.$^7$ .................................. C08F 124/00
(52) U.S. Cl. .................. 526/270; 528/196; 528/198
(58) Field of Search ............... 526/270; 528/196, 528/198

(56) References Cited

U.S. PATENT DOCUMENTS

| 5,210,268 | 5/1993 | Fukuoka et al. ............... 558/270 |
| 5,380,908 | 1/1995 | Murata et al. ................. 558/270 |

FOREIGN PATENT DOCUMENTS

| 0855384A1 | 7/1998 | (EP) . |
| 1172852 | 8/1986 | (JP) . |
| 9169704 | 6/1987 | (JP) . |
| 4211038 | 8/1992 | (JP) . |
| 6157410 | 6/1994 | (JP) . |
| WO9711049 | 3/1997 | (WO) . |

Primary Examiner—Terressa M. Boykin
(74) Attorney, Agent, or Firm—Birch, Stewart, Kolasch & Birch, LLP

(57) ABSTRACT

A process for producing aromatic carbonates, which comprises transesterifying, in the presence of a metal-containing catalyst, a starting material selected from a dialkyl carbonate, an alkyl aryl carbonate and a mixture thereof with a reactant selected from an aromatic monohydroxy compound, an alkyl aryl carbonate and a mixture thereof, characterized in that: at least one type of catalyst-containing liquid is taken out, wherein the catalyst-containing liquid is selected from a portion of a high boiling point reaction mixture obtained by the above transesterification and containing the desired aromatic carbonate and the metal-containing catalyst, and a portion of a liquid catalyst fraction obtained by separating the desired aromatic carbonate from the high boiling point reaction mixture, wherein each portion contains (A) high boiling point substance having a boiling point higher than the boiling point of the produced aromatic carbonate and (B) the metal-containing catalyst; (C) a functional substance capable of reacting with at least one component selected from high boiling point substance (A) and metal-containing catalyst (B) is added to the taken-out catalyst-containing liquid; and the (B)/(C) reaction product is recycled to the reaction system, while withdrawing the (A)/(C) reaction product. By the process of the present invention, the desired aromatic carbonates having high purity can be produced stably for a prolonged period of time.

12 Claims, 5 Drawing Sheets

PROCESS FOR PRODUCING AROMATIC CARBONATES

This application is the national phase under 35 U.S.C. § 371 of PCT International Application No. PCT/JP98/04152 which has an international filing date of Sep. 16, 1998, which designated the United States of America.

BACKGROUND OF THE INVENTION

1. Field of The Invention

The present invention relates to a process for producing aromatic carbonates. More particularly, the present invention is concerned with a process for producing aromatic carbonates, which comprises transesterifying, in the presence of a metal-containing catalyst, a starting material selected from the group consisting of a dialkyl carbonate, an alkyl aryl carbonate and a mixture thereof with a reactant selected from the group consisting of an aromatic monohydroxy compound, an alkyl aryl carbonate and a mixture thereof, characterized in that:

- at least one type of catalyst-containing liquid is taken out,
- the catalyst-containing liquid being selected from the group consisting of:
  - a portion of a high boiling point reaction mixture obtained by the above transesterification and containing the desired aromatic carbonate and the metal-containing catalyst, and
  - a portion of a liquid catalyst fraction obtained by separating the desired aromatic carbonate from the high boiling point reaction mixture,
- each portion containing (A) high boiling point substance having a boiling point higher than the boiling point of the produced aromatic carbonate and containing (B) the metal-containing catalyst;
- (C) a functional substance capable of reacting with at least one component selected from the group consisting of the high boiling point substance (A) and the metal-containing catalyst (B) is added to the taken-out catalyst-containing liquid, to thereby obtain at least one reaction product selected from the group consisting of an (A)/(C) reaction product and a (B)/(C) reaction product; and
- the (B)/(C) reaction product is recycled to the reaction system, while withdrawing the (A)/(C) reaction product.

According to the process of the present invention, disadvantageous phenomena, such as the accumulation of the high boiling point substance (A) in the reaction system which causes the discoloration of an ultimate aromatic polycarbonate (which is produced from an aromatic carbonate), can be prevented without withdrawing the catalyst from the reaction system so that the desired aromatic carbonates having high purity can be produced stably for a prolonged period of time.

2. Prior Art

An aromatic carbonate is useful as a raw material for, e.g., the production of an aromatic polycarbonate (whose utility as engineering plastics has been increasing in recent years) without using poisonous phosgene. With respect to the method for the production of an aromatic carbonate, a method for producing an aromatic carbonate or an aromatic carbonate mixture is known, in which a dialkyl carbonate, an alkyl aryl carbonate or a mixture thereof is used as a starting material and an aromatic monohydroxy compound, an alkyl aryl carbonate or a mixture thereof is used as a reactant, and in which a transesterification reaction is performed between the starting material and the reactant.

However, since this type of transesterification is a reversible reaction in which, moreover, not only is the equilibrium biased toward the original system but the reaction rate is also low, the production of an aromatic carbonate by the above-mentioned method on an industrial scale is accompanied with great difficulties.

To improve the above-mentioned method, several proposals have been made, most of which relate to the development of a catalyst for increasing the reaction rate. As a catalyst for use in the method for producing an alkyl aryl carbonate, a diaryl carbonate or a mixture thereof by reacting a dialkyl carbonate with an aromatic hydroxy compound, there have been proposed various metal-containing catalysts, which include for example, a Lewis acid, such as a transition metal halide, or compounds capable of forming a Lewis acid, [see Unexamined Japanese Patent Application Laid-Open Specification No. 51-105032, Unexamined Japanese Patent Application Laid-Open Specification No. 56-123948 and Unexamined Japanese Patent Application Laid-Open Specification No. 56-123949 (corresponding to West German Patent Application Publication No. 2528412, British Patent No. 1499530 and U.S. Pat. No. 4,182,726)], a tin compound, such as an organotin alkoxide or an organotin oxide [Unexamined Japanese Patent Application Laid-Open Specification No. 54-48733 (corresponding to West German Patent Application Publication No. 2736062), Unexamined Japanese Patent Application Laid-Open Specification No. 54-63023, Unexamined Japanese Patent Application Laid-Open Specification No. 60-169444 (corresponding to U.S. Pat. No. 4,554,110 and West German Patent Application Publication No. 3445552), Unexamined Japanese Patent Application Laid-Open Specification No. 60-169445 (corresponding to U.S. Pat. No. 4,552,704 and West German Patent Application Publication No. 3445555), Unexamined Japanese Patent Application Laid-Open Specification No. 62-277345, and Unexamined Japanese Patent Application Laid-Open Specification No. 1-265063 (corresponding to European Patent Publication No. 338760 and U.S. Pat. No. 5,034,557)], salts and alkoxides of an alkali metal or an alkaline earth metal (Unexamined Japanese Patent Application Laid-Open Specification No. 56-25138), lead compounds (Unexamined Japanese Patent Application Laid-Open Specification No. 57-176932), complexes of a metal, such as copper, iron or zirconium (Unexamined Japanese Patent Application Laid-Open Specification No. 57-183745), titanic acid esters [Unexamined Japanese Patent Application Laid-Open Specification No. 58-185536 (corresponding to U.S. Pat. No. 4,410,464 and West German Patent Application Publication No. 3308921)], a mixture of a Lewis acid and protonic acid [Unexamined Japanese Patent Application Laid-Open Specification No. 60-173016 (corresponding to U.S. Pat. No. 4,609,501 and West German Patent Application Publication No. 3445553)], a compound of Sc, Mo, Mn, Bi, Te or the like [Unexamined Japanese Patent Application Laid-Open Specification No. 1-265064 (corresponding to European Patent Publication No. 0 338 760 A1 and U.S. Pat. No. 5,034,557)], and ferric acetate (Unexamined Japanese Patent Application Laid-Open Specification No. 61-172852).

As a catalyst for use in the method for producing a diaryl carbonate by a same-species intermolecular transesterification, wherein an alkyl aryl carbonate is disproportionated to a dialkyl carbonate and a diaryl carbonate, there have been proposed various catalysts, which include for example, a Lewis acid and a transition metal compound which is capable of forming a Lewis acid [see Unexamined Japanese Patent Application Laid-Open Specification No. 51-75044 (corresponding to West German Patent Application Publication No. 2552907 and U.S. Pat. No. 4,045,464)], a polymeric tin compound [Unexamined Japanese Patent Application Laid-Open Specification No. 60-169444 (corresponding to U.S. Pat. No. 4,554,110 and West German Patent Application Publication No. 3445552)], a compound represented by the formula R—X(=O)OH (wherein X is selected from Sn and Ti, and R is selected from monovalent hydrocarbon residues) [Unexamined Japanese Patent Application Laid-Open Specification No. 60-169445 (corresponding to U.S. Pat. No. 4,552,704 and West German Patent Application Publication No. 3445555)], a mixture of a Lewis acid and protonic acid [Unexamined Japanese Patent Application Laid-Open Specification No. 60-173016 (corresponding to U.S. Pat. No. 4,609,501 and West German Patent Application Publication No. 3445553)], a lead catalyst [Unexamined Japanese Patent Application Laid-Open Specification No. 1-93560 (corresponding to U.S. Pat. No. 5,166,393)], a titanium or zirconium compound (Unexamined Japanese Patent Application Laid-Open Specification No. 1-265062), a tin compound [Unexamined Japanese Patent Application Laid-Open Specification No. 1-265063 (corresponding to U.S. Pat. No. 5,034,557 and European Patent Publication No. 0 338 760)], and a compound of Sc, Mo, Mn, Bi, Te or the like [Unexamined Japanese Patent Application Laid-Open Specification No. 1-265064 (corresponding to U.S. Pat. No. 5,034,557 and European Patent Publication No. 0 338 760)].

Another attempt for improving the yield of aromatic carbonates in these reactions consists in biasing the equilibrium toward the product system as much as possible, by modifying the mode of the reaction process. For example, there have been proposed a method in which by-produced methanol is distilled off together with an azeotrope forming agent by azeotropic distillation in the reaction of a dimethyl carbonate with phenol [see Unexamined Japanese Patent Application Laid-Open Specification No. 54-48732 (corresponding to West German Patent Application Publication No. 2736063 and U.S. Pat. No. 4,252,737) and Unexamined Japanese Patent Application Laid-Open Specification No. 61-291545], and a method in which by-produced methanol is removed by adsorbing the same onto a molecular sieve [Unexamined Japanese Patent Application Laid-Open Specification No. 58-185536 (corresponding to U.S. Pat. No. 4,410,464 and West German Patent Application Publication No. 3308921)].

Further, a method is known in which an apparatus comprising a reactor having provided on the top thereof a distillation column is employed in order to separate and distill off alcohols (by-produced in the course of the reaction) from a reaction mixture obtained in the reactor. [With respect to this method, reference can be made to, for example, Unexamined Japanese Patent Application Laid-Open Specification No. 56-123948 (corresponding to U.S. Pat. No. 4,182,726 and West German Patent Application Publication No. 2528412), Unexamined Japanese Patent Application Laid-Open Specification No. 56-25138, Unexamined Japanese Patent Application Laid-Open Specification No. 60-169444 (corresponding to U.S. Pat. No. 4,554,110 and West German Patent Application Publication No. 3445552), Unexamined Japanese Patent Application Laid-Open Specification No. 60-169445 (corresponding to U.S. Pat. No. 4,552,704 and West German Patent Application Publication No. 3445555), Unexamined Japanese Patent Application Laid-Open Specification No. 60-173016 (corresponding to U.S. Pat. No. 4,609,501 and West German Patent Application Publication No. 3445553), Unexamined Japanese Patent Application Laid-Open Specification No. 61-172852, Unexamined Japanese Patent Application Laid-Open Specification No. 61-291545, and Unexamined Japanese Patent Application Laid-Open Specification No. 62-277345.]

As more preferred methods for producing an aromatic carbonate, the present inventors previously developed a method in which a dialkyl carbonate and an aromatic hydroxy compound are continuously fed to a continuous multi-stage distillation column to effect a continuous transesterification reaction in the distillation column, while continuously withdrawing a low boiling point reaction mixture containing a by-produced alcohol from an upper portion of the distillation column by distillation and continuously withdrawing a high boiling point reaction mixture containing a produced alkyl aryl carbonate from a lower portion of the distillation column [see Unexamined Japanese Patent Application Laid-Open Specification No. 3-291257 (corresponding to U.S. Pat. No. 5,210,268 and European Patent Publication No. 0 461 274)], and a method in which an alkyl aryl carbonate is continuously fed to a continuous multi-stage distillation column to effect a continuous transesterification reaction in the distillation column, while continuously withdrawing a low boiling point reaction mixture containing a by-produced dialkyl carbonate by distillation and continuously withdrawing a high boiling point reaction mixture containing a produced diaryl carbonate from a lower portion of the distillation column [see Unexamined Japanese Patent Application Laid-Open Specification No. 4-9358 (corresponding to U.S. Pat. No. 5,210,268 and European Patent Publication No. 0 461 274)]. These methods for the first time realized efficient, continuous production of an aromatic carbonate. Thereafter, various methods for continuously producing an aromatic carbonate have further been developed, based on the above-mentioned methods developed by the present inventors. Examples of these methods include a method in which a catalytic transesterification reaction is performed in a column reactor [see Unexamined Japanese Patent Application Laid-Open Specification No. 6-41022 (corresponding to U.S. Pat. No. 5,362,901 and European Patent Publication No. 0 572 870), Unexamined Japanese Patent Application Laid-Open Specification No. 6-157424 (corresponding to U.S. Pat. No. 5,334,724 and European Patent Publication No. 0 582 931), Unexamined Japanese Patent Application Laid-Open Specification No. 6-184058 (corresponding to U.S. Pat. No. 5,344,954 and European Patent Publication No. 0 582 930)], a method in which use is made of a plurality of reactors which are connected in series [Unexamined Japanese Patent Application Laid-Open Specification No. 6-234707 (corresponding to U.S. Pat. No. 5,463,102 and European Patent Publication No. 0 608 710 A1), and Unexamined Japanese Patent Application Laid-Open Specification No. 6-263694], a method in which a bubble tower reactor is used [Unexamined Japanese Patent Application Laid-Open Specification No. 6-298700 (corresponding to U.S. Pat. No. 5,523,451 and European Patent Publication No. 0 614 877)], and a method in which a vertically long reactor vessel is used (Unexamined Japanese Patent Application Laid-Open Specification No. 6-345697).

Also, there have been proposed methods for producing an aromatic carbonate stably for a prolonged period of time on a commercial scale. For example, Unexamined Japanese Patent Application Laid-Open Specification No. 6-157410 (corresponding to U.S. Pat. No. 5,380,908 and European Patent Publication No. 0 591 923 A1) discloses a method for producing aromatic carbonates from a dialkyl carbonate and an aromatic hydroxy compound, which comprises continuously supplying a mixture of raw materials and a catalyst to a reactor provided with a distillation column thereon to effect a transesterification reaction in the reactor, while continuously withdrawing a by-produced aliphatic alcohol from the reactor through the distillation column by distillation so as to keep the aliphatic alcohol concentration of the reaction system at 2% by weight or less. This prior art document describes that, by this method, continuous production of an aromatic carbonate can be performed in a stable manner. The object of this method is to avoid the deposition of the catalyst in the distillation column. Further, Patent Application prior-to-examination Publication (Kohyo) No. 9-11049 (corresponding to WO 97/11049) discloses a process for producing an aromatic carbonate, in which the transesterification is conducted while maintaining a weight ratio of an aromatic polyhydroxy compound and/or a residue thereof to the metal component of the metal-containing catalyst at 2.0 or less, with respect to a catalyst-containing liquid-phase mixture in a system for the transesterification, so that the desired aromatic carbonates can be produced stably for a prolonged period of time without suffering disadvantageous phenomena, such as the deposition of the catalyst.

On the other hand, it is known that when an aromatic carbonate is produced by transesterification, high boiling point substances are likely to be by-produced. For example, Unexamined Japanese Patent Application Laid-Open Specification No. 61-172852 discloses that when diphenyl carbonate is produced by a transesterification of dimethyl carbonate with phenol, an impurity having a boiling point equal to or higher than the boiling point of the produced diphenyl carbonate is by-produced, and that the impurity is caused to enter the diphenyl carbonate and causes the discoloration of an ultimate product, such as an aromatic polycarbonate. This prior art document does not dis-close an example of the impurity having a boiling point equal to or higher than the boiling point of the produced diphenyl carbonate; however, as an example of the impurity, there can be mentioned an aryloxycarbonyl-(hydroxy)-arene which is produced as an isomer of a diaryl carbonate by Fries rearrangement. More specifically, when diphenyl carbonate is produced as the diaryl carbonate, a phenyl salicylate can be mentioned as an example of the aryloxycarbonyl-(hydroxy)-arene. Phenyl salicylate is a high boiling point substance whose boiling point is 4 to 5° C. higher than the boiling point of the diphenyl carbonate.

In this case, when the transesterification is conducted for a long period of time, the above-mentioned high boiling point substance accumulates in the reaction system and the amount of the impurity mixed into the ultimate aromatic carbonate tends to increase, so that the purity of the ultimate aromatic carbonate is lowered. Further, as the amount of the high boiling point substance in the reaction mixture increases, the boiling point of the reaction mixture rises, so that the by-production of the high boiling point substance is accelerated, thus rendering it difficult to produce desired aromatic carbonates stably for a prolonged period of time. As a measure for solving the problems, it is conceivable to withdraw a high boiling point substance-containing reaction mixture from the reaction system, thereby preventing the accumulation of the high boiling point substance in the reaction system. However, by this measure, a disadvantage is brought about in that, when a catalyst which is soluble in the reaction liquid is used, both the catalyst and the high boiling point substance are present in a state dissolved in the reaction mixture, so that, for separating the catalyst from the high boiling point substance by a conventional distillation method, it is necessary to heat the reaction mixture at high temperatures, leading to a further increased formation of by-products. Therefore, it is difficult to separate the catalyst from the high boiling point substance. This means that the withdrawal of the high boiling point substance from the reaction system is inevitably accompanied by the discharge of the catalyst. Accordingly, for continuing the reaction, it is necessary to supply a fresh catalyst to the reaction system. As a result, a large quantity of the catalyst is needed.

SUMMARY OF THE INVENTION

In this situation, for solving the above-mentioned problems accompanying the prior art, the present inventors have made extensive and intensive studies. As a result, it has been found that:

in a process for producing aromatic carbonates which comprises transesterifying, in the presence of a metal-containing catalyst, a starting material selected from the group consisting of a dialkyl carbonate, an alkyl aryl carbonate and a mixture thereof with a reactant selected from the group consisting of an aromatic monohydroxy compound, an alkyl aryl carbonate and a mixture thereof, when use is made of a process characterized in that:

at least one type of catalyst-containing liquid is taken out, the catalyst-containing liquid being selected from the group consisting of a portion of a high boiling point reaction mixture obtained by the above transesterification and containing the desired aromatic carbonate and a metal-containing catalyst, and a portion of a liquid catalyst fraction obtained by separating the desired aromatic carbonate from the high boiling point reaction mixture, wherein each portion containing high boiling point substance (A) having a boiling point higher than the boiling point of the produced aromatic carbonate and containing the metal-containing catalyst (B);

a functional substance (C) capable of reacting with at least one component selected from the group consisting of the high boiling point substance (A) and the metal-containing catalyst (B) is added to the taken-out catalyst-containing liquid, to thereby obtain at least one reaction product selected from the group consisting of an reaction product (A)/(C) and a reaction product (B)/(C); and the reaction product (B)/(C) is recycled to the reaction system directly or indirectly, while withdrawing the high boiling point substance without withdrawing the catalyst from the reaction system, disadvantageous phenomena, such as the accumulation of the high boiling point substance (A) in the reaction system which causes the discoloration of an ultimate aromatic polycarbonate (which is produced from an aromatic carbonate), can be prevented, so that a high purity aromatic carbonate can be stably produced for a prolonged period of time. The present invention has been completed, based on the above finding.

Accordingly, it is a primary object of the present invention to provide an improved process for producing an aromatic carbonate, which comprises transesterifying, in the presence of a metal-containing catalyst, a starting material selected from the group consisting of a dialkyl carbonate, an alkyl aryl carbonate and a mixture thereof with a reactant selected from the group consisting of an aromatic monohydroxy compound, an alkyl aryl carbonate and a mixture thereof, wherein the desired high purity aromatic carbonates can be produced stably for a prolonged period of time without suffering above-mentioned disadvantageous phenomena.

That is, according to the process of the present invention, the high boiling point substance can be selectively discharged from the reaction system, so that the concentration of the high boiling point substance in the reaction system can be maintained at a level below a certain value and hence aromatic carbonates having high purity can be produced. Further, since the catalyst can be recycled, not only can the necessary amount of the catalyst be remarkably reduced, but also the occurrence of a catalyst-containing waste containing a high boiling point substance, which used to occur in the conventional technique for the withdrawal of a high boiling point substance out of the reaction system, can be prevented.

The foregoing and other objects, features and advantages of the present invention will be apparent from the following detailed description and appended claims taken in connection with the accompanying drawings.

DESCRIPTION OF REFERENCE NUMERALS

Figure 1:
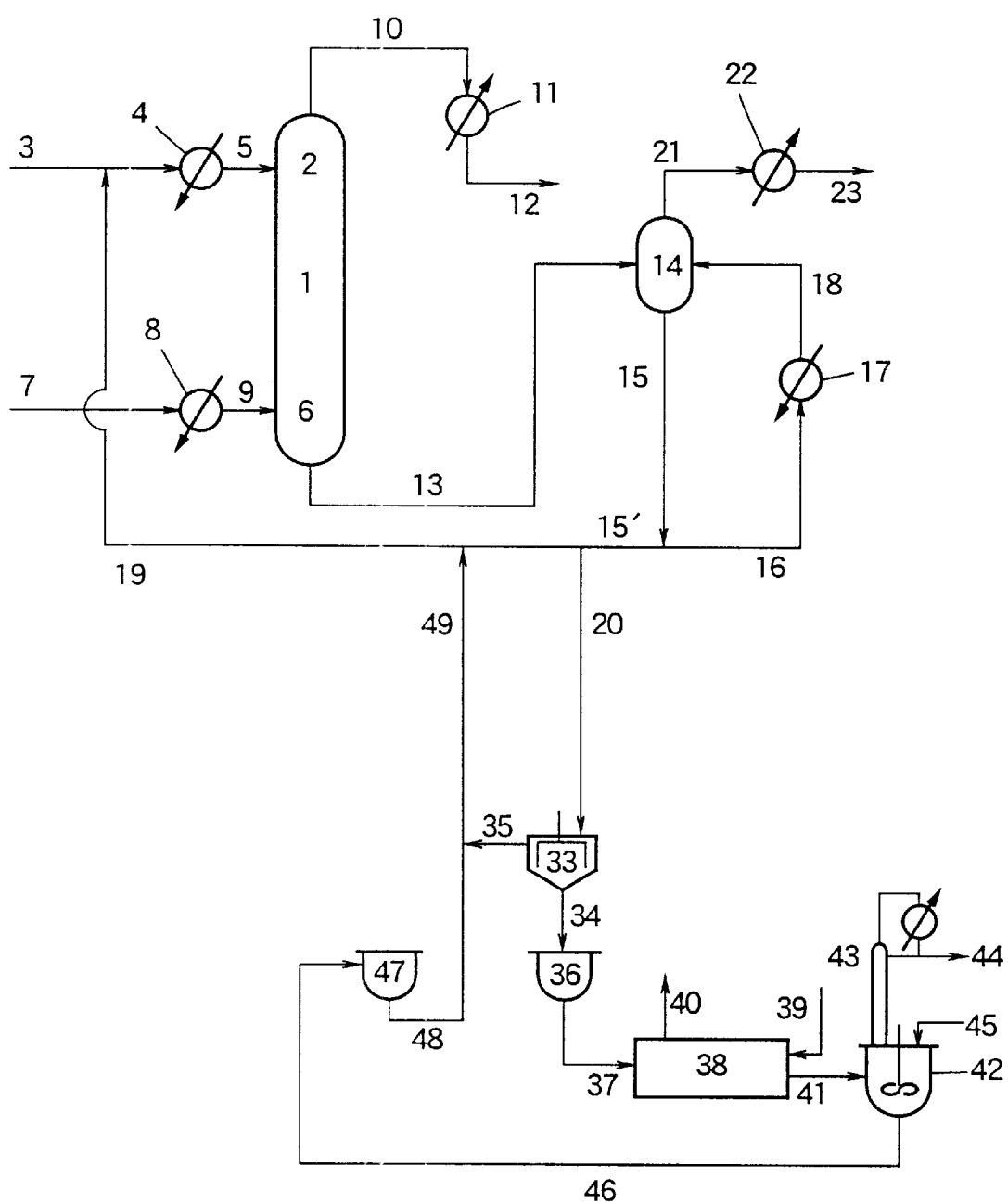
FIG. 1 is a diagram showing an example of systems for practicing the process of the present invention.

1, 101, 201: continuous multi-stage distillation column

2, 102, 202: top of the continuous multi-stage distillation column

3, 5, 7, 9, 10, 12, 13, 15, 15', 16, 18, 19, 20, 20', 21, 23, 25, 27, 28, 29, 30, 32, 34, 35, 37, 39, 40, 41, 44, 45, 46, 48, 48', 49, 51, 53, 55A, 56, 59A, 58, 60, 61, 63, 105, 113, 115, 115', 116, 118, 119, 120, 121, 124, 125, 127, 128, 129, 130, 132, 149, 224, 225, 227, 228, 229, 230, 232, 233, 235: conduit

4: preheater

6, 106, 206: bottom of the continuous multi-stage distillation column

8: evaporator

11, 22, 26, 127, 226, 234: condenser

14, 114: evaporator

17, 31, 117, 131: reboiler

24, 43, 54, 62: distillation column

33: thin-film evaporator

36, 47, 59: storage vessel

38: electric furnace

42, 50, 55, 100: reaction vessel

DETAILED DESCRIPTION OF THE INVENTION

In the present invention, there is provided a process for producing aromatic carbonates, which comprises:

(1) transesterifying a starting material selected from the group consisting of a dialkyl carbonate represented by the formula (1)

an alkyl aryl carbonate represented by the formula (2)

and a mixture thereof with a reactant selected from the group consisting of an aromatic monohydroxy compound represented by the formula (3)

an alkyl aryl carbonate represented by the formula (4)

and a mixture thereof,
wherein each of $R^1$, $R^2$ and $R^3$ independently represents an alkyl group having 1 to 10 carbon atoms, an alicyclic group having 3 to 10 carbon atoms or an aralkyl group having 6 to 10 carbon atoms, and each of $Ar^1$, $Ar^2$ and $Ar^3$ independently represents an aromatic group having 5 to 30 carbon atoms, in the presence of a metal-containing catalyst which is soluble in a reaction system comprising the starting material and the reactant and which is present in a state dissolved in the reaction system, to thereby obtain a high boiling point reaction mixture comprising the metal-containing catalyst and at least one aromatic carbonate which is produced by the transesterification and which corresponds to the starting material and the reactant and is selected from the group consisting of an alkyl aryl carbonate represented by the formula (5)

and a diaryl carbonate represented by the formula (6)

wherein R and Ar are, respectively, selected from the group consisting of $R^1$, $R^2$ and $R^3$ and selected from the group consisting of $Ar^1$, $Ar^2$ and $Ar^3$ in correspondence to the starting material and the reactant, while withdrawing a low boiling point reaction mixture which contains a low boiling point by-product comprising an aliphatic alcohol, a dialkyl carbonate or a mixture thereof corresponding to the starting material and the reactant and represented by at least one formula selected from the group consisting of ROH and

wherein R is as defined above, (2) separating the high boiling point reaction mixture into a product fraction comprising the produced aromatic carbonate and a liquid catalyst fraction comprising the metal-containing catalyst, and (3) recycling the liquid catalyst fraction to the reaction system while withdrawing the product fraction, characterized in that the process further comprises:

(1') taking out at least one type of catalyst-containing liquid which is selected from the group consisting of:
a portion of the high boiling point reaction mixture before the separation of the high boiling point reaction mixture into the product fraction and the liquid catalyst fraction, and
a portion of the separated liquid catalyst fraction, each portion containing (A) at least one high boiling point substance having a boiling point higher than the boiling point of the produced aromatic carbonate and containing (B) the metal-containing catalyst, (2') adding to the taken-out catalyst-containing liquid a functional substance (C) capable of reacting with at least one component selected from the group consisting of the component (A) and the component (B), to thereby obtain at least one reaction product selected from the group consisting of an (A)/(C) reaction product and a (B)/(C) reaction product, and (3') recycling the (B)/(C) reaction product to the reaction system directly or indirectly, while withdrawing the (A)/(C) reaction product.

For an easy understanding of the present invention, the essential features and various preferred embodiments of the present invention are enumerated below.

1. A process for producing aromatic carbonates, which comprises:

(1) transesterifying a starting material selected from the group consisting of a dialkyl carbonate represented by the formula (1)

$$R^1OCOR^1, \quad (1)$$

an alkyl aryl carbonate represented by the formula (2)

$$R^2OCOAr^2 \quad (2)$$

and a mixture thereof with a reactant selected from the group consisting of an aromatic monohydroxy compound represented by the formula (3)

$$Ar^1OH \quad (3),$$

an alkyl aryl carbonate represented by the formula (4)

$$R^3OCOAr^3 \quad (4)$$

and a mixture thereof,
wherein each of $R^1$, $R^2$ and $R^3$ independently represents an alkyl group having 1 to 10 carbon atoms, an alicyclic group having 3 to 10 carbon atoms or an aralkyl group having 6 to 10 carbon atoms, and each of $Ar^1$, $Ar^2$ and $Ar^3$ independently represents an aromatic group having 5 to 30 carbon atoms, in the presence of a metal-containing catalyst which is soluble in a reaction system comprising the starting material and the reactant and which is present in a state dissolved in the reaction system, to thereby obtain a high boiling point reaction mixture comprising the metal-containing catalyst and at least one aromatic carbonate which is produced by the transesterification and which corresponds to the starting material and the reactant and is selected from the group consisting of an alkyl aryl carbonate represented by the formula (5)

$$ROCOAr \quad (5)$$

and a diaryl carbonate represented by the formula (6)

$$ArOCOAr \quad (6)$$

wherein R and Ar are, respectively, selected from the group consisting of $R^1$, $R^2$ and $R^3$ and selected from the group consisting of $Ar^1$, $Ar^2$ and $Ar^3$ in correspondence to the starting material and the reactant, while withdrawing a low boiling point reaction mixture which contains a low boiling point by-product comprising an aliphatic alcohol, a dialkyl carbonate or a mixture thereof corresponding to the starting material and the reactant and represented by at least one formula selected from the group consisting of ROH and

wherein R is as defined above, (2) separating the high boiling point reaction mixture into a product fraction comprising the produced aromatic carbonate and a liquid catalyst fraction comprising the metal-containing catalyst, and (3) recycling the liquid catalyst fraction to the reaction system while withdrawing the product fraction, characterized in that the process further comprises:

(1') taking out at least one type of catalyst-containing liquid which is selected from the group consisting of:
a portion of the high boiling point reaction mixture before the separation of the high boiling point reaction mixture into the product fraction and the liquid catalyst fraction, and a portion of the separated liquid catalyst fraction, each portion containing (A) at least one high boiling point substance having a boiling point higher than the boiling point of the produced aromatic carbonate and containing (B) the metal-containing catalyst, (2') adding to the taken-out catalyst-containing liquid a functional substance (C) capable of reacting with at least one component selected from the group consisting of the component (A) and the component (B), to thereby obtain at least one reaction product selected from the group consisting of an (A)/(C) reaction product and a (B)/(C) reaction product, and (3') recycling the (B)/(C) reaction product to the reaction system directly or indirectly, while withdrawing the (A)/(C) reaction product.

2. The process according to item 1 above, wherein the portion of the high boiling point reaction mixture is from 0.01 to 10% by weight, based on the weight of the high boiling point reaction mixture, and wherein the portion of the separated liquid catalyst fraction is from 0.01 to 40% by weight, based on the weight of the separated liquid catalyst fraction.

3. The process according to item 1 or 2 above, wherein the high boiling point substance (A) originates from at least one compound selected from the group consisting of the starting material, the reactant, impurities contained in the starting material and the reactant, and by-products of the transesterification reaction.

4. The process according to item 3 above, wherein the high boiling point substance (A) is at least one substance selected from the group consisting of an aromatic hydroxy compound (7), a compound (8) derived from the compound (7), an aromatic carboxy compound (9), a compound (10) derived from the compound (9), and xanthone, wherein:
compound (7) is represented by the formula (7):

$$Ar^4\text{---}(OH)_m \qquad (7)$$

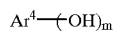

wherein $Ar^4$ represents an aromatic group having a valence of m, m represents an integer of 2 or more, and each —OH group is independently bonded to an arbitrary ring-carbon position of the $Ar^4$ group, compound (8) contains a residue represented by the formula (8):

$$\text{---}(O)_n\text{---}Ar^4\text{---}(OH)_{m-n} \qquad (8)$$

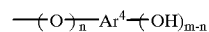

wherein $Ar^4$ and m are as defined for formula (7), n represents an integer of from 1 to m, and each of the —OH group and the —O— group is independently bonded to an arbitrary ring-carbon position of the $Ar^4$ group, compound (9) is represented by the formula (9):

$$(HO)_s\text{---}Ar^5\text{---}(COH)_{r-s} \qquad (9)$$
$$\qquad\qquad\qquad\quad \|$$
$$\qquad\qquad\qquad\quad O$$

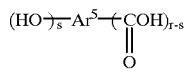

wherein $Ar^5$ represents an aromatic group having a valence of r, r represents an integer of 1 or more, s represents an integer of from 0 to (r−1), and each of the —OH group and the —COOH group is independently bonded to an arbitrary ring-carbon position of the $Ar^5$ group, and compound (10) contains a residue represented by the formula (10):

(10)

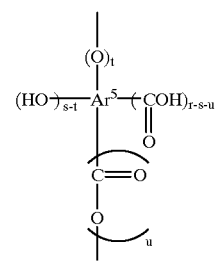

wherein $Ar^5$, r and s are as defined for formula (9), t is an integer of from 0 to s, u is an integer of from 0 to (r−s), with the proviso that t and u are not simultaneously 0, and each of the —OH group, the —COOH group, the —O— group and the —(COO)— group is independently bonded to an arbitrary ring-carbon position of the $Ar^5$ group.

5. The process according to any one of items 1 to 4 above, wherein the functional substance (C) is an oxidizing agent, so that the (A)/(C) reaction product is a low boiling point oxidation product and the (B)/(C) reaction product is a metal oxide.

6. The process according to any one of items 1 to 4 above, wherein the functional substance (C) is a precipitant, so that the (B)/(C) reaction product is a metal-containing substance which precipitates.

7. The process according to item 6 above, wherein the metal-containing substance is a metal compound selected from the group consisting of a metal carbonate, a metal hydroxide, a metal oxide, a metal sulfide and a metal sulfate.

8. The process according to any one of items 1 to 4 above, wherein the functional substance (C) is a reactive solvent, so that the (A)/(C) reaction product is a low boiling point product obtained by the solvolysis of component (A).

9. The process according to item 8 above, wherein the reactive solvent is water, so that the (A)/(C) reaction product is an aromatic monohydroxy compound obtained by the hydrolysis of component (A).

10. The process according to any one of items 1 to 9 above, wherein the steps (1), (2) and (3) are continuously performed, thereby continuously producing an aromatic carbonate.

11. The process according to item 10 above, wherein the starting material and the reactant are continuously fed to a continuous multi-stage distillation column to effect a transesterification reaction therebetween in at least one phase selected from the group consisting of a liquid phase and a gas-liquid phase in the presence of the metal-containing catalyst in the distillation column, while continuously withdrawing a high boiling point reaction mixture containing the produced aromatic carbonate in a liquid form from a lower portion of the distillation column and continuously withdrawing a low boiling point reaction mixture containing the low boiling point by-product in a gaseous form from an upper portion of the distillation column by distillation.

12. A process for producing aromatic polycarbonates, which comprises subjecting to transesterification polymerization an aromatic carbonate produced by the process according to any one of items 1 to 11 above and an aromatic dihydroxy compound.

The process of the present invention for producing an aromatic carbonate from the above-mentioned starting material and reactant by transesterification in the presence of a metal-containing catalyst is characterizd in that:

at least one type of catalyst-containing liquid is taken out, the catalyst-containing liquid being selected from the group consisting of:

a portion of a high boiling point reaction mixture obtained by the above transesterification and containing the desired aromatic carbonate and a metal-containing catalyst, and a portion of a liquid catalyst fraction obtained by separating the desired aromatic carbonate from the high boiling point reaction mixture, each portion containing high boiling point substance (A) having a boiling point higher than the boiling point of the produced aromatic carbonate and containing the metal-containing catalyst (B);

a functional substance (C) capable of reacting with at least one component selected from the group consisting of the high boiling point substance (A) and the metal-containing catalyst (B) is added to the taken-out catalyst-containing liquid, to thereby obtain at least one reaction product selected from the group consisting of an (A)/(C) reaction product and a (B)/(C) reaction product; and the (B)/(C) reaction product is recycled to the reaction system, while withdrawing the (A)/(C) reaction product.

As described above, when the metal-containing catalyst soluble in the reaction system is used, the separation of the high boiling point reaction mixture into the catalyst (B) and the high boiling point substance (A) by the conventional techniques is difficult.

Therefore, the recycling of only the catalyst (B) to the reaction system was conventionally impossible.

In the process of the present invention, by reacting the catalyst-containing liquid containing a high boiling point substance (A) and a metal-containing catalyst (B) with a functional substance (C), an (A)/(C) reaction product and/or a (B)/(C) reaction product can be obtained. The separation between the (A)/(C) reaction product and the (B)/(C) reaction product can be easily performed. Thus, it has for the first time been possible to withdraw the high boiling point substance (A) out of the reaction system, while recycling the catalyst (B) to the reaction system.

The present invention is described below in detail.

The dialkyl carbonate used as a starting material in the present invention is represented by formula (1):

(1)

wherein $R^1$ represents an alkyl group having 1 to 10 carbon atoms, an alicyclic group having 3 to 10 carbon atoms or an aralkyl group having 6 to 10 carbon atoms. Examples of $R^1$ include an alkyl group, such as methyl, ethyl, propyl (isomers), allyl, butyl (isomers), butenyl (isomers), pentyl (isomers), hexyl (isomers), heptyl (isomers), octyl (isomers), nonyl (isomers), decyl (isomers) and cyclohexylmethyl; an alicyclic group, such as cyclopropyl, cyclobutyl, cyclopentyl, cyclohexyl and cycloheptyl; and an aralkyl group, such as benzyl, phenethyl (isomers), phenylpropyl (isomers), phenylbutyl (isomers) and methylbenzyl (isomers). The above-mentioned alkyl group, alicyclic group and aralkyl group may be substituted with a substituent, such as a lower alkyl group, a lower alkoxy group, a cyano group and a halogen atom, as long as the number of carbon atoms of the substituted group does not exceed 10, and may also contain an unsaturated bond.

As a dialkyl carbonate having such $R^1$, there may be mentioned for example, dimethyl carbonate, diethyl carbonate, dipropyl carbonate (isomers), diallyl carbonate, dibutenyl carbonate (isomers), dibutyl carbonate (isomers), dipentyl carbonate (isomers), dihexyl carbonate (isomers), diheptyl carbonate (isomers), dioctyl carbonate (isomers), dinonyl carbonate (isomers), didecyl carbonate (isomers), dicyclopentyl carbonate, dicyclohexyl carbonate, dicycloheptyl carbonate, dibenzyl carbonate, diphenethyl carbonate (isomers), di(phenylpropyl) carbonate (isomers), di(phenylbutyl) carbonate (isomers), di(chlorobenzyl) carbonate (isomers), di(methoxybenzyl) carbonate (isomers), di(methoxymethyl) carbonate, di(methoxyethyl) carbonate (isomers), di(chloroethyl) carbonate (isomers) and di(cyanoethyl) carbonate (isomers). These dialkyl carbonates can also be used in mixture.

Of these dialkyl carbonates, a dialkyl carbonate containing as $R^1$ a lower alkyl group having 4 or less carbon atoms is preferably used. Most preferred is dimethyl carbonate.

The alkyl aryl carbonate used as the starting material in the present invention is represented by the following formula (2):

(2)

wherein $R^2$ may be identical with or different from $R^1$, and represents an alkyl group having 1 to 10 carbon atoms, an alicyclic group having 3 to 10 carbon atoms or an aralkyl group having 6 to 10 carbon atoms; and $Ar^2$ represents an aromatic group having 5 to 30 carbon atoms. As $R^2$, there may be mentioned, for example, the same groups as set forth above for $R^1$.

Illustrative examples of $Ar^2$ in formula (2) include:

a phenyl group and various alkylphenyl groups, such as phenyl, tolyl (isomers), xylyl (isomers), trimethylphenyl (isomers), tetramethylphenyl (isomers), ethylphenyl (isomers), propylphenyl (isomers), butylphenyl (isomers), diethylphenyl (isomers), methylethylphenyl (isomers,), pentylphenyl (isomers), hexylphenyl (isomers) and cyclohexylphenyl (isomers);

various alkoxyphenyl groups, such as methoxyphenyl (isomers), ethoxyphenyl (isomers) and butoxyphenyl (isomers);

various halogenated phenyl groups, such as fluorophenyl (isomers), chlorophenyl (isomers), bromophenyl (isomers), chloromethylphenyl (isomers) and dichlorophenyl (isomers);

various substituted phenyl groups represented by the formula (11):

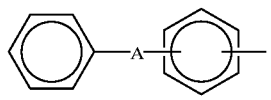

(11)

wherein A represents a single bond, a divalent group, such as —O—, —S—, —CO— or —SO$_2$—, an alkylene group, a substituted alkylene group of the following formula:

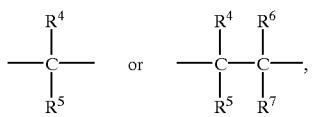

wherein each of $R^4$, $R^5$, $R^6$ and $R^7$ independently represents a hydrogen atom; or a lower alkyl group, a cycloalkyl group, an aryl group or an aralkyl group, which may be substituted with a halogen atom or an alkoxy group, or a cycloalkylene group of the following formula:

wherein k is an integer of from 3 to 11, and the hydrogen atoms may be replaced by a lower alkyl group, an aryl group, a halogen atom or the like, and the aromatic ring in formula (2) may be substituted with a substituent, such as a lower alkyl group, a lower alkoxy group, an ester group, a hydroxyl group, a nitro group, a halogen atom and a cyano group;

a naphthyl group and various substituted naphthyl groups, such as naphthyl (isomers), methylnaphthyl (isomers), dimethylnaphthyl (isomers), chloronaphthyl (isomers), methoxynaphthyl (isomers) and cyanonaphthyl (isomers); and various unsubstituted or substituted heteroaromatic groups, such as pyridyl (isomers), cumaryl (isomers), quinolyl (isomers), methylpyridyl (isomers), chloropyridyl (isomers), methylcumaryl (isomers) and methylquinolyl (isomers).

Representative examples of alkyl aryl carbonate having these $R^2$ and $Ar^2$ include methyl phenyl carbonate, ethyl phenyl carbonate, propyl phenyl carbonate (isomers), allyl phenyl carbonate, butyl phenyl carbonate (isomers), pentyl phenyl carbonate (isomers), hexyl phenyl carbonate (isomers), heptyl phenyl carbonate (isomers), octyl tolyl carbonate (isomers), nonyl ethylphenyl carbonate (isomers), decyl butylphenyl carbonate (isomers), methyl tolyl carbonate (isomers), ethyl tolyl carbonate (isomers), propyl tolyl carbonate (isomers), butyl tolyl carbonate (isomers), allyl tolyl carbonate (isomers), methyl xylyl carbonate (isomers), methyl trimethylphenyl carbonate (isomers), methyl chlorophenyl carbonate (isomers), methyl nitrophenyl carbonate (isomers), methyl methoxyphenyl carbonate (isomers), methyl cumyl carbonate (isomers), methyl naphthyl carbonate (isomers), methyl pyridyl carbonate (isomers), ethyl cumyl carbonate (isomers), methyl benzoylphenyl carbonate (isomers), ethyl xylyl carbonate (isomers), benzyl xylyl carbonate (isomers). These alkyl aryl carbonates can also be used in mixture. Of these alkyl aryl carbonates, one containing as $R^2$ an alkyl group having 1 to 4 carbon atoms and as $Ar^2$ an aromatic group having 6 to 10 carbon atoms is preferably used, and methyl phenyl carbonate is most preferred.

The starting material used in the present invention is selected from the group consisting of a dialkyl carbonate represented by formula (1) above, an alkya aryl carbonate represented by formula (2) above and a mixture thereof.

The aromatic monohydroxy compound used as the reactant in the present invention is represented by formula (3):

$$Ar^1OH \qquad (3)$$

wherein $Ar^1$ may be identical with or different from $Ar^2$, represents an aromatic group having 5 to 30 carbon atoms, and the type of the compound is not limited as long as the hydroxyl group is directly bonded to the aromatic group. As $Ar^1$, there may be mentioned, for example, the same groups as set forth above for $Ar^2$.

Preferred examples of aromatic monohydroxy compounds of formula (3) include phenol; various alkylphenols, such as cresol (isomers), xylenol (isomers), trimethylphenol (isomers), tetramethylphenol (isomers), ethylphenol (isomers), propylphenol (isomers), butylphenol (isomers), diethylphenol (isomers), methylethylphenol (isomers), methylpropylphenol (isomers), dipropylphenol (isomers), methylbutylphenol (isomers), pentylphenol (isomers), hexylphenol (isomers) and cyclohexylphenol (isomers); various alkoxyphenols, such as methoxyphenol (isomers) and ethoxyphenol (isomers); various substituted phenols represented by the following formula (12):

(12)

wherein A is as defined above; naphthol (isomers) and various substituted naphthols; and heteroaromatic monohydroxy compounds, such as hydroxypyridine (isomers), hydroxycumarine (isomers) and hydroxyquinoline (isomers). These aromatic monohydroxy compounds can also be used in mixture.

Of these aromatic monohydroxy compounds, an aromatic monohydroxy compound containing as $Ar^1$ an aromatic group having 6 to 10 carbon atoms is preferably used in the present invention, and phenol is most preferred.

The alkyl aryl carbonate used as the reactant in the present invention is represented by the following formula (4):

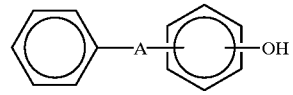

(4)

wherein $R^3$ may be identical with or different from $R^1$ and $R^2{}_7$ and represents an alkyl group having 1 to 10 carbon atoms, as alicyclic group having 3 to 10 carbon atoms or an aralkyl group having 6 to 10 carbon atoms; and $Ar^3$ may be identical with or different from $Ar^1$ and $Ar^2$, and represents an aromatic group having 5 to 30 carbon atoms. As $R^3$, there may be mentioned, for example, the same groups as set forth above for $R^1$. As $Ar^3$, there may be mentioned, for example, the same groups as set forth above for $Ar^2$.

As alkyl aryl carbonates having these $R^3$ and $Ar^3$, there may be mentioned for example, those which are set forth above for alkyl aryl carbonates represented by the above-mentioned formula (2).

Of these alkyl aryl carbonates, one containing as $R^3$ an alkyl group having 1 to 4 carbon atoms and as $Ar^3$ an aromatic group having 6 to 10 carbon atoms is preferably used, and methyl phenyl carbonate is most preferred.

The reactant used in the present invention is selected from the group consisting of a aromatic monohydroxy compound represented by formula (3) above, an alkyl aryl carbonate represented by formula (4) above and a mixture thereof.

The typical reactions, which are involved in the process of the present invention for producing an aromatic carbonate or an aromatic carbonate mixture by transesterifying a starting material with a reactant in the presence of a metal-containing catalyst, are represented by the following formulae (E1), (E2), (E3) and (E4):

(E1)
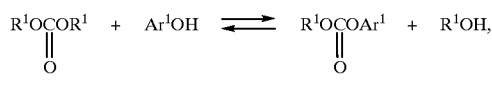

(E2)
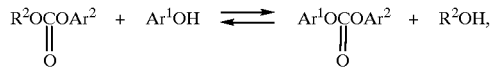

(E3)
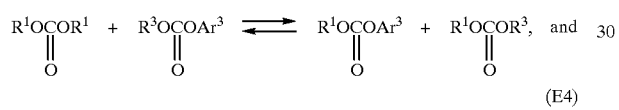

(E4)
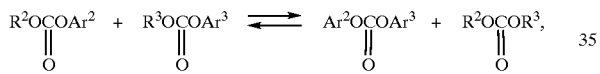

wherein $R^1$, $R^2$, $R^3$, $Ar^1$, $Ar^2$ and $Ar^3$ are as defined above, each of Ar's appearing in formula (E4) independently represents $Ar^2$ or $Ar^3$, and each of R's appearing in formula (E4) independently represents $R^2$ or $R^3$, and wherein when $R^2=R^3$ and $Ar^2=Ar^3$ in formula (E4), the reaction is a same-species intermolecular transesterification reaction generally known as a disproportionation reaction.

When each of the reactions of formulae (E1), (E2), (E3) and (E4) is performed according to the process of the present invention, dialkyl carbonates or alkyl aryl carbonates as the starting materials for the reaction can be used individually or in mixture and aromatic monohydroxy compounds or alkyl aryl carbonates as the reactants for the reaction can be used individually or in mixture.

When $R^2=R^3=R$ and $Ar^2=Ar^3=Ar$ in the transesterification reaction of formula (E4), a diaryl carbonate and a dialkyl carbonate can be obtained by a same-species intermolecular transesterification reaction of a single type of alkyl aryl carbonate. This is a preferred embodiment of the present invention.

Further, when $R^1=R^2=R^3=R$ and $Ar^1=Ar^2=Ar^3=Ar$ in formulae (E1) and (E4), by combining the reaction of formula (E1) with the reaction of formula (E4), a diaryl carbonate can be obtained from a dialkyl carbonate and an aromatic monohydroxy compound through an alkyl aryl carbonate as shown in formulae (E5) and (E6). This is an especially preferred embodiment of the present invention.

(E5)
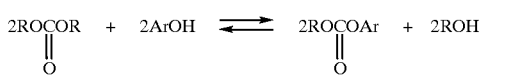

(E6)

Recycling of the dialkyl carbonate by-produced in the reaction of formula (E6) as the starting material for the reaction of formula (E5) results in the formation of 1 mol of a diaryl carbonate and 2 mol of an aliphatic alcohol from 1 mol of a dialkyl carbonate and 2 mol of an aromatic monohydroxy compound.

When $R=CH_3$ and $Ar=C_6H_5$ in the above formulae (E5) and (E6), diphenyl carbonate, which is an important raw material for a polycarbonate and an isocyanate, can be readily obtained from dimethyl carbonate, which is the simplest form of a dialkyl carbonate, and phenol. This is especially important.

The metal-containing catalyst used in the present invention is one capable of promoting the reactions of formulae (E1) to (E4). As such metal-containing catalysts, there may be mentioned for example:

<lead compounds> lead oxides, such as PbO, $PbO_2$ and $Pb_3O_4$; lead sulfides, such as PbS and $Pb_2S$; lead hydroxides, such as $Pb(OH)_2$ and $Pb_2O_2(OH)_2$; plumbites, such as $Na_2PbO_2$, $K_2PbO_2$, $NaHPbO_2$ and $KHPbO_2$; plumbates, such as $Na_2PbO_3$, $Na_2H_2PbO_4$, $K_2PbO_3$, $K_2[Pb(OH)_6]$, $K_4PbO_4$, $Ca_2PbO_4$ and $CaPbO_3$; lead carbonates and basic salts thereof, such as $PbCO_3$ and $2PbCO3.Pb(OH)_2$; lead salts of organic acids, and carbonates and basic salts thereof, such as $Pb(OCOCH_3)_2$, $Pb(OCOCH_3)_4$ and $Pb(OCOCH_3)_2.PbO.3H_2O$; organolead compounds, such as $Bu_4Pb$, $Ph_4Pb$, $Bu_3PbC_1$, $Ph_3PbBr$, $Ph_3Pb$ (or $Ph_6Pb_2$), $Bu_3PbOH$ and $Ph_3PbO$ wherein Bu represents a butyl group and Ph represents a phenyl group; alkoxylead compounds and aryloxylead compounds, such as $Pb(OCH_3)_2$, $(CH_3O)Pb(OPh)$ and $Pb(OPh)_2$; lead alloys, such as Pb—Na, Pb—Ca, Pb—Ba, Pb—Sn and Pb—Sb; lead minerals, such as galena and zinc blende; and hydrates of these lead compounds;

<copper family metal compounds> salts or complexes of copper family metals, such as CuCl, $CuCl_2$, CuBr, $CuBr_2$, CuI, $CuI_2$, $Cu(OAc)_2$, $Cu(acac)_2$, copper oleate, $Bu_2Cu$, $(CH_3O)_2Cu$, $AgNO_3$, AgBr, silver picrate, $AgC_6H_6ClO_4$, $Ag(bullvalene)_3NO_3$, $[AuC\equiv C-C(CH_3)_3]_n$ and $[Cu(C_7H_8)Cl]_4$ wherein Ac represents an acetyl group and acac represents an acetylacetone chelate ligand;

<alkali metal complexes> alkali metal complexes, such as Li(acac) and $LiN(C_4H_9)_2$;

<zinc complexes> zinc complexes, such as $Zn(acac)_2$;

<cadmium complexes> cadmium complexes, such as $Cd(acac)_2$;

<iron family metal compounds> iron family metal complexes, such as $Fe(C_{10}H_8)(CO)_5$, $Fe(CO)_5$, $Fe(C_3H_6)(CO)_3$, $Co(mesitylene)_2(PEt_2Ph)_2$, $CoC_5F_5(CO)_2$, Ni-$\pi$-$C_5H_5NO$ and ferrocene;

<zirconium complexes> zirconium complexes, such as $Zr(acac)_4$ and zirconocene;

<Lewis acids and Lewis acid-forming compounds>

Lewis acids and Lewis acid-forming transition metal compounds, such as $AlX_3$, $TiX_3$, $TiX_4$, $VOX_3$, $VX_5$, $ZnX_2$, $FeX_3$ and $SnX_4$ wherein X represents a halogen atom, an acetoxy group, an alkoxy group or an aryloxy group; and <organotin compounds> organotin compounds, such as $(CH_3)_3SnOCOCH_3$, $(C_2H_5)_3SnOCOC_6H_5$, $Bu_3SnOCOCH_3$, $Ph_3SnOCOCH_3$, $Bu_2Sn(OCOCH_3)_2$, $Bu_2Sn(OCOC_{11}H_{23})_2$, $Ph_3SnOCH_3$, $(C_2H_5)_3SnOPh$, $Bu_2Sn(OCH_3)_2$, $Bu_2Sn(OC_2H_5)_2$, $Bu_2Sn(OPh)_2$, $Ph_2Sn(OCH_3)_2$, $(C_2H_5)_3SnOH$, $Ph_3SnOH$, $Bu_2SnO$, $(C_8H_{17})_2SnO$, $Bu_2SnCl_2$ and $BuSnO(OH)$ wherein Ph represents an phenyl group.

These catalysts are effective even when they are reacted with an organic compound present in the reaction system, such as an aliphatic alcohol, an aromatic monohydroxy compound, an alkyl aryl carbonate, a diaryl carbonate and a dialkyl carbonate. Those which are obtained by heat-treating these catalysts together with a starting material, a reactant and/or a reaction product thereof prior to the use in the process of the present invention can also be used.

It is preferred that the metal-containing catalyst have high solubility in the liquid phase of the reaction system. Preferred examples of metal-containing catalysts include Pb compounds, such as PbO, $Pb(OH)_2$ and $Pb(OPh)_2$; Ti compounds, such as $TiCl_4$ and $Ti(OPh)_4$; Sn compounds, such as $SnCl_4$, $Sn(OPh)_4$, $Bu_2SnO$ and $Bu_2Sn(OPh)_2$; Fe compounds, such as $FeCl_3$, $Fe(OH)_3$ and $Fe(OPh)_3$; and those products which are obtained by treating the above metal compounds with phenol or a liquid phase of the reaction system.

There is no particular limitation with respect to the type of the reactor to be used in the process of the present invention, and various types of conventional reactors, such as a stirred tank reactor, a multi-stage stirred tank reactor and a multi-stage distillation column, can be used. These types of reactors can be used individually or in combination, and may be used either in a batchwise process or a continuous process. From the viewpoint of efficiently biasing the equilibrium toward the product system, a multi-stage distillation column is preferred, and a continuous process using a multi-stage distillation column is especially preferred. There is no particular limitation with respect to the multi-stage distillation column to be used in the present invention as long as it is a distillation column having a theoretical number of stages of distillation of two or more and which can be used for performing continuous distillation. Examples of such multi-stage distillation columns include plate type columns using a tray, such as a bubble-cap tray, a sieve tray, a valve tray and a counterflow tray, and packed type columns packed with various packings, such as a Raschig ring, a Lessing ring, a Pall ring, a Berl saddle, an Intalox saddle, a Dixon packing, a McMahon packing, a Heli pack, a Sulzer packing and Mellapak. In the present invention, any of the columns which are generally used as a multi-stage distillation column can be utilized. Further, a mixed type of plate column and packed column comprising both a plate portion and a portion packed with packings, can also be preferably used.

In one preferred embodiment of the present invention, in which the continuous production of an aromatic carbonate is conducted using a multi-stage distillation column, a starting material and a reactant are continuously fed to a continuous multi-stage distillation column to effect a transesterification reaction there-between in at least one phase selected from a liquid phase and a gas-liquid phase in the presence of a metal-containing catalyst in the distillation column, while continuously withdrawing a high boiling point reaction mixture containing a produced aromatic carbonate or aromatic carbonate mixture in liquid form from a lower portion of the distillation column and continuously withdrawing a low boiling point reaction mixture containing a by-product in gaseous form from an upper portion of the distillation column by distillation.

The amount of the catalyst used in the present invention varies depending on the type thereof, the types and weight ratio of the starting material and the reactant, the reaction conditions, such as reaction temperature and reaction pressure, and the like. Generally, the amount of the catalyst is in the range of from 0.0001 to 30% by weight, based on the total weight of the starting material and the reactant.

The reaction time (or the residence time when the reaction is continuously conducted) for the transesterification reaction in the present invention is not specifically limited, but it is generally in the range of from 0.001 to 50 hours, preferably from 0.01 to 10 hours, more preferably from 0.05 to 5 hours.

The reaction temperature varies depending on the types of the starting material and reactant, but is generally in the range of from 50 to 350° C., preferably from 100 to 280° C. The reaction pressure varies depending on the types of the starting material and reactant and the reaction temperature, and it may be any of a reduced pressure, an atmospheric pressure and a superatmospheric pressure. However, the reaction pressure is generally in the range of from 0.1 to $2.0 \times 10^7$ Pa.

In the present invention, it is not necessary to use a reaction solvent. However, for the purpose of facilitating the reaction operation, an appropriate inert solvent, such as an ether, an aliphatic hydrocarbon, an aromatic hydrocarbon or a halogenated aromatic hydrocarbon, may be used as a reaction solvent.

As mentioned above, the process of the present invention is characterized by taking out the catalyst-containing liquid containing the high boiling point substance (A) and a metal-containing catalyst (B); adding a functional substance (C) capable of reacting with the high boiling point substance (A) and/or the metal-containing catalyst (B) to the taken-out catalyst-containing liquid, to thereby obtain an (A)/(C) reaction product and/or a (B)/(C) reaction product; and recycling the (B)/(C) reaction product directly or indirectly to the reaction system, while withdrawing the (A)/(C) reaction product.

In the process of the present invention, the passage "recycling the (B)/(C) reaction product directly or indirectly to the reaction system" means "recycling the (B)/(C) reaction product to the reactor directly, or recycling the (B)/(C) reaction product to the reactor indirectly through a pipe and a device which communicate with the inlet of the reactor or which are used for recovering the catalyst".

The "catalyst-containing liquid containing the high boiling point substance and a metal-containing catalyst" means at least one type of catalyst-containing liquid which is selected from the group consisting of a portion of the high boiling point reaction mixture before the separation of the high boiling point reaction mixture into the product fraction and the liquid catalyst fraction, and a portion of the separated liquid catalyst fraction. More specifically, the above-mentioned catalyst-containing liquid means, for example, a catalyst-containing liquid which is selected from the group consisting of a portion of the reaction mixture (containing the metal-containing catalyst (B) and the high boiling point substance (A)) which is withdrawn from the reactor, or a portion of a liquid material (having increased concentrations with respect to the catalyst and the high boiling point substance) which is obtained by subjecting to evaporation a part of the catalyst-containing reaction mixture withdrawn from the reactor. In the catalyst-containing liquid, the catalyst may be completely dissolved, or may be in the form of a slurry in which insoluble matters are formed by the reaction between the catalyst and the high boiling point substance. In the present invention, when the catalyst-containing liquid is in the form of a slurry, a portion in the slurry which is present in a non-dissolved state is also included in the "catalyst-containing liquid containing the high boiling point substance (A) and a metal-containing catalyst (B)". The catalyst-containing liquid may be taken out continuously or intermittently.

In the process of the present invention, the "high boiling point substance (A)" means a substance having a boiling point higher than the boiling point of the produced aromatic carbonates, wherein such a substance originates from at least one compound selected from the group consisting of the starting material, the reactant, impurities contained in the starting material and the reactant, and by-products of the transesterification reaction. Examples of such high boiling point substances (A) include an aromatic hydroxy compound, a compound containing a residue of the aromatic hydroxy compound, an aromatic a compound, a compound containing a residue of the aromatic carboxy compound, and xanthone. Those by-products having a high molecular weight which are produced, by reaction, from the aromatic hydroxy compound, a compound containing a residue of the aromatic hydroxy compound, an aromatic carboxy compound, a compound containing a residue of the aromatic carboxy compound, and xanthone can also be mentioned as examples of above-mentioned high boiling point substances (A).

In the present invention, the aromatic hydroxy compound is represented by the following formula (7):

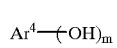 (7)

wherein $Ar^4$ represents an aromatic group having a valence of m, m represents an integer of 2 or more, and each —OH group is individually bonded to an arbitrary ring-carbon position of the $Ar^4$ group.

The residue of the aromatic hydroxy compound is represented by the following formula (8):

 (8)

wherein $Ar^4$ and m are as defined above, n represents an integer of from 1 to m, and each of the —OH group and the —O— group is individually bonded to an arbitrary ring-carbon position of the $Ar^4$ group.

The residue (8) of the aromatic hydroxy compound is present in such a form as chemically bonded to at least one member selected from the group consisting of the metal of the metal-containing catalyst, an alkoxycarbonyl group derived from the dialkyl carbonate or the alkyl aryl carbonate, an aryloxycarbonyl group derived from the alkyl aryl carbonate or the diaryl carbonate, and a carbonyl group derived from the dialkyl carbonate, the alkyl aryl carbonate or the diaryl carbonate.

Illustrative examples of the $Ar^4$ groups in formulae (7) and (8) above include aromatic groups represented by the following formulae (13), (14), (15), (16) and (17):

 (13)

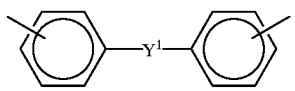 (14)

wherein $Y^1$ represents a single bond, a divalent alkane group having 1 to 30 carbon atoms or a divalent group selected from —O—, —CO—, —S—, —SO$_2$—, —SO— and —COO—,

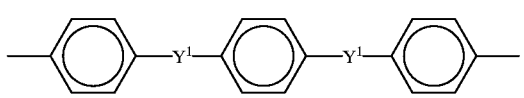 (15)

wherein each of two $Y^1$'s is as defined above, and two $Y^1$'s may be the same or different;

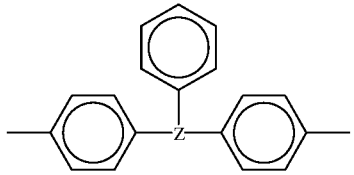 (16)

wherein Z represents a trivalent group, such as a $C_1$–$C_{30}$ trivalent alkane group or a trivalent aromatic group; and at least one hydrogen atom of each aromatic ring may be replaced with a substitutent, such as a halogen atom, a $C_1$–$C_{30}$ alkyl group, a $C_1$–$C_{30}$ alkoxy group, a phenyl group, a phenoxy group, a vinyl group, a cyano group, an ester group, an amido group, a nitro group or the like; and

 (17)

Examples of these aromatic polyhydroxy compounds include hydroquinone, resorcin, catechol, trihydroxybenzene (isomers), bis(hydroxyphenyl)propane (isomers), bis(hydroxyphenyl)methane (isomers), bis(hydroxyphenyl)ether (isomers), bis(hydroxyphenyl)ketone (isomers), bis(hydroxyphenyl)sulfone (isomers), bis(hydroxyphenyl)sulfide (isomers), dihydroxy diphenyl (isomers), bis(dihydroxyphenyl)methane (isomers), 2-hydroxyphenyl hydroxypropyl phenol, dihydroxy (hydroxyphenyl diphenyl) (isomers), tri-(hydroxyphenyl)ethane (isomers), tri-(hydroxyphenyl)benzene (isomers), dihydroxynaphthalene (isomers) and trihydroxynaphthalene (isomers).

Of these aromatic hydroxy compounds and compounds having a residue of the aromatic hydroxy compounds, attention should be made to those compounds which are likely to be present in the system for the transesterification for the production of an aromatic carbonate. As such a compound, there can be mentioned at least one member selected from the group consisting of:

(a) an oxidation product of an aromatic monohydroxy compound as the reactant,
(b) at least one member selected from the group consisting of a product produced by the Fries rearrangement of a diaryl carbonate obtained by the transesterification and oxidation products of the product, and
(c) at least one member selected from the group consisting of aromatic dihydroxy compounds derived from phenol as the reactant and represented by the following formula (18):

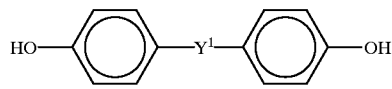
(18)

wherein $Y^1$ is as defined above, and oxidation products of the aromatic dihydroxy compounds.

As examples of oxidation products (a) of an aromatic monohydroxy compound, compounds represented by the following formulae (19) and (20) can be mentioned.

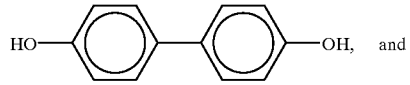
(19)

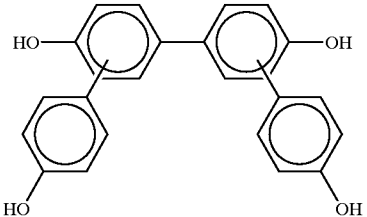
(20)

As examples of products (b) produced by the Fries rearrangement of a diaryl carbonate, compounds represented by the following formulae (21), (22) and (23) can be mentioned.

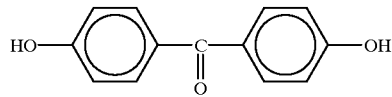
(21)

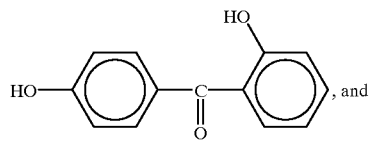
(22)

-continued

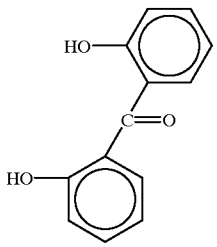
(23)

As examples of oxidation products of the above-mentioned product (b) produced by the Fries rearrangement of a diaryl carbonate and represented by formula (21), compounds represented by the following formulae (24) and (25) can be mentioned. Also, as examples of respective oxidation products of the above-mentioned products (b) represented by formulae (22) and (23), compounds represented by the following formulae (26) and (27) can be mentioned.

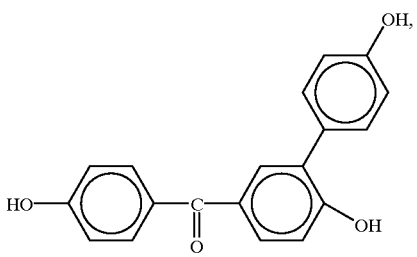
(24)

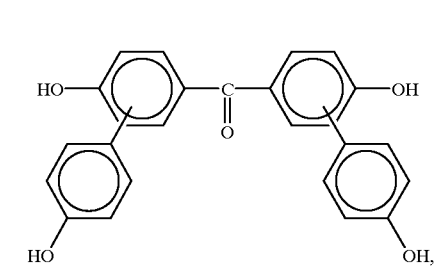
(25)

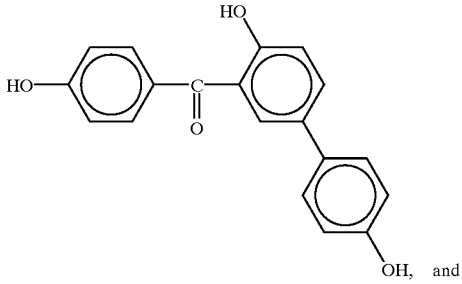
(26)

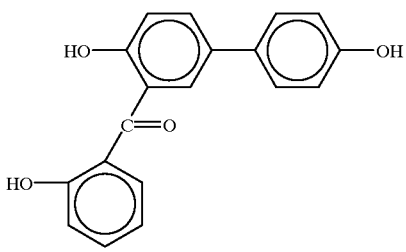
(27)

As an example of aromatic dihydroxy compounds (c) represented by formula (18), a compound represented by the following formula (28) can be mentioned.

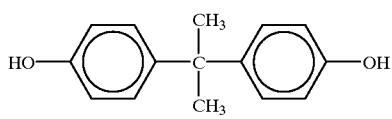
(28)

As examples of oxidation products of the above-mentioned aromatic dihydroxy compounds (c) represented by formula (28), compounds represented by the following formulae (29) and (30) can be mentioned.

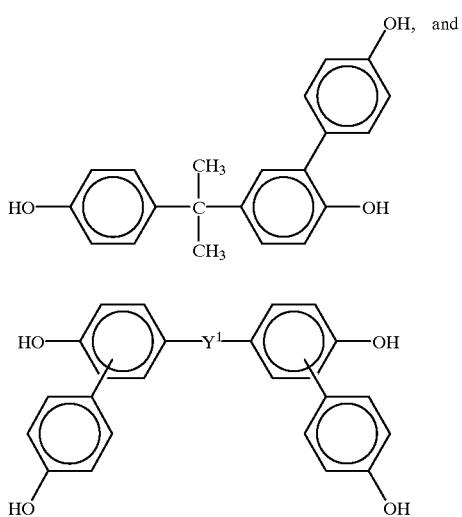

wherein $Y^1$ is as defined above.

The reason why the above-mentioned oxidation product (a) of an aromatic monohydroxy compound is likely to be present in the system for the transesterification for the production of an aromatic carbonate, for example, is that such an oxidation product is formed by the oxidation of an aromatic monohydroxy compound with a very small amount of oxygen which occasionally enters the system for the transesterification, or that such an oxidation product is occasionally present as a contaminant of an aromatic monohydroxy compound as a raw material and enters the system together with the raw material. Representative examples of type (a) oxidation products, namely, oxidation products of aromatic monohydroxy compounds include dihydroxybenzene (isomers), dihydroxy diphenyl (isomers), and the like.

Product (b) produced by the Fries rearrangement of a diaryl carbonate is likely to be formed as a by-product in the production of the diaryl carbonate. Examples of products (b) include 2,2'-dihydroxybenzophenone, 2,4'-dihydroxybenzophenone and 4,4'-dihydroxybenzophenone.

The aromatic dihydroxy compound (c) is a compound which is usually used as a monomer for the production of an aromatic polycarbonate. An aromatic polycarbonate can be produced by a transesterification of the above-mentioned aromatic dihydroxy compound (c) with a diaryl carbonate, wherein an aromatic monohydroxy compound is by-produced. When such a by-produced aromatic monohydroxy compound is used as a raw material in the process of the present invention, the aromatic dihydroxy compound (c) is likely to be introduced into the system for the transesterification for the production of an aromatic carbonate. Examples of aromatic dihydroxy compounds (c) include 2,2-bis-(4-hydroxyphenyl)propane, and the like.

Further, 2,2-bis-(4-hydroxyphenyl)propane usually contains aromatic polyhydroxy compounds represented by the following formulae, which compounds are also included in the aromatic polyhydroxy compound defined in the present invention.

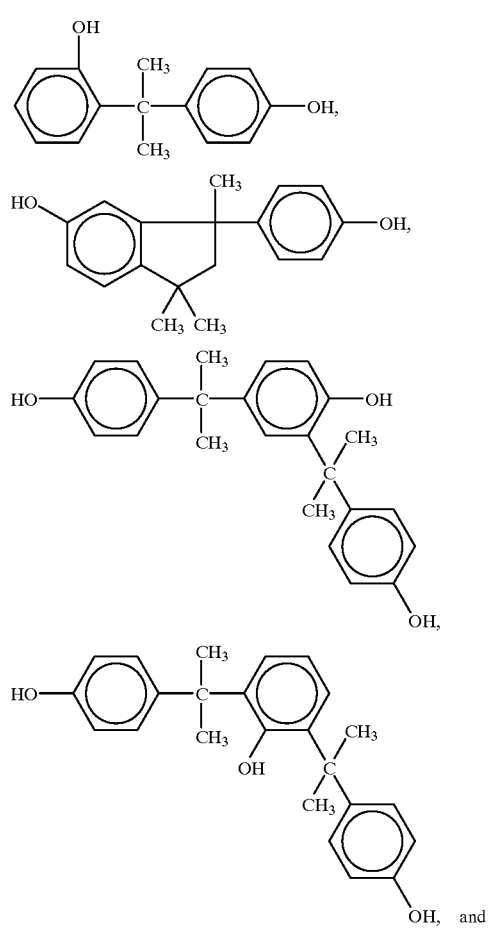

-continued

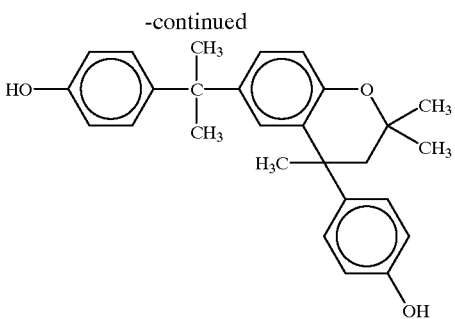

In the present invention, the aromatic carboxy compound, which is one of the high boiling point substances, is represented by the following formula (9):

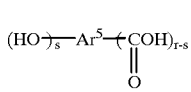

(9)

wherein $Ar^5$ represents an aromatic group having a valence of r, r represents an integer of 1 or more, s represents an integer of from 0 to r−1, and each of the —OH group and the —(COOH) group is individually bonded to an arbitrary ring-carbon position of the $Ar^5$ group, and The residue of the aromatic carboxy compound is represented by the following formula (10):

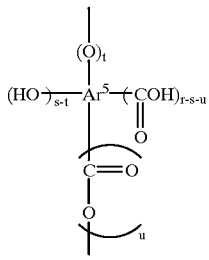

(10)

wherein $Ar^5$, r and s are as defined above, t represents an integer of from 0 to s, u represents an integer of from 0 to r—s, with the proviso that t and u are not simultaneously 0, and each of the —OH group, the —(COOH) group, the —O— group and the —(COO)— group is individually bonded to an arbitrary ring-carbon position of the $Ar^5$ group.

The residue of the aromatic carboxy compound, which is represented by formula (10), is present in such a form as chemically bonded to at least one member selected from the group consisting of a metal of the metal-containing catalyst, an alkoxycarbonyl group derived from the dialkyl carbonate or the alkyl aryl carbonate, an alkyl group formed by the decarboxylation reaction of the alkoxycarbonyl group, an aryloxycarbonyl group derived from the alkyl aryl carbonate or the diaryl carbonate, an aryl group formed by the decarboxylation reaction of the aryloxycarbonyl group, and a carbonyl group derived from the dialkyl carbonate, the alkyl aryl carbonate or the diaryl carbonate.

Examples of these aromatic carboxy compounds and compounds having residues of such aromatic carboxy compounds include aromatic carboxylic acids, such as benzoic acid, terephthalic acid, isophthalic acid and phthalic acid; aromatic carboxylic acid esters, such as methyl benzoate, phenyl benzoate and dimethyl terephthalate; hydroxyaromatic carboxylic acids, such as salicylic acid, p-hydroxybenzoic acid, m-hydroxybenzoic acid, dihydroxybenzoic acid (isomers), carboxydiphenol (isomers) and 2-(4-hydroxyphenyl)-2-(3'-carboxy-4'-hydroxyphenyl)propane; aryloxycarbonyl-(hydroxy)-arenes, such as phenyl salicylate, phenyl p-hydroxybenzoate, tolyl salicylate, tolyl p-hydroxybenzoate, phenyl dihydroxybenzoate (isomers), tolyl dihydroxybenzoate (isomers), phenyl dihydroxybenzoate (isomers), phenoxycarbonyldiphenol (isomers) and 2-(4-hydroxyphenyl)-2-(3'-phenoxycarbonyl-4'-hydroxyphenyl)propane; alkoxycarbonyl-(hydroxy)-arenes, such as methyl salicylate, methyl p-hydroxybenzoate, ethyl salicylate, ethyl p-hydroxybenzoate, methyl dihydroxybenzoate (isomers), methoxycarbonyldiphenol (isomers) and 2-(4-hydroxyphenyl)-2-(3'-methoxycarbonyl-4'-hydroxyphenyl)propane; aryloxycarbonyl-(alkoxy)-arenes, such as phenyl methoxybenzoate (isomers), tolyl methoxybenzoate (isomers), phenyl ethoxybenzoate (isomers), tolyl ethoxybenzoate (isomers), phenyl hydroxy-methoxybenzoate (isomers), hydroxy-methoxy-(phenoxycarbonyl)-diphenyl (isomers), 2-(4-methoxyphenyl)-2-(3'-phenoxycarbonyl-4'-hydroxyphenyl)propane and 2-(4-hydroxyphenyl)-2-(3'-phenoxycarbonyl-4'-methoxyphenyl)propane; aryloxycarbonyl-(aryloxy)-arenes, such as phenyl phenoxybenzoate (isomers), tolyl phenoxybenzoate (isomers), tolyl tolyloxybenzoate (isomers), phenyl hydroxy-phenoxy-benzoate (isomers), hydroxyphenoxy-(phenoxycarbonyl)-diphenyl (isomers), 2-(4-phenoxyphenyl)-2-(3'-phenoxycarbonyl-4'-hydroxyphenyl)propane and 2-(4-hydroxyphenyl)-2-(3'-phenoxycarbonyl-4'-phenoxyphenyl)propane; alkoxycarbonyl-(alkoxy)-arenes, such as methyl methoxybenzoate (isomers), ethyl methoxybenzoate (isomers), methyl ethoxybenzoate (isomers), ethyl ethoxybenzoate (isomers), methyl hydroxy-methoxybenzoate (isomers), hydroxy-methoxy-(methoxycarbonyl)-diphenyl (isomers), 2-(4-methoxyphenyl)-2-(3'-methoxycarbonyl-4'-hydroxyphenyl)propane and 2-(4-hydroxyphenyl)-2-(3'-methoxycarbonyl-4'-methoxyphenyl)propane; alkoxycarbonyl-(aryloxy)-arenes, such as methyl phenoxybenzoate (isomers), ethyl phenoxybenzoate (isomers), methyl tolyloxybenzoate (isomers), ethyl tolyloxybenzoate (isomers), phenyl hydroxy-methoxy-benzoate (isomers), hydroxy-methoxy-(phenoxycarbonyl)-diphenyl (isomers), 2-(4-methoxyphenyl)-2-(3'-phenoxycarbonyl-4'-hydroxyphenyl)propane and 2-(4-hydroxyphenyl)-2-(3-phenoxycarbonyl-4'-methoxyphenyl)propane (isomers); aryloxycarbonyl-(aryloxycarbonyloxy)-arenes, such as phenyl phenoxycarbonyloxybenzoate (isomers), tolyl phenoxycarbonyloxybenzoate (isomers), tolyl tolyloxycarbonyloxybenzoate (isomers), phenyl hydroxy-phenoxycarbonyloxybenzoate (isomers), hydroxy-phenoxycarbonyloxy-(phenoxycarbonyl)-diphenyl (isomers), 2-[4-(phenoxycarbonyloxy)phenyl]-2-(3'-phenoxycarbonyl-4'-hydroxyphenyl)propane and 2-(4-hydroxyphenyl)-2-[3'-phenoxycarbonyl-4'-(phenoxycarbonyloxy)phenyl]propane; aryloxycarbonyl-(alkoxycarbonyloxy)-arenes, such as phenyl methoxycarbonyloxybenzoate (isomers), tolyl methoxycarbonyloxybenzoate (isomers), phenyl ethoxycarbonyloxybenzoate (isomers), tolyl ethoxycarbonyloxybenzoate (isomers), phenyl hydroxy-methoxycarbonyloxybenzoate (isomers), hydroxy-methoxycarbonyloxy-(phenoxycarbonyl)-diphenyl (isomers), 2-[4-(methoxycarbonyloxy)phenyl]-2-(3'-phenoxycarbonyl-4'-hydroxyphenyl)propane and 2-(4-hydroxyphenyl)-2-[3'-phenoxycarbonyl-4'-(methoxycarbonyloxy)phenyl]

propane; alkoxycarbonyl-(aryloxycarbonyloxy)-arenes, such as methyl phenoxycarbonyloxybenzoate (isomers), ethyl phenoxycarbonyloxybenzoate (isomers), methyl tolyloxycarbonyloxybenzoate (isomers), ethyl tolyloxycarbonyloxybenzoate (isomers), methyl hydroxyphenoxycarbonyloxy-benzoate (isomers), hydroxyphenoxycarbonyloxy-(methoxycarbonyl)-diphenyl (isomers), 2-[4-(phenoxycarbonyloxy)phenyl]-2-(3'-methoxycarbonyl-4'-hydroxyphenyl)propane and 2-(4-hydroxyphenyl)-2-[3'-methoxycarbonyl-4'-(phenoxycarbonyloxy)phenyl]propane; and alkoxycarbonyl-(alkoxycarbonyloxy)-arenes, such as methyl methoxycarbonyloxybenzoate (isomers), ethyl methoxycarbonyloxybenzoate (isomers), methyl ethoxycarbonyloxybenzoate (isomers), ethyl ethoxycarbonyloxybenzoate (isomers), methyl hydroxy-methoxycarbonyloxybenzoate (isomers), hydroxy-methoxycarbonyloxy-(methoxycarbonyl)-diphenyl (isomers), 2-[4-(methoxycarbonyloxy)phenyl]-2-(3'-methoxycarbonyl-4'-hydroxyphenyl)propane and 2-(4-hydroxyphenyl)-2-[3'-methoxycarbonyl-4'-(methoxycarbonyloxy)phenyl] propane.

Of these aromatic carboxy compounds and compounds having residues of such aromatic carboxy compounds, attention should be made to those which are likely to be present in the system for the transesterification for the production of an aromatic carbonate. As such an aromatic carboxy compound and a compound having a residue of such an aromatic carboxy compound, there can be mentioned at least one member selected from the group consisting of:

(d) at least one member selected from the group consisting of a product produced by the Fries rearrangement of an aromatic carbonate obtained by the transesterification and a derivative of the product and (e) at least one member selected from the group consisting of a product produced by the Fries rearrangement of a reaction product obtained by the transesterification of the aromatic polyhydroxy compound and a derivative of the product.

As mentioned above, in the process for producing aromatic carbonates of the present invention, the reactions of producing methyl phenyl carbonate and diphenyl carbonate from dimethyl carbonate and phenol are especially important. Therefore, taking these reactions as examples, examples of aromatic carboxy compounds and compounds having residues of such aromatic carboxy compounds, which are included in (d) and (e) above are enumerated below.

Examples of (d) include salicyclic acid, p-hydroxybenzoic acid, phenyl salicylate, phenyl p-hydroxybenzoate, methyl salicylate, methyl p-hydroxybenzoate, phenyl methoxybenzoate (isomers), phenyl phenoxybenzoate (isomers), phenyl phenoxycarbonyloxybenzoate (isomers), methyl phenoxycarbonyloxybenzoate (isomers), methyl methoxycarbonyloxybenzoate (isomers).

Examples of (e) include dihydroxybenzoic acid (isomers), phenyl dihydroxybenzoate (isomers), phenoxycarbonyldiphenol (isomers), 2-(4-hydroxyphenyl)-2-(3'-phenoxycarbonyl-4'-hydroxyphenyl)propane.

Examples of xanthones belonging to the high boiling point substances in the present invention include xanthone and those in which the aromatic ring of xanthone is substituted with at least one substituent selected from the group consisting of an alkyl group, such as methyl, ethyl, propyl, isopropyl, butyl, iso-butyl and the like; a hydroxy group; an alkoxy group, such as methoxy, ethoxy, propoxy, isopropoxy, butoxy and the like; aryloxy group, such as phenoxy, tolyloxy and the like; an alkoxycarbonyloxy group, such as methoxycarbonyloxy, ethoxycarbonyloxy, propoxycarbonyloxy, butoxycarbonyloxy and the like; an aryloxycarbonyloxy group, such as phenoxycarbonyloxy, tolyloxycarbonyloxy and the like; a carboxy group; an alkoxycarbonyl group, such as methoxycarbonyl, ethoxycarbonyl and the like; an aryloxycarbonyl group, such as phenoxycarbonyl, tolyloxycarbonyl and the like; an arylcarbonyloxy group, such as benzoyloxy, tolylcarbonyloxy and the like.

The functional substance (C) used in the present invention is a substance which is capable of reacting with at least one component selected from the group consisting of the high boiling point substance (A) and the metal-containing catalyst (B). There is no particular limitation with respect to the functional substance (C), as long as the substance is capable of forming at least one reaction product selected from the group consisting of an (A)/(C) reaction product {which is a reaction product of the functional substance (C) with the high boiling point substance (A)} and a (B)/(C) reaction product {which is a reaction product of the functional substance (C) with the metal-containing catalyst (B)}. Examples of such a functional substance (C) include oxidizing agents, reducing agents, precipitants, adsorbents and reactive solvents. Of these, oxidizing agents, precipitants and reactive solvents are preferred. Further, these functional substances may be used individually, or at least two different functional substances may be simultaneously or stepwise added to the taken-out catalyst-containing liquid. Further, the reaction of the functional substance (C) with the high boiling point substance (A) and/or the metal-containing catalyst (B) can be carried out in a batchwise or a continuous manner.

In the present invention, when the functional substance (C) is capable of reacting with the high boiling point substance (A), the (A)/(C) reaction product is a product formed by the reaction between the high boiling point substance (A) and the functional substance (C). However, when the functional substance (C) is not capable of reacting with the high boiling point substance (A), the unreacted high boiling point substance (A) is regarded as the (A)/(C) reaction product. On the other hand, when the functional substance (A) is capable of reacting with the metal-containing catalyst (B), the (B)/(C) reaction product is a product formed by the reaction between the metal-containing catalyst (B) and the functional substance (C). However, when the functional substance (C) is not capable of reacting with the metal-containing catalyst (B), the unreacted metal-containing catalyst (B) is regarded as the (B)/(C) reaction product.

In the present invention, the (A)/(C) reaction product is withdrawn from the production system for the desired aromatic carbonates, whereas the (B)/(C) reaction product is recycled to the reaction system comprising the starting material and the reactant. The withdrawal of the (A)/(C) reaction product can be carried out, for example, by separating the (A)/(C) reaction product from the (B)/(C) reaction product during and/or after the reaction of the high boiling point substance (A) with the functional substance (C).

With respect to the method for separating the (A)/(C) reaction product from the (B)/(C) reaction product, any methods can be employed as long as the catalyst-containing liquid can be separated into a component which is composed mainly of the (A)/(C) reaction product and a component which is composed mainly of the (B)/(C) reaction product. Examples of such separation methods include a gas phase-condensed phase separation method, such as a gas phase-liquid phase separation method, a gas phase-solid phase separation method or a gas phase-solid/liquid mixed phase separation method; a solid phase-liquid phase separation method, such as sedimentation, centrifugation or filtration; a distillation method; an extraction method; and an adsorption method. Of these, the sedimentation, the distillation and the adsorption method are preferred. These separation methods can be employed individually, or at least two of such separation methods can be simultaneously or stepwise employed.

With respect to the combination of the functional substance (C) and the separation method, there is no particular limitation. However, examples of the preferred modes usable for practicing the method of the present invention, in which specific combinations of the functional substance (C) and the separation method are used, include:

(I) a mode in which the functional substance (C) is an oxidizing agent, so that an oxidation reaction is performed with respect to the catalyst-containing liquid, in which the (A)/(C) reaction product is a low boiling point oxidation product and the (B)/(C) reaction product is a metal oxide; and the separation method is the gas phase-condensed phase separation method, (II) a mode in which the functional substance (C) is a precipitant, so that a precipitation reaction is performed with respect to the catalyst-containing liquid, in which the (B)/(C) reaction product is a metal-containing substance which precipitates; and the separation method is the solid-liquid separation method, (III) a mode in which the functional substance (C) is a reactive solvent, so that a solvolysis reaction is performed with respect to the catalyst-containing liquid, in which the (A)/(C) reaction product is a low-boiling point solvolysis product; and the separation method is the distillation method.

When the preferred mode of item (I) above is employed, use is made of an oxidizing agent which not only can oxidize the high boiling point substance (A) to form a low boiling point oxidation product as the (A)/(C) reaction product, but also can oxidize the metal-containing catalyst (B) to form a metal oxide as the (B)/(C) reaction product. Examples of oxidizing agents include air; molecular oxygen; ozone; hydrogen peroxide; silver oxide; organic peroxides, such as peracetic acid, perbenzoic acid, benzoyl peroxide, tert-butyl hydroperoxide and cumyl hydroperoxide; oxo-acids, such as nitrous acid, nitric acid, chloric acid, hypochlorous acid; and salts thereof. Of these, air, molecular oxygen, ozone, hydrogen peroxide, nitrous acid and nitric acid are preferred, and air and molecular oxygen are more preferred.

The type of the reaction performed in the catalyst-containing liquid using the oxidizing agent varies depending on the type of the oxidizing agent and the reaction conditions. However, the reaction is performed in a phase selected from the group consisting of a liquid phase, a gas-liquid mixed phase and a gas-liquid/solid mixed phase. The reaction temperature varies depending on the type of the oxidizing agent; however, the reaction temperature is generally in the range of from −30 to 2,000° C., preferably from 0 to 1,200° C., more preferably from 0 to 900° C. The reaction time varies depending on the type of the oxidizing agent and the reaction temperature; however, the reaction time is generally in the range of from 0.001 to 100 hours, preferably from 0.1 to 20 hours. The reaction pressure is generally in the range of from 10 to $10^7$ Pa, preferably $10^2$ to $3 \times 10^6$ Pa. The reaction can be performed in either a batchwise or a continuous manner.

In the preferred mode of item (I) above, the gas phase-condensed phase separation method is employed to separate the (A)/(C) reaction product from the (B)/(C) reaction product. The condensed phase means a liquid phase, a solid phase or a solid/liquid mixed phase. In the case where the oxidation reaction mixture obtained at the completion of the oxidation reaction forms a liquid phase, a gas/liquid mixed phase or a gas/solid/liquid mixed phase, the reaction mixture is separated into a gas phase composed mainly of a low boiling point oxidation product and a condensed phase containing a metal oxide. Then, by distilling off or evaporating the low boiling point oxidation product from the separated condensed phase, a metal oxide-rich condensed phase (composed mainly of the metal oxide) can be obtained. Alternatively, when the metal oxide (formed by the oxidation of the metal-containing catalyst (B) which is conducted with respect to the catalyst-containing liquid) forms a solid phase during the oxidation reaction, it is possible to obtain a reaction mixture in the form of a liquid-solid mixture. Further, during the oxidation reaction, the low boiling point oxidation product formed by oxidation of the high boiling point substance (A) may be evaporated together with the volatile components of the liquid reaction system, to thereby obtain a solid reaction mixture. This method is preferred, because it becomes possible to separate the oxidation reaction system into the solid phase composed mainly of the metal oxide and the gas phase containing the low boiling point oxidation product while performing the oxidation reaction.

The "low boiling point oxidation product" means compounds having a boiling point lower than that of the high boiling point substance (A), which are formed by oxidation of the high boiling point substance (A) using the oxidizing agent. The type of the low boiling point oxidation product varies depending on the type of the oxidizing agent and the type of the high boiling point substance (A). Examples of low boiling point oxidation products include carbon dioxide, water, carbon monoxide, oxygen-containing organic compounds, unsaturated organic compounds, compounds formed by the decomposition of the high boiling point substance.

The "metal oxide" means an oxide of the metal of the metal-containing catalyst (B). A single type of the metal-containing catalyst (B) may form different metal oxides depending on the oxidation reaction conditions and the type of the metal contained in the catalyst (B). Specific examples of metal oxides include $PbO$, $PbO_2$, $Pb_3O_4$, $CuO$, $Cu_2O$, $Li_2O$, $ZnO$, $CdO$, $FeO$, $Fe_3O_4$, $Fe_2O_3$, $CoO$, $Co_3O_4$, $Co_2O_3$, $CoO_2$, $NiO$, $ZrO_2$, $Al_2O_3$, $TiO$, $Ti_2O_3$, $TiO_2$, $SnO$ and $SnO_2$. When the metal-containing catalyst (B) contains a plurality of different metals, there is or are obtained a mixture of metal oxides corresponding to the metals contained in the catalyst (B) or/and a compound metal oxide.

When the preferred mode of item (II) above is employed, there is no particular limitation with respect to the metal-containing substance formed as the (B)/(C) reaction product, as long as the metal-containing substance is present in a solid state in the precipitation reaction mixture, and contains the metal. Examples of metal-containing substances include metal hydroxides; metal chalcogenides, such as a metal oxide and a metal sulfide; salts of inorganic acids, such as a metal carbonate and a metal sulfate; metal salts of organic acids; metal complexes; and metal double salts.

Of these, from the viewpoint of the low solubility in the reaction mixture, a metal carbonate, a metal hydroxide, a metal oxide, a metal sulfide and a metal sulfate are preferred. Each of the metal-containing substances may contain other substance (such as the reactant, the starting material and the high boiling point substance) coordinated thereto.

With respect to the precipitant, there is no particular limitation, as long as the precipitant can react with the metal-containing catalyst (B) to form the above-mentioned metal-containing substance. For example, for precipitating metal hydroxides, use can be made of inorganic hydroxides (such as a hydroxide of an alkali metal or an alkaline earth metal) and water; for precipitating metal oxides, use can be made of inorganic oxides (such as an oxide of an alkali metal or an alkaline earth metal) and oxidizing agents (such as hydrogen peroxide); for precipitating metal sulfides, use can be made of inorganic sulfides (such as a sulfide of an alkali metal or an alkaline earth metal) and hydrogen sulfide; for precipitating metal carbonates, use can be made of inorganic carbonates (such as a carbonate of an alkali metal or an alkaline earth metal), carbonic acid and carbon dioxide with water; for precipitating metal sulfates, use can be made of inorganic sulfates (such as a sulfate of an alkali metal or an alkaline earth metal), sulfuric acid and sulfur trioxide with water.

The type of the reaction between the metal-containing catalyst (B) and the precipitant varies depending on the type of the catalyst, the type of the precipitant, the reaction conditions and the like. However, the reaction is generally performed in a phase selected from the group consisting of a liquid phase, a liquid-gas mixed phase, a gas-liquid-solid mixed phase and a solid-liquid mixed phase. The reaction temperature varies depending on the type of the precipitant; however, the reaction temperature is generally in the range of from −70 to 600° C., preferably from −30 to 400° C., more preferably from −10 to 250° C. The reaction time varies depending on the type of the precipitant and the reaction temperature; however, the reaction time is generally in the range of from 0.001 to 100 hours, preferably from 0.1 to 20 hours. The reaction pressure is generally in the range of from 10 to $10^7$ Pa. The above-mentioned reaction can be performed in either a batchwise manner or a continuous manner.

In the present invention, it is preferred to add a substance which serves as a crystal nucleus to the precipitation reaction system. At the time of the separation of the metal-containing substance from the precipitation reaction mixture, the metal-containing substance needs to be in a solid state. However, the metal-containing substance need not be in a solid state during the precipitation reaction, as long as the metal-containing substance becomes a solid by a cooling operation, etc. after the completion of the reaction.

In the preferred mode of item (II) above, the solid phase-liquid phase separation method is employed to separate the (A)/(C) reaction product from the (B)/(C) reaction product. Specifically, the precipitation reaction mixture is separated into a solid phase composed mainly of a metal-containing substance and a liquid phase composed mainly of substances originating from a high boiling point substance. The solid phase-liquid phase separation method is generally conducted by sedimentation, centrifugation, filtration or the like.

Further, in the preferred mode of item (II) above, the high boiling point substance (A) contained in the catalyst-containing liquid does not undergo the precipitation reaction with the functional substance (C) [therefore, in this preferred mode, the unreacted component (A), which is not precipitated when the functional substance (C) is added, is regarded as the (A)/(C) reaction product]; however, the high boiling point substance (A) may undergo a reaction other than the precipitation reaction during the precipitation reaction of the metal-containing catalyst (B).

When the preferred mode of item (III) above is employed, there is no particular limitation with respect to the reactive solvent, as long as the reactive solvent can react with the high boiling point substance (A) to form compounds having a boiling point lower than the boiling point of the high boiling point substance (A). Examples of reactive solvents include water; lower alcohols, such as methanol, ethanol, propanol (isomer) and butanol (isomer); lower carboxylic acids, such as formic acid, acetic acid and propionic acid; and carbonates, such as dimethyl carbonate and diethyl carbonate. Of these, water, methanol, ethanol, acetic acid, methyl acetate, ethyl acetate, dimethyl carbonate, diethyl carbonate and the like are preferred, and water is more preferred.

In the present invention, the "solvolysis" means the decomposition reaction of the high boiling point substance (A) with the reactive solvent. The reaction product obtained by the solvolysis may be subjected to further reaction other than the solvolysis, such as the decarboxylation and the like.

With respect to the low boiling point product obtained by the solvolysis, there is no particular limitation, as long as the low boiling point product has a boiling point lower than the boiling point of the high boiling point substance (A). The type and structure of the low boiling point product vary depending on the type of the reactive solvent and the type of the high boiling point substance (A). With respect to the relationship between the reactive solvent, the high boiling point substance (A) and the low boiling point product, specific explanation is made below, taking as an example the case where the high boiling point substance (A) is phenyl salicylate which is one of the aromatic carboxy compounds.

(i) When the reactive solvent is water, phenol and salicylic acid are formed by the hydrolysis, and the formed salicylic acid undergoes decarboxylation to form phenol and carbon dioxide.

(ii) When the reactive solvent is an alcohol, an alkyl salicylate and phenol are formed by alcoholysis.

(iii) When the reactive solvent is a carboxylic acid, salicylic acid and a phenyl carboxylate are formed by transesterification, and the formed salicylic acid undergoes decarboxylation to form phenol and carbon dioxide.

As mentioned above, the above explanation is made, taking as an example phenyl salicylate, which has a relatively simple structure as an aromatic carboxy compound. However, also in the case of an aromatic carboxy compound having a more complicated structure, the same types of reactions as mentioned in items (i) to (iii) above occur. Therefore, as the reaction products corresponding to those mentioned in items (i) to (iii) above, there can be obtained, for example, an aromatic hydroxy compound, such as an aromatic monohydroxy compound; a lower carboxylic acid ester of an aromatic monohydroxy compound; an ester of an aromatic carboxy compound with a lower alcohol; and carbon dioxide. Of the above-mentioned reaction products obtained by the solvolysis, the aromatic monohydroxy compound is especially preferred, because this product is a reactant used in the present invention so that this product can be recycled.

The catalyst-containing liquid contains the metal-containing catalyst (B), and the catalyst (B) generally also serves as a catalyst for the solvolysis. Therefore, it is not necessary to specifically use a catalyst for the solvolysis, but such a catalyst for the solvolysis can be used for the purpose of improving the reaction rate, etc.

The type of the reaction between the high boiling point substance (A) and the reactive solvent varies depending on the reaction conditions; however, the reaction is generally performed in a phase selected from the group consisting of a liquid phase and a solid-liquid mixed phase. The reaction temperature varies depending on the type of the reactive solvent; however, the reaction temperature is generally in the range of from −30 to 400° C., preferably from −10 to 300° C., more preferably from 0 to 250° C. The reaction time varies depending on the type of the reactive solvent and the reaction temperature; however, the reaction time is generally in the range of from 0.001 to 100 hours, preferably from 0.1 to 20 hours. The reaction pressure is generally in the range of from 10 to $10^7$ Pa. The reaction can be performed in either a batchwise manner or a continuous manner.

The metal-containing catalyst (B) may or may not undergo the solvolysis [therefore, in this preferred mode, when the metal-containing catalyst (B) does not undergo the solvolysis, the unreacted component (B), which is not solvolyzed with the functional substance (C), is regarded as the (B)/(C) reaction product]. In the case where water or an alcohol is used as a reactive solvent so as to solvolyze an aromatic carboxy compound contained as the high boiling point substance (A) in the catalyst-containing liquid, a decarboxylation reaction occurs simultaneously with the solvolysis, so that carbon dioxide is formed as one of the reaction products originating from the high boiling point substance (A). Therefore, it is possible that the formed carbon dioxide serves as a precipitant and reacts with the metal-containing catalyst (B) to there-by form a metal-containing substance (such as a metal carbonate) in the form of a solution thereof and/or in the form of a solid.

In the preferred mode of item (III) above, the separation of the (A)/(C) reaction product from the (B)/(C) reaction product is conducted by a distillation method, wherein a low boiling point product formed as the (A)/(C) reaction product by the solvolysis is removed from the solvolysis reaction mixture as a distillate. The (B)/(C) reaction product is contained in the liquid remaining in the distillation column employed. The distillation temperature is generally in the range of from 10 to 300° C., preferably from 50 to 250° C., in terms of the temperature of the liquid in the distillation column. The distillation pressure is generally in the range of from 0.1 to $1.0 \times 10^6$ Pa, preferably from 1.0 to $1.0 \times 10^5$ Pa. The distillation can be conducted either in a batchwise manner or a continuous manner.

The recycling of the (B)/(C) reaction product to the reaction system can be conducted by a method in which the (B)/(C) reaction product, which has been separated from the (A)/(C) reaction product and which is in the form of a liquid, a solid or a liquid-solid mixture, as such, is recycled to the reaction system. Alternatively, when the (B)/(C) reaction product is obtained in such a form as contains other components than the reaction product, the recycling of the (B)/(C) reaction product can be conducted by a method in which a part or all of such other components are separated from the other components-containing (B)/(C) reaction product, and the resultant is recycled to the reaction system. Further, the recycling of the (B)/(C) reaction product can be conducted by a method in which the separated (B)/(C) reaction product is mixed and/or reacted with the starting material or the reactant, and the resultant (i.e., a liquid reaction mixture, a slurry, etc.) is recycled to the reaction system. This method is advantageous when the (B)/(C) reaction product is in the form of a solid or a solid-liquid mixture. The recycling of the (B)/(C) reaction product to the reaction system can be conducted in either a batch-wise manner or in a continuous manner.

As mentioned above, the method of the present invention comprises:

taking out at least one type of catalyst-containing liquid which is selected from the group consisting of:
  a portion of the high boiling point reaction mixture obtained by the transesterification reaction before the separation of the high boiling point reaction mixture into the product fraction and the liquid catalyst fraction, and
  a portion of the separated liquid catalyst fraction,
  each portion containing at least one high boiling point substance (A) having a boiling point higher than the boiling point of the produced aromatic carbonate and containing the metal-containing catalyst (B); and
  adding to the taken-out catalyst-containing liquid a functional substance (C) capable of reacting with at least one component selected from the group consisting of the component (A) and the component (B).

With respect to the amount of the portion of the high boiling point reaction mixture, which is taken out as the catalyst-containing liquid, the amount is from 0.01 to 10% by weight, preferably from 0.1 to 5% by weight, more preferably from 0.3 to 1% by weight, based on the weight of the high boiling point reaction mixture. On the other hand, with respect to the amount of the portion of the separated liquid catalyst fraction, which is taken out as the catalyst-containing liquid, the amount is from 0.01 to 40% by weight, preferably from 0.1 to 20% by weight, more preferably from 1 to 10% by weight, based on the weight of the separated liquid catalyst fraction.

With respect to the concentration of the high boiling point substance (A) in the taken-out catalyst-containing liquid, the concentration varies depending on the type of the high boiling point substance (A). However, too low a concentration of the high boiling point substance (A) is not preferable, since the amount of the taken-out catalyst-containing liquid becomes too large. On the other hand, too high a concentration of the high boiling point substance (A) is also not preferable, since the boiling point and viscosity of the taken-out catalyst-containing liquid become too high, so that the handling of the taken-out catalyst-containing liquid becomes difficult. Therefore, the concentration of the high boiling point substance (A) in the taken-out catalyst-containing liquid is generally from 0.01 to 99% by weight, preferably from 0.1 to 95% by weight, more preferably from 1 to 90% by weight.

Further, when the high boiling point substance (A) is an aromatic polyhydroxy compound, for preventing the catalyst from depositing on or adhering to the inner walls of the reactor, the pipes and the like, it is preferred that the taken-out catalyst-containing liquid contains the aromatic polyhydroxy compound and the metal-containing catalyst in amounts such that the weight ratio of the aromatic polyhydroxy compound to the metal of the catalyst becomes 2.0 or less.

With respect to the separation of the desired aromatic carbonate from the product fraction (separated from the high boiling point reaction mixture obtained by the transesterification reaction) comprising the aromatic carbonate, the unreacted starting material and the unreacted reactant, the separation can be easily conducted by a conventional separation method, such as a distillation method.

In the present invention, the purity of the aromatic carbonate which has been separated from the product fraction can be calculated by the following formula:

Purity of the aromatic carbonate (%) =

$$\frac{\text{the aromatic carbonate (\% by weight)}}{100 - \text{the unreacted starting material (\% by weight)} - \text{the unreacted reacting material (\% by weight)}} \times 100$$

The purity of the aromatic carbonate obtained by the process of the present invention is generally 99% or more, preferably 99.5% or more, most preferably 99.8% or more.

In a further preferred aspect of the present invention, there is provided a mode of the above-mentioned process of the present invention, in which the above-mentioned steps (1), (2) and (3) are continuously conducted. That is, in this mode of the process, the following steps are continuously conducted:

(1) transesterifying, in the presence of a metal-containing catalyst, a starting material selected from the group consisting of a dialkyl carbonate, an alkyl aryl carbonate and a mixture thereof with a reactant selected from the group consisting of an aromatic monohydroxy compound, an alkyl aryl carbonate and a mixture thereof, to thereby obtain a high boiling point reaction mixture comprising the metal-containing catalyst and at least one aromatic carbonate, while withdrawing a low boiling point reaction mixture which contains a low boiling point by-product comprising an aliphatic alcohol, a dialkyl carbonate or a mixture thereof, (2) separating the high boiling point reaction mixture into a product fraction comprising the produced aromatic carbonate and a liquid catalyst fraction comprising the metal-containing catalyst, and (3) recycling the liquid catalyst fraction to the reaction system while withdrawing the product fraction, thereby enabling continuous production of the aromatic carbonate.

In this preferred mode for continuously producing the aromatic carbonate, it is especially preferred that the step (1) of the process of the present invention is performed as follows: the starting material and the reactant are continuously fed to a continuous multi-stage distillation column to effect a transesterification reaction therebetween in at least one phase selected from the group consisting of a liquid phase and a gas-liquid phase in the presence of a metal-containing catalyst, wherein a high boiling point reaction mixture containing the produced aromatic carbonate is withdrawn in a liquid form from a lower portion of the distillation column, while continuously withdrawing a low boiling point reaction mixture containing the low boiling point by-product in a gaseous form from an upper portion of the distillation column by distillation.

In another aspect of the present invention, there is provided a process for producing an aromatic polycarbonate, which comprises polymerizing the high purity diaryl carbonate obtained by the process of the present invention with an aromatic dihydroxy compound by transesterification.

With respect to the method for producing the aromatic polycarbonate by transesterification, reference can be made to, for example, U.S. Pat. No. 5,589,564. By the use of the diaryl carbonate obtained by the process of the present invention, it has become possible to perform the polymerization at a high rate. Further, the aromatic polycarbonate obtained by the transesterification reaction between the aromatic dihydroxy compound and the diaryl carbonate obtained by the process of the present invention is a high quality aromatic polycarbonate which is free from the discoloration.

The aromatic dihydroxy compound, which can be used for producing the aromatic polycarbonate by transesterification, can be represented by the following formula:

HO—Ar'—OH wherein Ar' represents a divalent aromatic group having from 5 to 200 carbon atoms.

Preferred examples of divalent aromatic groups Ar' having from 5 to 200 carbon atoms include an unsubstituted or substituted phenylene group, an unsubstituted or substituted naphthylene group, an unsubstituted or substituted biphenylene group and an unsubstituted or substituted pyridylene group. Further examples of such divalent aromatic groups include divalent groups, each represented by the following formula:

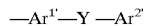

—Ar$^{1'}$—Y—Ar$^{2'}$ wherein each of Ar$^{1'}$ and Ar$^{2'}$ independently represents a divalent carbocyclic or heterocyclic aromatic group having from 5 to 70 carbon atoms, and Y' represents a divalent alkane group having from 1 to 30 carbon atoms.

In the divalent aromatic groups Ar$^{1'}$ and Ar$^{2'}$, at least one hydrogen atom may be substituted with a which does not adversely affect the reaction, such as a halogen atom, an alkyl group having from 1 to 10 carbon atoms, an alkoxy group having from 1 to 10 carbon atoms, a phenyl group, a phenoxy group, a vinyl group, a cyano group, an ester group, an amide group and a nitro group.

Illustrative examples of heterocyclic aromatic groups include an aromatic group having at least one hetero atom, such as a nitrogen atom, an oxygen atom or a sulfur atom.

Examples of divalent aromatic groups Ar$^{1'}$ and Ar$^{2'}$ include an unsubstituted or substituted phenylene group, an unsubstituted or substituted biphenylene group and an unsubstituted or substituted pyridylene group. Substituents for Ar$^{1'}$ and Ar$^{2'}$ are as described above.

Examples of divalent alkane groups Y' include organic groups respectively represented by the following formulae:

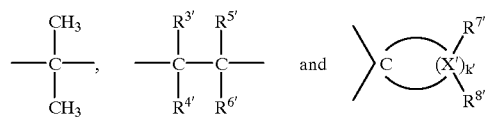

wherein each of R$^{3'}$, R$^{4'}$, R$^{5'}$ and R$^{6'}$ independently represents a hydrogen atom, an alkyl group having from 1 to 10 carbon atoms, an alkoxy group having from 1 to 10 carbon atoms, a cycloalkyl group having from 5 to 10 ring-forming carbon atoms, a carbocyclic aromatic group having from 5 to 10 ring-forming carbon atoms and a carbocyclic aralkyl group having from 6 to 10 ring-forming carbon atoms; k' represents an integer of from 3 to 11; each X' represents a carbon atom and has R$^{7'}$ and R$^{8'}$ bonded thereto; each R$^{7'}$ independently represents a hydrogen atom or an alkyl group having from 1 to 6 carbon atoms, and each R$^{8'}$ independently represents a hydrogen atom or an alkyl group having from 1 to 6 carbon atoms, wherein R$^{7'}$ and R$^{8'}$ are the same or different;

wherein at least one hydrogen atom of each of R$^{3'}$, R$^{4'}$, R$^{5'}$, R$^{6'}$, R$^{7'}$ and R$^{8'}$ may be independently replaced by a substituent which does not adversely affect the reaction, such as a halogen atom, an alkyl group having from 1 to 10 carbon atoms, an alkoxy group having from 1 to 10 carbon atoms, a phenyl group, a phenoxy group, a vinyl group, a cyano group, an ester group, an amide group and a nitro group.

Specific examples of divalent aromatic groups Ar' include groups respectively represented by the following formulae:

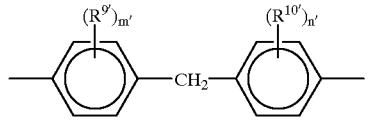

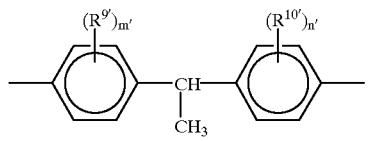

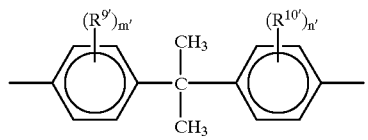

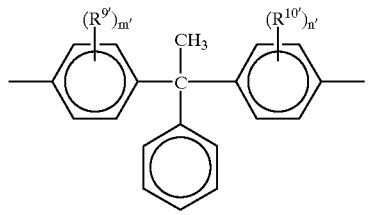

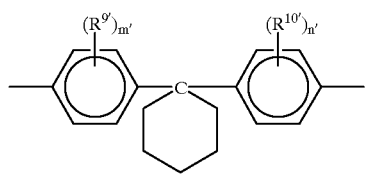

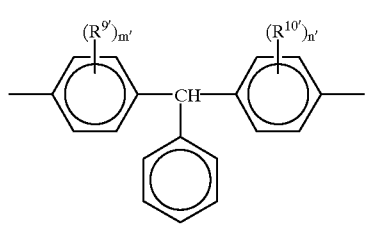

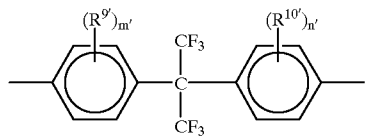

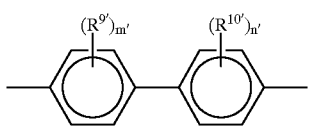

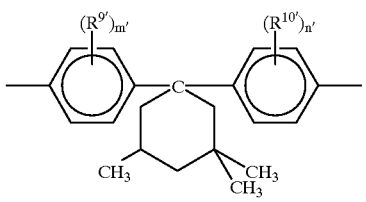

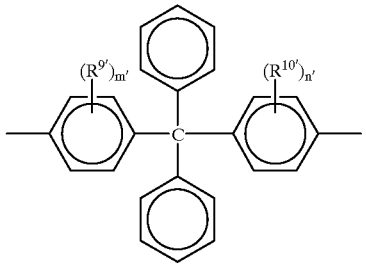

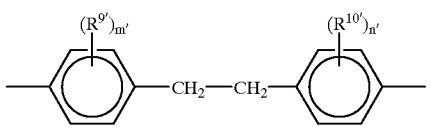

wherein each of $R^{9'}$ and $R^{10'}$ independently represents a hydrogen atom, a halogen atom, an alkyl group having from 1 to 10 carbon atoms, an alkoxy group having from 1 to 10 carbon atoms, a cycloalkyl group having from 5 to 10 ring-forming carbon atoms, or an allyl group having from 6 to 30 carbon atoms; each of m' and n' independently represents an integer of from 1 to 4, with the proviso that when m' is an integer of from 2 to 4, $R^{9'}$'s are the same or different, and when n' is an integer of from 2 to 4, $R^{10'}$'s are the same or different.

Further, examples of divalent aromatic groups Ar' also include those which are represented by the following formula:

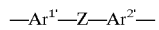

wherein $Ar^{1'}$ and $Ar^{2'}$ are as defined above; and Z' represents a single bond or a divalent group, such as —O—, —CO—, —S—, —SO$_2$, —SO—, —COO—, or —CON(R$^{3'}$)—, wherein R$^{3'}$ is as defined above.

Examples of such divalent aromatic groups Ar' include groups respectively represented by the following formulae:

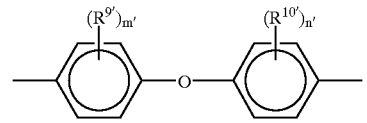

-continued

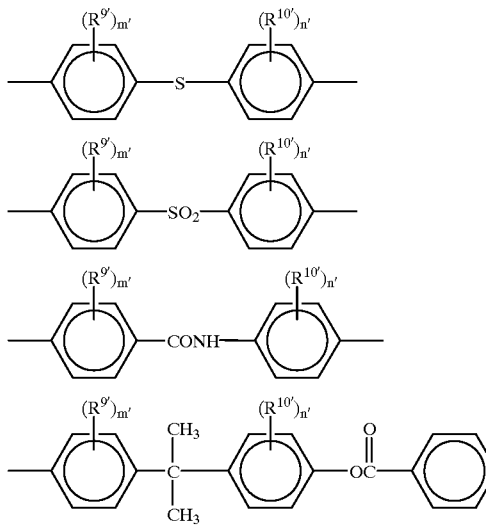
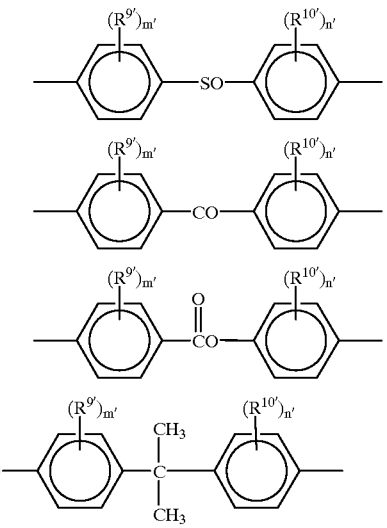

wherein $R^{9'}$, $R^{10'}$, m' and n' are as defined above.

The above-mentioned aromatic dihydroxy compounds can be used individually or in combination. Representative examples of aromatic dihydroxy compounds include bisphenol A.

With respect to the material of an apparatus used for producing the aromatic polycarbonate, there is no particular limitation. However, stainless steel, glass or the like is generally used as a material for at least the inner walls of the apparatus.

BEST MODE FOR CARRYING OUT THE INVENTION

Hereinbelow, the present invention will be described in more detail with reference to the following Examples and Comparative Examples, but they should not be construed as limiting the scope of the present invention.

In the following Examples and Comparative Examples, various measurements were conducted in accordance with the following methods.

The metal concentration of a metal-containing catalyst was measured by means of an ICP (inductively coupled plasma emission spectral analyzer) (JY38PII: manufactured and sold by Seiko Electronics Co, Ltd., Japan).

The concentration of an organic matter in a liquid was measured by gas chromatography.

The concentration of a high boiling point substance (A) coordinated to a metal-containing catalyst in a catalyst-containing liquid was measured by a method in which a ligand exchange with trifluoroacetic acid is conducted, followed by analysis by gas chromatography.

The total concentration of both high boiling point substances (A) coordinated to and not coordinated to a metal-containing catalyst in a catalyst-containing liquid was determined as follows. The catalyst-containing liquid was subjected to distillation using a small size distillation column and the total of the weight of a fraction having a boiling point higher than that of a desired aromatic carbonate and the weight of an organic matter contained in the distillation residue remaining in the distillation column was calculated. Then, the weight percentage of the thus calculated total weight, based on the weight of the catalyst-containing liquid, was obtained, and the obtained weight percentage was taken as the total concentration of both high boiling point substances (A) coordinated to and not coordinated to a metal-containing catalyst in the catalyst-containing liquid.

The number average molecular weight of a produced aromatic polycarbonate was measured by gel permeation chromatography (GPC) (apparatus: HLC-8020, manufactured and sold by Tosoh Corp., Japan; column: TSK-GEL, manufactured and sold by Tosoh Corp., Japan; solvent: tetrahydrofuran).

All of the concentrations are indicated by weight percentages.

EXAMPLE 1

Preparation of Catalyst

A mixture of 40 kg of phenol (hereinafter, frequently referred to as "PhOH") and 8 kg of lead monoxide was heated to and maintained at 180° C. for 10 hours, thereby performing a reaction. After that period of time, water formed in the resultant reaction mixture was distilled off together with unreacted phenol, to thereby obtain catalyst I.

Production of Aromatic Carbonate

The production of an aromatic carbonate was conducted using the system as shown in FIG. 1, which comprises continuous multi-stage distillation column 1 having a height of 6 m and a diameter of 6 inches and equipped with 20 sieve trays.

A mixture of dimethyl carbonate (hereinafter, frequently referred to as "DMC"), phenol (which contains, as an impurity, 30 ppm by weight of 4,4'-dihydroxydiphenyl which is a high boiling point substance) and catalyst I was continuously fed in liquid form from conduit 3 through preheater 4 and conduit 5 into continuous multi-stage distillation column 1 at a position of 0.5 m below top 2 thereof at a rate of 32 kg/hr, and was allowed to flow down inside multi-stage distillation column 1, thereby performing a reaction. The weight ratio of the dimethyl carbonate to the phenol in the mixture was 62/38, and catalyst I was used in an amount such that the Pb concentration of the reaction mixture in conduit 13 became 0.038% by weight, wherein the Pb concentration can be confirmed using a sample withdrawn through a sampling nozzle (not shown) provided on conduit 13. Dimethyl carbonate was fed from conduit 7 into evaporator 8 thereby forming a gas and the formed gas of dimethyl carbonate was fed through conduit 9 to bottom 6 of continuous multi-stage distillation column 1 at a rate of 26 kg/hr. The reaction conditions of the above reaction were such that the temperature at the bottom of continuous multi-stage distillation column 1 was 203° C. and the pressure at the top of continuous multi-stage distillation column 1 was $7.4 \times 10^5$ Pa. Gas distilled from column top 2 was led through conduit 10 into condenser 11, in which the gas was condensed. The resultant condensate was continuously withdrawn at a rate of 25 kg/hr through conduit 12. A reaction mixture [containing methyl phenyl carbonate (as a desired reaction product) (hereinafter, frequently referred to as "MPC"), the catalyst, and high boiling point substances] was continuously withdrawn from column bottom 6 at a rate of 34 kg/hr and led into evaporator 14 through conduit 13, from which an evaporated gas containing the methyl phenyl carbonate was withdrawn and led through conduit 21 into condenser 22, in which the gas was condensed. The resultant condensate was withdrawn from condenser 22 through conduit 23, wherein the condensate withdrawal rate during the period of time of 400 hours from the start of the operation, the condensate withdrawal rate during the period of time of from 400 hours to 600 hours after the start of the operation and the condensate withdrawal rate during the period of time of from 600 hours to 5,000 hours after the start of the operation were 32.95 kg/hr, 32.99 kg/hr and 33 kg/hr, respectively. On the other hand, an evaporation-concentrated liquid containing the catalyst and high boiling point substances was formed in evaporator 14. A portion of the concentrated liquid was led into reboiler 17 through conduits 15 and 16 and recycled into evaporator 14 through conduit 18. The remainder of the concentrated liquid in evaporator 14 was recycled into continuous multi-stage distillation column 1 at a rate of 1 kg/hr through conduits 15, 19 and 3. After the start of the recycling of the concentrated liquid into continuous multi-stage distillation column 1 through conduits 15, 19 and 3, the feeding rate of the mixture of dimethyl carbonate, phenol and catalyst I through conduit 3 into continuous multi-stage distillation column 1 was appropriately controlled according to the recycling rate of the concentrated liquid.

During the period of time of from 400 hours to 5,000 hours after the start of the operation, a portion of the concentrated liquid formed in evaporator 14 was continuously withdrawn through conduit 20 at a rate of 0.05 kg/hr and led into thin-film evaporator 33 thereby forming an evaporated gas. At a point in time of 400 hours after the start of the operation, a sample (of the concentrated liquid withdrawn from evaporator 14) was taken through a sampling nozzle (not shown) provided on conduit 15', and was analyzed to determine the composition of the concentrated liquid by the above-mentioned methods. The concentrated liquid had the following composition: Pb (which is the metal component of catalyst I): 1.3% by weight; the total concentration of high boiling point substances: 1.7% by weight; and 4,4'-dihydroxydiphenyl (which is a high boiling point substance): 0.7% by weight. The evaporated gas formed in thin-film evaporator 33 was continuously withdrawn therefrom through conduit 35 at a rate of 0.04 kg/hr and recycled through conduit 49 into the system for the transesterification. On the other hand, an evaporation-concentrated liquid containing the catalyst and high boiling point substances was continuously withdrawn from the bottom of thin-film evaporator 33 through conduit 34 at a rate of 0.01 kg/hr and led into storage vessel 36. A sample (of the evaporation-concentrated liquid withdrawn from thin-film evaporator 33) was taken through a sampling nozzle (not shown) provided on conduit 34 at a point in time of 400 hours after the start of the operation, and was analyzed to determine the composition of the evaporation-concentrated liquid by the above-mentioned methods. The evaporation-concentrated liquid had the following composition: Pb (which is the metal component of catalyst I): 6.5% by weight; the total concentration of high boiling point substances: 8.6% by weight; and 4,4'-dihydroxydiphenyl (which is a high boiling point substance): 3.6% by weight. At a point in time of 550 hours after the start of the operation, 1 kg of the concentrated liquid stored in storage vessel 36 was withdrawn and led into electric furnace 38 through conduit 37. In electric furnace 38, the concentrated liquid was heated to and maintained at 700° C. for 8 hours while introducing air into electric furnace 38 from conduit 39, to thereby oxidize the concentrated liquid under atmospheric pressure. The resultant oxidation products (i.e., carbon dioxide, water and low boiling point organic compounds) derived from organic matter contained in the concentrated liquid were withdrawn through waste product conduit 40. The oxidation products remaining in electric furnace 38 were allowed to cool and, then, a sample of the remaining oxidation products was taken out from electric furnace 38 and analyzed. By the analysis, only lead monoxide, derived from catalyst I, was detected. This means that, by the oxidative reaction of the concentrated liquid, the organic matter in the concentrated liquid was changed to volatile oxidation products having a low boiling point.

0.07 kg of the oxidation product remaining in electric furnace 38 (i.e., lead monoxide) was charged into reaction vessel 42 provided with distillation column 43 and a jacket (not shown) for circulating a heating medium, and 1.2 kg of phenol was introduced into reaction vessel 42 from conduit 45, to thereby obtain a mixture. The obtained mixture was heated to and maintained at 160° C. (as measured at the heating medium) for 6 hours under atmospheric pressure, thereby performing a reaction. Then, the heating temperature was elevated to 200° C. (as measured at the heating medium) so as to cause both the water formed by the reaction and unreacted phenol to be distilled off from the top of distillation column 43 through conduit 44, wherein the total amount of the water and the unreacted phenol both distilled off was 0.277 kg. A sample was taken from the reaction mixture remaining in reaction vessel 42 and analyzed. The results of the analysis show that the remaining reaction mixture is a solution of lead(II) diphenoxide [Pb(OPh)$_2$] in phenol. 1 kg of the remaining reaction mixture was withdrawn from reaction vessel 42 and transferred through conduit 46 and introduced into storage vessel 47. Thereafter, every 100 hours after the point in time of 550 hours from the start of the operation (i.e., the point in time at which 1 kg of the concentrated liquid was withdrawn from storage vessel 36 and led into electric furnace 38 as mentioned above), a sequence of the above operations using storage vessel 36 (from which 1 kg of the concentrated liquid was withdrawn), electric furnace 38, reaction vessel 42 and storage vessel 47 (into which 1 kg of the remaining reaction mixture obtained in reaction vessel 42 was introduced) was repeated in the same manner as described above. On the other hand, from a point in time of 600 hours after the start of the operation, the reaction mixture stored in storage vessel 47 was continuously withdrawn at a rate of 0.01 kg/hr through conduit 48, and the reaction mixture withdrawn from storage vessel 47 was caused to meet the evaporated gas which was withdrawn from thin-film evaporator 33 and which was led through conduit 35, and the resultant mixture (i.e., a mixture of the products withdrawn through conduits 48 and 35) was recycled into the system for the transesterification through conduit 49. As mentioned above, the condensate withdrawal rate from condenser 22 through conduit 23 during the period of time of from 400 hours to 600 hours after the start of the operation was 32.99 kg/hr, and the condensate withdrawal rate from condenser 22 through conduit 23 during the period of time of from 600 hours to 5,000 hours after the start of the operation was 33 kg/hr. During the period of time of from 400 hours to 600 hours after the start of the operation, catalyst I was added to distillation column 1 through conduit 3 at such a feeding rate as to compensate for the catalyst withdrawal rate at which the catalyst was withdrawn through conduit 20, i.e., catalyst I was added through conduit 3 at a feeding rate such that the above-mentioned Pb concentration of 0.038% by weight in conduit 13 was able to be maintained. The operation was conducted for 5,000 hours. From the point in time of 600 hours after the start of the operation, i.e., from the point in time at which the recycling of the catalyst into the system for the transesterification through conduit 49 was started, there was no need for introducing a fresh catalyst into the system for the transesterification. In addition, since the catalyst-containing liquid containing both the catalyst and high boiling point substances was withdrawn from the system for the transesterification and subjected to the above-described treatments according to the present invention, a waste liquid containing a spent catalyst did not occur at all. From the evaporation-concentrated liquid which was formed in evaporator 14 and which contained the catalyst and high boiling point substances, samples were taken through the above-mentioned sampling nozzle provided on conduit 15', wherein the samples were, respectively, withdrawn at points in time of 1,000 hours, 2,500 hours and 5,000 hours after the start of the operation. The determination of the total concentration of the high boiling point substances in each sample was conducted by the above-mentioned method. With respect to these samples withdrawn at points in time of 1,000 hours, 2,500 hours and 5,000 hours after the start of the operation, the total concentrations of the high boiling point substances were 1.7% by weight, 1.8% by weight and 1.8% by weight, respectively.

During the 5,000 hour operation time, the operation could be stably conducted (for example, both the flow and the composition in each conduit were stable) without suffering disadvantageous phenomena, such as the deposition of the catalyst from a catalyst-containing liquid and the adherence of the deposited catalyst to the inside surfaces associated with the equipment employed for the operation. During the operation, samples of the reaction mixture withdrawn from the bottom of continuous multi-stage distillation column 1 were taken through the above-mentioned sampling nozzle provided on conduit 13, and the samples were analyzed. With respect to the reaction mixture which was taken from conduit 13 at a point in time of 3,000 hours after the start of the operation, the composition of the reaction mixture was as follows: phenol (PhOH): 31% by weight; methyl phenyl carbonate (MPC): 9% by weight; diphenyl carbonate (hereinafter, frequently referred to as "DPC"): 0.5% by weight; anisole (hereinafter, frequently referred to as "ANS"): 0.1% by weight; and Pb: 0.038% by weight. The purity of the aromatic carbonate (which was a mixture of MPC and DPC) in the condensate withdrawn from condenser 22 through conduit 23 was 99.99% or more, and no high boiling point substance was detected in the condensate. After the operation was terminated, the inside surfaces associated with the equipment employed for the operation were examined. No adherence of the catalyst to any of the inner walls of continuous multi-stage distillation column 1, evaporator 14, reboiler 17, conduits and the like was observed.

Comparative Example 1

Substantially the same procedure as in Example 1 was repeated, except that the withdrawal of a portion of the evaporation-concentrated liquid (which was formed in evaporator 14 and which contained the catalyst and high boiling point substances) out of the production system through conduit 20 was not conducted, and the introduction of the fresh catalyst into the system for the transesterification from conduit 3 through preheater 4 and conduit 5 into continuous multi-stage distillation column 1 (which was conducted in Example 1 during the period of time of from 400 hours to 600 hours after the start of the operation) was not conducted. With respect to the samples withdrawn at points in time of 1,000 hours, 2,500 hours and 5,000 hours after the start of the operation, the total concentrations of the high boiling point substances were 5.2% by weight, 14.6% by weight and 32.0% by weight, respectively. With respect to the reaction mixture which was taken from conduit 13 at a point in time of 3,000 hours after the start of the operation, the composition of the reaction mixture was as follows: PhOH: 33% by weight; MPC: 6.5% by weight; DPC: 0.2% by weight; ANS: 0.1% by weight; and Pb: 0.038% by weight. The purity of the aromatic carbonate (which was a mixture of MPC and DPC) in the condensate withdrawn from condenser 22 through conduit 23 was 97%, and the total concentration of the high boiling point substances in the above-mentioned condensate was 1.5% by weight. After the operation was terminated (the operation was conducted for 5,000 hours), the inside surfaces associated with the equipment employed for the operation were examined. The adherence of the catalyst to a part of the inner wall of each of continuous multi-stage distillation column 1, evaporator 14 and the conduits was observed.

Comparative Example 2

Substantially the same procedure as in Example 1 was repeated, except that, after an evaporation-concentrated liquid containing the catalyst and high boiling point substances was withdrawn from the bottom of thin-film evaporator 33, the evaporation-concentrated liquid was introduced into and accumulated in a waste catalyst storage vessel (not shown) instead of leading the evaporation-concentrated liquid to storage vessel 36, so that the sequence of the operations using storage vessel 36, electric furnace 38, reaction vessel 42 and storage vessel 47 was not conducted; and not only during the period of time of from 400 hours to 600 hours after the start of the operation, but also after the point in time of 600 hours after the start of the operation, catalyst I was added to distillation column 1 through conduit 3 at such a feeding rate as to compensate for the catalyst withdrawal rate at which the catalyst was withdrawn through conduit 20, i.e., catalyst I was added through conduit 3 at a feeding rate such that the Pb concentration of 0.038% by weight in conduit 13 was able to be maintained. The operation was conducted for 5,000 hours. During the period of time of from 600 hours to 5,000 hours after the start of the operation, in order to maintain the above-mentioned Pb concentration of 0.038% by weight in conduit 13, it was necessary to add fresh catalyst I to continuous multi-stage distillation column 1 through conduit 3 in an amount as large as 2.86 kg, in terms of the weight of Pb in the catalyst. During the period of time of from 600 hours to 5,000 hours after the start of the operation, the amount of the evaporation-concentrated liquid (containing the catalyst and high boiling point substances) which was withdrawn from the bottom of thin-film evaporator 33 and introduced into and accumulated in the waste catalyst storage vessel reached a level as large as 44 kg.

EXAMPLE 2

Figure 2:
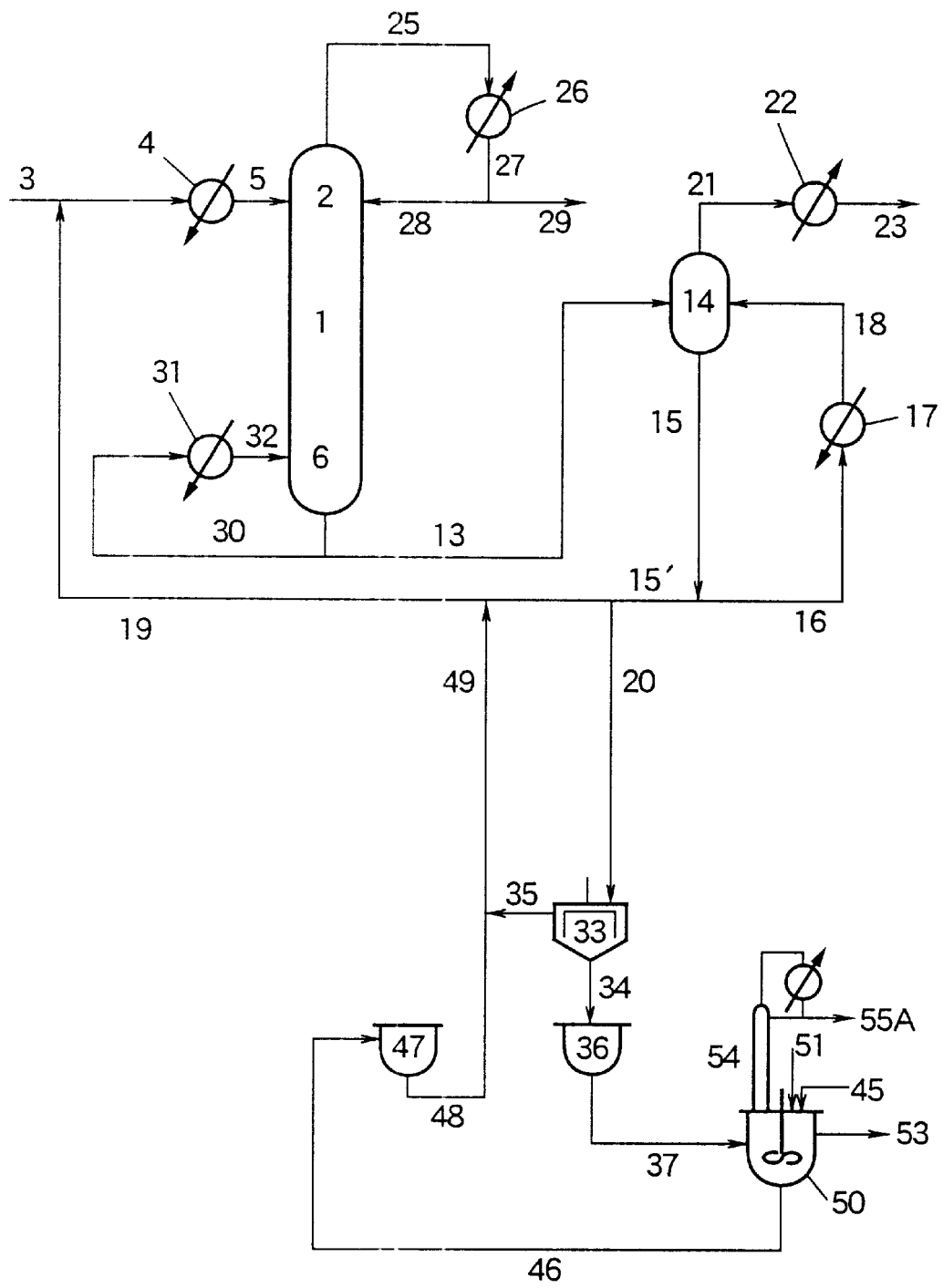
FIG. 2 is a diagram showing another example of systems for practicing the process of the present invention.

The production of diphenyl carbonate (DPC) from methyl phenyl carbonate (MPC) was conducted using catalyst I prepared in Example 1, and the system as shown in FIG. 2, which comprises continuous multi-stage distillation column 1 having a height of 6 m and a diameter of 4 inches and equipped with 20 sieve trays.

A mixture of MPC and catalyst I was continuously fed in liquid form from conduit 3 through preheater 4 and conduit 5 into continuous multi-stage distillation column 1 at a position of 2.0 m below top 2 thereof at a rate of 8 kg/hr, and was allowed to flow down inside multi-stage distillation column 1, thereby performing a reaction. Catalyst I was used in an amount such that the Pb concentration of the reaction mixture in conduit 13 became 0.19% by weight, wherein the Pb concentration can be confirmed using a sample withdrawn through a sampling nozzle (not shown) provided on conduit 13.

The reaction conditions of the above reaction were such that the temperature at the bottom of continuous multistage distillation column 1 was 195° C. and the pressure at the top of continuous multi-stage distillation column 1 was 2.59× $10^4$ Pa. Gas distilled from top 2 of continuous multi-stage distillation column 1 was led through conduit 25 into condenser 26, in which the gas was condensed. A portion of the resultant condensate was recycled into top 2 of continuous multi-stage distillation column 1 through conduits 27 and 28, and the remainder of the condensate was continuously withdrawn at a rate of 2.4 kg/hr through conduits 27 and 29. A portion of the reaction mixture at bottom 6 of continuous multi-stage distillation column 1 was led into reboiler 31 through conduit 30, and recycled into column bottom 6 through conduit 32, and the remainder of the reaction mixture was led into evaporator 14 through conduit 13 at a rate of 7.6 kg/hr. From evaporator 14, an evaporated gas containing DPC was withdrawn and led through conduit 21 into condenser 22, in which the gas was condensed. The resultant condensate was withdrawn from condenser 22 through conduit 23 at a rate of 5.6 kg/hr. On the other hand, an evaporation-concentrated liquid containing the catalyst and high boiling point substances was formed in evaporator 14. A portion of the concentrated liquid was led into reboiler 17 through conduits 15 and 16 and recycled into evaporator 14 through conduit 18. The remainder of the concentrated liquid in evaporator 14 was recycled into continuous multi-stage distillation column 1 through conduits 15, 19 and 3 at a rate of 2 kg/hr. After the start of the recycling of the concentrated liquid into continuous multi-stage distillation column 1 through conduits 15, 19 and 3, the feeding rate of the mixture of MPC and catalyst I through conduit 3 into continuous multi-stage distillation column 1 was appropriately controlled according to the recycling rate of the concentrated liquid.

During the period of time of from 400 hours to 5,000 hours after the start of the operation, a portion of the concentrated liquid formed in evaporator 14 was continuously withdrawn through conduit 20 at a rate of 0.05 kg/hr and led into thin-film evaporator 33. At a point in time of 1,000 hours after the start of the operation, a sample (of the concentrated liquid withdrawn from evaporator 14) was taken through a sampling nozzle (not shown) provided on conduit 15', and was analyzed to determine the composition of the concentrated liquid by the above-mentioned methods. The concentrated liquid had the following composition: Pb (which is the metal component of catalyst I): 0.7% by weight; the total concentration of high boiling point substances: 5.0% by weight; and phenyl salicylate (which is a high boiling point substance): 0.25% by weight. The evaporated gas formed in thin-film evaporator 33 was continuously withdrawn therefrom through conduit 35 at a rate of 0.04 kg/hr and recycled through conduit 49 into the system for the transesterification. On the other hand, an evaporation-concentrated liquid containing the catalyst and high boiling point substances was continuously withdrawn from the bottom of thin-film evaporator 33 through conduit 34 at a rate of 0.01 kg/hr and led into storage vessel 36. A sample (of the evaporation-concentrated liquid withdrawn from thin-film evaporator 33) was taken through a sampling nozzle (not shown) provided on conduit 34 at a point in time of 1,000 hours after the start of the operation, and was analyzed to determine the composition of the evaporation-concentrated liquid by the above-mentioned methods. The evaporation-concentrated liquid had the following composition: Pb (which is the metal component of catalyst I): 3.5% by weight; the total concentration of high boiling point substances: 24.8% by weight; and phenyl salicylate (which is a high boiling point substance): 1.3% by weight.

At a point in time of 550 hours after the start of the operation, 1 kg of the concentrated liquid stored in storage vessel 36 was withdrawn through conduit 37 and led into reaction vessel 50 which had a capacity of 10 liters and which was provided with distillation column 54, a jacket (not shown) for circulating a heating medium, and an agitator. The temperature of reaction vessel 50 was elevated to 180° C. (as measured at the jacket). Then, both a feeding of carbon dioxide into reaction vessel 50 at a flow rate of 3.9 NL/hr [NL means L (liter) as measured under the normal temperature and pressure conditions, namely at 0° C. under 1 atm.] and a feeding of water into reaction vessel 50 at a flow rate of 3.1 g/hr were conducted for 2 hours while stirring, to thereby effect a reaction, thus obtaining a reaction mixture containing lead(II) carbonate as a reaction product. This reaction was conducted under atmospheric pressure. After the lapse of the 2-hour reaction time, the stirring was stopped so as to allow the solids [containing the lead(II) carbonate] in the obtained reaction mixture to be precipitated. After the precipitation, the resultant supernatant in the reaction mixture was withdrawn through conduit 53. The concentration of Pb in the withdrawn supernatant was 400 ppm by weight.

Then, 1.021 kg of PhOH was charged into reaction vessel 50 and stirred at 180° C. (as measured at the jacket) under atmospheric pressure, to thereby effect a reaction. During the reaction, unreacted PhOH was distilled off from the top of distillation column 54 disposed on reaction vessel 50 at a rate of 0.1 kg/hr through conduit 55A. Thus, in reaction vessel 50, a reaction proceeded in which lead(II) carbonate reacts with PhOH to form diphenoxy lead, carbon dioxide and water. The carbon dioxide and water formed in the above reaction were withdrawn from the reaction vessel together with the unreacted PhOH distilled off. A reaction mixture, which remained in reaction vessel 50 after performing the above reaction for 2 hours, was withdrawn from reaction vessel 50 and transferred through conduit 46 and introduced into storage vessel 47.

Thereafter, every 100 hours after the point in time of 550 hours from the start of the operation (i.e., the point in time at which 1 kg of the concentrated liquid was withdrawn from storage vessel 36 and led into reaction vessel 50 as mentioned above), a sequence of the above operations using storage vessel 36 (from which 1 kg of the concentrated liquid was withdrawn), reaction vessel 50 and storage vessel 47 (into which the remaining reaction mixture obtained in reaction vessel 50 was introduced) was repeated in the same manner as described above. On the other hand, from a point in time of 600 hours after the start of the operation, the reaction mixture stored in storage vessel 47 was continuously withdrawn at a rate of 0.01 kg/hr through conduit 48, and the reaction mixture withdrawn from storage vessel 47 was caused to meet the evaporated gas which was withdrawn from thin-film evaporator 33 and which was led through conduit 35, and the resultant mixture (i.e., a mixture of the products withdrawn through conduits 48 and 35) was recycled into the system for the transesterification through conduit 49. The condensate withdrawal rate from condenser 22 through conduit 23 during the period of time of from 400 hours to 600 hours after the start of the operation was 5.55 kg/hr, and the condensate withdrawal rate from condenser 22 through conduit 23 during the period of time of from 600 hours to 5,000 hours after the start of the operation was 5.6 kg/hr. During the period of time of from 400 hours to 600 hours after the start of the operation, catalyst I was added to distillation column 1 through conduit 3 at such a feeding rate as to compensate for the catalyst withdrawal rate at which the catalyst was withdrawn through conduit 20, i.e., catalyst I was added through conduit 3 at a feeding rate such that the above-mentioned Pb concentration of 0.19% by weight in conduit 13 was able to be maintained.

The operation was conducted for 5,000 hours. From the point in time of 600 hours after the start of the operation, i.e., from the point in time at which the recycling of the catalyst into the system for the transesterification through conduit 49 was started, the feeding rate of catalyst I into the system for the transesterification through conduit 3 was as small as 0.0033 g/hr, in terms of the weight of Pb contained in catalyst I. Further, during the operation, the above-mentioned supernatant (containing Pb) withdrawn from reaction vessel 50 through conduit 53 was subjected to burning to thereby obtain lead monoxide and the obtained lead monoxide was used for producing catalyst I. The amount of catalyst I which was prepared from the thus obtained lead monoxide (recovered Pb) was sufficient to be used as catalyst I which was to be introduced in an amount as small as 0.0033 g/hr through conduit 3 (from the point in time of 600 hours after the start of the operation, i.e., from the point in time at which the recycling of the catalyst into the system for the transesterification through conduit 49 was started). Therefore, from the point in time of 600 hours after the start of the operation, all need for the catalyst was met by both the recycled catalyst and the catalyst prepared from the Pb recovered from the supernatant withdrawn from reaction vessel 50.

In addition, as mentioned above, the supernatant withdrawn from reaction vessel 50 was subjected to burning to obtain lead monoxide, and the obtained lead monoxide was recovered and used for preparing catalyst I. Therefore, a waste liquid containing a spent catalyst did not occur at all.

From the evaporation-concentrated liquid which was formed in evaporator 14 and which contained the catalyst and high boiling point substances, samples were taken through a sampling nozzle provided on conduit 15', wherein the samples were, respectively, withdrawn at points in time of 1,000 hours, 2,500 hours and 5,000 hours after the start of the operation. The determination of the total concentration of the high boiling point substances in each sample was conducted by the above-mentioned method. With respect to these samples withdrawn at points in time of 1,000 hours, 2,500 hours and 5,000 hours after the start of the operation, the total concentrations of the high boiling point substances were 5.0% by weight, 5.1% by weight and 5.1% by weight, respectively, and the phenyl salicylate concentrations were 0.25% by weight, 0.25% by weight and 0.26% by weight, respectively.

During the 5,000 hour operation time, the operation could be stably conducted (for example, both the flow and the composition in each conduit were stable) without suffering disadvantageous phenomena, such as the deposition of the catalyst from a catalyst-containing liquid and the adherence of the deposited catalyst to the inside surfaces associated with the equipment employed for the operation. During the operation, samples of the reaction mixture withdrawn from the bottom of continuous multi-stage distillation column 1 were taken through the above-mentioned sampling nozzle provided on conduit 13, and the samples were analyzed. With respect to the reaction mixture which was taken from conduit 13 at a point in time of 3,000 hours after the start of the operation, the composition of the reaction mixture was as follows: MPC: 23.8% by weight; DPC: 74.6% by weight; and Pb: 0.19% by weight. The purity of the aromatic carbonate (which was a mixture of MPC and DPC) in the condensate withdrawn from condenser 22 through conduit 23 was 99.99% or more, and no high boiling point substance was detected in the condensate. After the operation was terminated, the inside surfaces associated with the equipment employed for the operation were examined. No adherence of the catalyst to any of the inner walls of continuous multi-stage distillation column 1, evaporator 14, reboiler 17, conduits and the like was observed.

Comparative Example 3

Substantially the same procedure as in Example 2 was repeated, except that, after an evaporation-concentrated liquid containing the catalyst and high boiling point substances was withdrawn from the bottom of thin-film evaporator 33, the evaporation-concentrated liquid was introduced into and accumulated in a waste catalyst storage vessel (not shown) instead of leading the evaporation-concentrated liquid to storage vessel 36, so that the sequence of the operations using storage vessel 36, electric furnace 38, reaction vessel 42 and storage vessel 47 was not conducted; and not only during the period of time of from 400 hours to 600 hours after the start of the operation, but also after the point in time of 600 hours after the start of the operation, catalyst I was added to distillation column 1 through conduit 3 at such a feeding rate as to compensate for the catalyst withdrawal rate at which the catalyst was withdrawn through conduit 20, i.e., catalyst I was added through conduit 3 at a feeding rate such that the Pb concentration of 0.19% by weight in conduit 13 was able to be maintained. The operation was conducted for 5,000 hours. During the period of time of from 600 hours to 5,000 hours after the start of the operation, in order to maintain the above-mentioned Pb concentration of 0.19% by weight in conduit 13, it was necessary to add fresh catalyst I to continuous multi-stage distillation column 1 through conduit 3 in an amount as large as 1.54 kg, in terms of the weight of Pb in the catalyst. During the period of time of from 600 hours to 5,000 hours after the start of the operation, the amount of the evaporation-concentrated liquid (containing the catalyst and high boiling point substances)

which was withdrawn from the bottom of thin-film evaporator 33 and introduced into and accumulated in the waste catalyst storage vessel reached a level as large as 44 kg.

EXAMPLE 3

Figure 3:
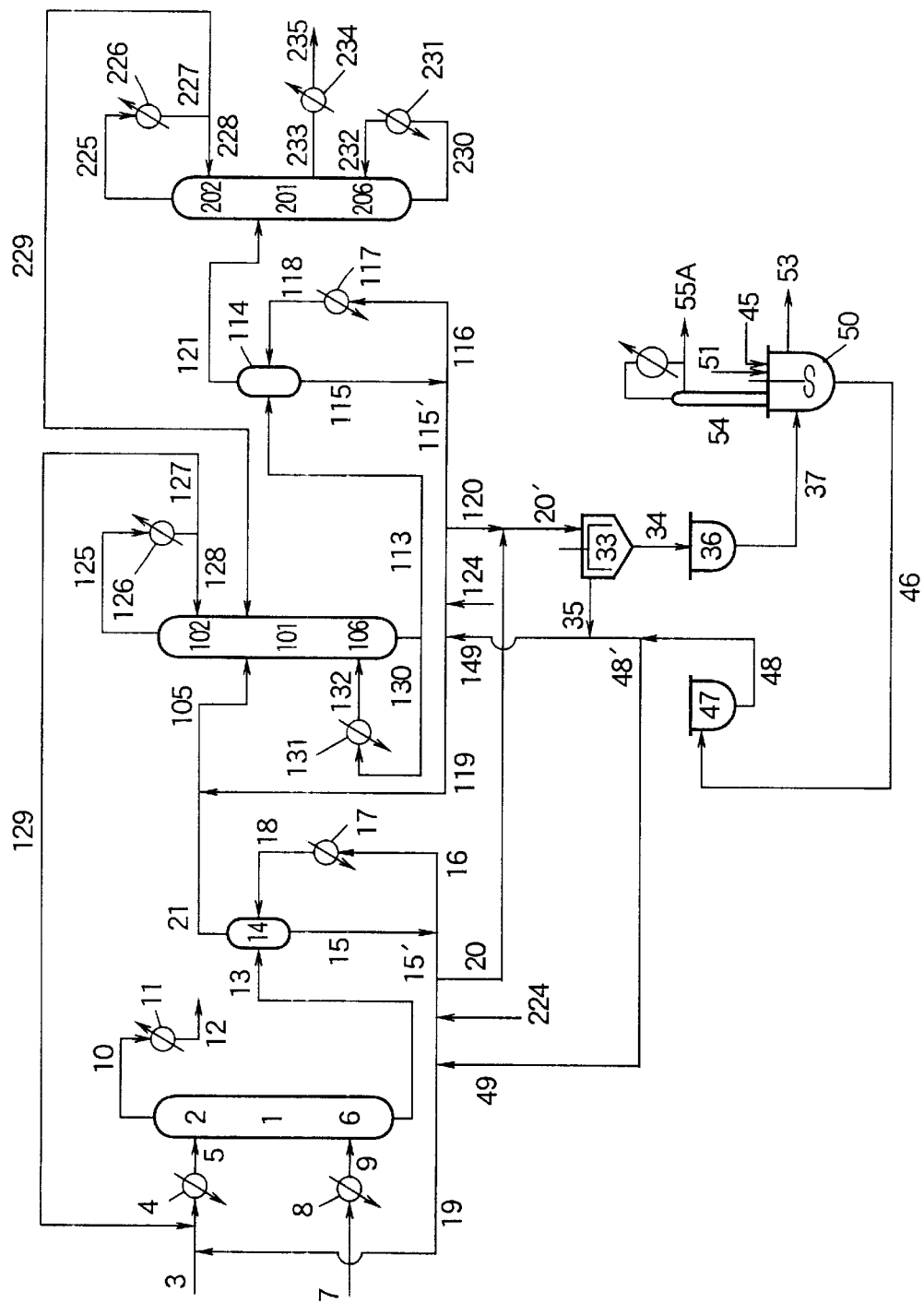
FIG. 3 is a diagram showing a further example of systems for practicing the process of the present invention.

The production of diphenyl carbonate was conducted using catalyst I prepared in Example 1, and the system as shown in FIG. 3.

A mixture of dimethyl carbonate, PhOH (which contains, as an impurity, 200 ppm by weight of 4,4'-dihydroxydiphenyl which is a high boiling point substance) and methyl phenyl carbonate was continuously fed in liquid form from conduit 3 through preheater 4 and conduit 5 into continuous multi-stage distillation column 1 at a position of 0.5 m below the top 2 thereof (which column was comprised of a plate column having a height of 12 m and a diameter of 8 inches and provided with 40 sieve trays) at a rate of 31 kg/hr, thereby allowing the mixture to flow down inside continuous multi-stage distillation column 1 so as to perform a reaction. The composition of the mixture fed from conduit 3 was so controlled that the mixture flowing through conduit 5 during the operation (the mixture flowing through conduit 5 was comprised of a liquid introduced from conduit 19, which was recycled from evaporator 14; a liquid introduced from conduit 129, which was recycled from continuous multi-stage distillation column 101; and the above-mentioned mixture fed from conduit 3) had a composition of 49.9% by weight of DMC, 44.7% by weight of PhOH and 4.9% by weight of MPC. DMC was fed through conduit 7 to evaporator 8, in which the DMC was subjected to evaporation. The resultant gas was fed to bottom 6 of continuous multi-stage distillation column 1 through conduit 9 at a rate of 55 kg/hr. Catalyst I was fed from conduit 224 in such an amount that the Pb concentration at conduit 13 became 0.042% by weight, wherein the Pb concentration can be confirmed using a sample withdrawn from a sampling nozzle (not shown) provided on conduit 13. Continuous multi-stage distillation column 1 was operated under conditions such that the temperature at the column bottom was 203° C. and the pressure at the column top was $7.4 \times 10^5$ Pa. Continuous multi-stage distillation column 1 was clad with a heat insulating material and a part of the column was heated by a heater (not shown). Gas distilled from top 2 of the column was led through conduit 10 into condenser 11, in which the gas was condensed. The resultant condensate was continuously withdrawn at a rate of 55 kg/hr from conduit 12. A reaction mixture was withdrawn continuously from bottom 6 at a rate of 31 kg/hr, and was led to evaporator 14 through conduit 13. In evaporator 14, an evaporation-concentrated liquid containing the catalyst and high boiling point substances was formed. A portion of the concentrated liquid was led into reboiler 17 through conduits 15 and 16 and recycled into evaporator 14 through conduit 18. The remainder of the concentrated liquid in evaporator 14 was recycled into continuous multi-stage distillation column 1 at a rate of 1 kg/hr through conduits 15, 19 and 3. During the period of time from 400 hours to 5,000 hours after the start of the operation, a portion of the concentrated liquid formed in evaporator 14 was continuously withdrawn from conduit 20 at a rate of 0.05 kg/hr and introduced into thin-film evaporator 33.

Catalyst I was fed from conduit 224 at such a feeding rate as to compensate for the catalyst withdrawal rate at which the catalyst was withdrawn through conduit 20, i.e., catalyst I was fed from conduit 224 at a feeding rate such that the above-mentioned Pb concentration of 0.042% by weight in conduit 13 was able to be maintained. On the other hand, an evaporated gas formed in evaporator 14 was fed through conduits 21 and 105 into continuous multi-stage distillation column 101 at a position of 2.0 m below top 102 thereof, which column was comprised of a plate column having a height of 6 m and a diameter of 10 inches and provided with 20 sieve trays, thereby performing a reaction. The composition of the mixture in conduit 105 was as follows: DMC: 43.1% by weight; PhOH: 24.5% by weight; MPC: 27.1% by weight; and DPC: 4.5% by weight (the mixture in conduit 105 was comprised of a gas introduced through conduit 21 and a liquid introduced from conduit 119, which was recycled from evaporator 114). Catalyst I was fed from conduit 124 in such an amount that the Pb concentration at conduit 113 became 0.16% by weight, wherein the Pb concentration can be confirmed using a sample withdrawn from a sampling nozzle (not shown) provided on conduit 113. Continuous multi-stage distillation column 101 was operated under conditions such that the temperature at the column bottom was 198° C. and the pressure at the column top was $3.7 \times 10^4$ Pa. Gas distilled from column top 102 was led through conduit 125 to condenser 126, in which the gas was condensed. A portion of the resultant condensate was recycled into column top 102 through conduit 128, and the remainder of the condensate was recycled into continuous multi-stage distillation column 1 through conduits 127 and 129, preheater 4 and conduit 5. After the start of the recycling of the condensate into continuous multi-stage distillation column 1 through conduit 129, PhOH (containing 200 ppm by weight of 4,4'-dihydroxydiphenyl which is a high boiling point substance) was added to the mixture fed from conduit 3 in such an amount that the above-mentioned composition of the mixture at conduit 5 can be maintained. A portion of the reaction mixture at bottom 106 of continuous multi-stage distillation column 101 was led into reboiler 131 through conduit 130, and recycled into column bottom 106 through conduit 132, and the remainder of the reaction mixture was led to evaporator 114 through conduit 113 at a rate of 8.8 kg/hr. In evaporator 114, an evaporation-concentrated liquid containing the catalyst and high boiling point substances was formed. A portion of the concentrated liquid was led into reboiler 117 through conduits 115 and 116 and recycled into evaporator 114 through conduit 118. The remainder of the concentrated liquid in evaporator 114 was recycled into continuous multi-stage distillation column 101 through conduits 115, 119 and 105 at a rate of 2 kg/hr. During the period of time of from 400 hours to 5,000 hours after the start of the operation, a portion of the concentrated liquid formed in evaporator 114 was continuously withdrawn at a rate of 0.05 kg/hr from the system for the transesterification through conduit 120, and was caused to meet the concentrated liquid led through conduit 20. The resultant liquid mixture (i.e., a mixture of the liquid products withdrawn from the system for the transesterification through conduits 120 and 20) was led into thin-film evaporator 33 through conduit 20'. At a point in time of 1,000 hours after the start of the operation, a sample (of the above-mentioned liquid mixture) was taken through a sampling nozzle (not shown) provided on conduit 20', and was analyzed to determine the composition of the liquid mixture by the above-mentioned methods. The liquid mixture had the following composition: Pb (which is the metal component of catalyst I): 1.0% by weight; the total concentration of high boiling point substances: 3.3% by weight; 4,4'-dihydroxydiphenyl (which is a high boiling point substance): 1.8% by weight; and phenyl salicylate: 0.13% by weight. The evaporated gas formed in thin-film evaporator 33 was continuously withdrawn therefrom through conduit 35 at a rate of 0.09 kg/hr and recycled through conduit 149 into the system for the transesterification. On the other hand, an evaporation-concentrated liquid containing the catalyst and high boiling point substances was continuously withdrawn from the bottom of thin-film evaporator 33 through conduit 34 at a rate of 0.01 kg/hr and led into storage vessel 36. A sample (of the evaporation-concentrated liquid withdrawn from thin-film evaporator 33) was taken through a sampling nozzle (not shown) provided on conduit 34 at a point in time of 1,000 hours after the start of the operation, and was analyzed to determine the composition of the evaporation-concentrated liquid by the above-mentioned methods. The evaporation-concentrated liquid had the following composition: Pb (which is the metal component of catalyst I): 9.9% by weight; the total concentration of high boiling point substances: 33.4% by weight; 4,4'-dihydroxydiphenyl (which is a high boiling point substance): 3.7% by weight; and phenyl salicylate: 1.3% by weight.

At a point in time of 550 hours after the start of the operation, 1 kg of the concentrated liquid stored in storage vessel 36 was withdrawn through conduit 37 and led into reaction vessel 50 which had a capacity of 10 liters and which was provided with distillation column 54, a jacket (not shown) for circulating a heating medium, and an agitator. The temperature of reaction vessel 50 was elevated to 180° C. (as measured at the jacket). Then, both a feeding of carbon dioxide into reaction vessel 50 at a flow rate of 11 NL/hr and a feeding of water into reaction vessel 50 at a flow rate of 8.7 g/hr were conducted for 2 hours while stirring, to thereby effect a reaction, thus obtaining a reaction mixture containing lead(II) carbonate as a reaction product. This reaction was conducted under atmospheric pressure. After the lapse of the 2-hour reaction time, the stirring was stopped so as to allow the solids [containing the lead(II) carbonate] in the obtained reaction mixture to be precipitated. After the precipitation, the resultant supernatant in the reaction mixture was withdrawn through conduit 53. The concentration of Pb in the withdrawn supernatant was 400 ppm by weight.

Then, 0.620 kg of PhOH was charged into reaction vessel 50 and stirred at 180° C. (as measured at the jacket) under atmospheric pressure, to thereby effect a reaction. During the reaction, unreacted PhOH was distilled off from the top of distillation column 54 disposed on reaction vessel 50 at a rate of 0.1 kg/hr through conduit 55A. Thus, in reaction vessel 50, in the same manner as in Example 2, a reaction proceeded in which lead(II) carbonate reacts with PhOH to form diphenoxy lead, carbon dioxide and water. The carbon dioxide and water formed in the above reaction were withdrawn from the reaction vessel together with the unreacted PhOH distilled off. A reaction mixture, which remained in reaction vessel 50 after performing the above reaction for 2 hours, was withdrawn from reaction vessel 50 and transferred through conduit 46 and introduced into storage vessel 47.

Thereafter, every 100 hours after the point in time of 550 hours from the start of the operation (i.e., the point in time at which 1 kg of the concentrated liquid was withdrawn from storage vessel 36 and led into reaction vessel 50 as mentioned above), a sequence of the above operations using storage vessel 36 (from which 1 kg of the concentrated liquid was withdrawn), reaction vessel 50 and storage vessel 47 (into which the remaining reaction mixture obtained in reaction vessel 50 was introduced) was repeated in the same manner as described above. On the other hand, from a point in time of 600 hours after the start of the operation, the reaction mixture stored in storage vessel 47 was continuously withdrawn at a rate of 0.01 kg/hr through conduit 48. A portion of the reaction mixture withdrawn from storage vessel 47 was recycled into the system for the transesterification through conduit 49 at a rate of 0.0065 kg/hr. The remainder of the reaction mixture withdrawn from storage vessel 47 was led through conduit 48' at a rate of 0.0035 kg/hr and caused to meet the evaporated gas which was withdrawn from thin-film evaporator 33 and which was led through conduit 35, and the resultant mixture (i.e., a mixture of the products withdrawn through conduits 48'and 35) was recycled into the system for the transesterification through conduit 149.

During the period of time of from 400 hours to 600 hours after the start of the operation, catalyst I was added to distillation column 1 through conduit 224 and to distillation column 101 through conduit 124 both at such a feeding rate as to compensate for the catalyst withdrawal rate at which the catalyst was withdrawn through conduits 20 and 120, i.e., catalyst I was added through conduits 224 and 124 both at a feeding rate such that both of the above-mentioned Pb concentration of 0.042% by weight in conduit 13 and the above-mentioned Pb concentration of 0.16% by weight in conduit 113 were able to be maintained. An evaporated gas formed in evaporator 114 was fed through conduit 121 into continuous multi-stage distillation column 201 at a position of 2.0 m below top 202 thereof, which column was comprised of a plate column having a height of 6 m and a diameter of 6 inches and provided with 20 sieve trays, thereby separating DPC from the fed gas. Continuous multi-stage distillation column 201 was operated under conditions such that the temperature at the column bottom was 184° C. and the pressure at the column and top was $2 \times 10^3$ Pa. Gas distilled from top 202 of the column was led through conduit 225 to condenser 226, in which the gas was condensed. A portion of the resultant condensate was recycled into top 202 of the column through conduit 228, and the remainder of the condensate was recycled into continuous multi-stage distillation column 101 through conduits 227 and 229. A gas was withdrawn from continuous multi-stage distillation column 201 through conduit 233 provided at a position of 4.0 m below column top 202 and was led to condenser 234, in which the withdrawn gas was condensed. The resultant condensate was withdrawn at a rate of 6.7 kg/hr through conduit 235.

The operation was conducted for 5,000 hours. From the point in time of 600 hours after the start of the operation, i.e., from the point in time at which the recycling of the catalyst into the system for the transesterification through conduits 49 and 149 was started, the total feeding rate of catalyst I into the system for the transesterification through conduits 124 and 224 was as small as 0.0032 g/hr, in terms of the weight of Pb contained in catalyst I. Further, during the operation, the above-mentioned supernatant (containing Pb) withdrawn from reaction vessel 50 through conduit 53 was subjected to burning to thereby obtain lead monoxide and the obtained lead monoxide was used for producing catalyst I. The amount of catalyst I which was prepared from the thus obtained lead monoxide (recovered Pb) was sufficient to be used as catalyst I which was to be introduced in the above-mentioned amount of 0.0032 g/hr through conduits 124 and 224 (from the point in time of 600 hours after the start of the operation, i.e., from the point in time at which the recycling of the catalyst into the system for the transesterification through conduits 49 and 149 was started). Therefore, from the point in time of 600 hours after the start of the operation, all need for the catalyst was met by both the recycled catalyst and the catalyst prepared from the Pb recovered from the supernatant withdrawn from reaction vessel 50.

In addition, as mentioned above, the supernatant withdrawn from reaction vessel 50 was subjected to burning to obtain lead monoxide, and the obtained lead monoxide was recovered and used for preparing catalyst I. Therefore, a waste liquid containing a spent catalyst did not occur at all.

From the evaporation-concentrated liquid which was formed in evaporator 14 and which contained the catalyst and high boiling point substances, samples were taken through a sampling nozzle provided on conduit 15', wherein the samples were, respectively, withdrawn at points in time of 1,000 hours, 2,500 hours and 5,000 hours after the start of the operation. The determination of the total concentration of the high boiling point substances in each sample was conducted by the above-mentioned method. With respect to these samples withdrawn at points in time of 1,000 hours, 2,500 hours and 5,000 hours after the start of the operation, the total concentrations of the high boiling point substances were 2.2% by weight, 2.3% by weight and 2.3% by weight, respectively. Further, from the evaporation-concentrated liquid which was formed in evaporator 114 and which contained the catalyst and high boiling point substances, samples were taken through a sampling nozzle provided on conduit 115', wherein the samples were, respectively, withdrawn at points in time of 1,000 hours, 2,500 hours and 5,000 hours after the start of the operation. With respect to these samples withdrawn at points in time of 1,000 hours, 2,500 hours and 5,000 hours after the start of the operation, the total concentrations of the high boiling point substances were 5.0% by weight, 5.1% by weight and 5.1% by weight, respectively, and the phenyl salicylate concentrations were 0.25% by weight, 0.26% by weight and 0.26% by weight, respectively.

During the 5,000 hour operation time, the operation could be stably conducted (for example, both the flow and the composition in each conduit were stable) without suffering disadvantageous phenomena, such as the deposition of the catalyst from a catalyst-containing liquid and the adherence of the deposited catalyst to the inside surfaces associated with the equipment employed for the operation. At a point in time of 3,000 hours after the start of the operation, the purity of the aromatic carbonate (which was DPC) in the condensate withdrawn from condenser 234 through conduit 235 was 99.99% or more, and no substance other than DPC was detected in the condensate. After the operation was terminated, the inside surfaces associated with the equipment employed for the operation were examined. No adherence of the catalyst to any of the inner walls of continuous multi-stage distillation column 1, evaporator 14, reboiler 17, conduits and the like was observed.

Comparative Example 4

Substantially the same procedure as in Example 3 was repeated, except that, with respect to the evaporation-concentrated liquid (containing the catalyst and high boiling point substances) which was formed in evaporator 14 and the evaporation-concentrated liquid (containing the catalyst and high boiling point substances) which was formed in evaporator 114, the withdrawal of a portion of each of these evaporation-concentrated liquids out of the production system through conduits 20 and 120 was not conducted, and that the introduction of the fresh catalyst into the system for the transesterification from conduits 224 and 124 into continuous multi-stage distillation columns 1 and 101 (which was conducted in Example 3 during the period of time of from 400 hours to 5,000 hours after the start of the operation) was not conducted. With respect to the samples withdrawn through the sampling nozzle provided on conduit 115' at points in time of 1,000 hours, 2,500 hours and 5,000 hours after the start of the operation, the total concentrations of the high boiling point substances were 12.5% by weight, 30.4% by weight and 52.3% by weight, respectively, and the phenyl salicylate concentrations were 0.62% by weight, 1.7% by weight and 2.9% by weight, respectively.

With respect to the aromatic carbonate (which was DPC) in the condensate withdrawn from condenser 234 through conduit 235 at a point in time of 3,000 hours after the start of the operation, the purity thereof was 98.7%. Further, the concentration of phenyl salicylate in the above-mentioned condensate was 12 ppm by weight, and the total concentration of the high boiling point substances in the above-mentioned condensate was 0.06% by weight. The operation was conducted for 5,000 hours. After the operation was terminated, the inside surfaces associated with the equipment employed for the operation were examined. The adherence of the catalyst to a part of the inner wall of each of continuous multi-stage distillation column 1, evaporator 14 and the conduits was observed.

EXAMPLE 4

Figure 4:
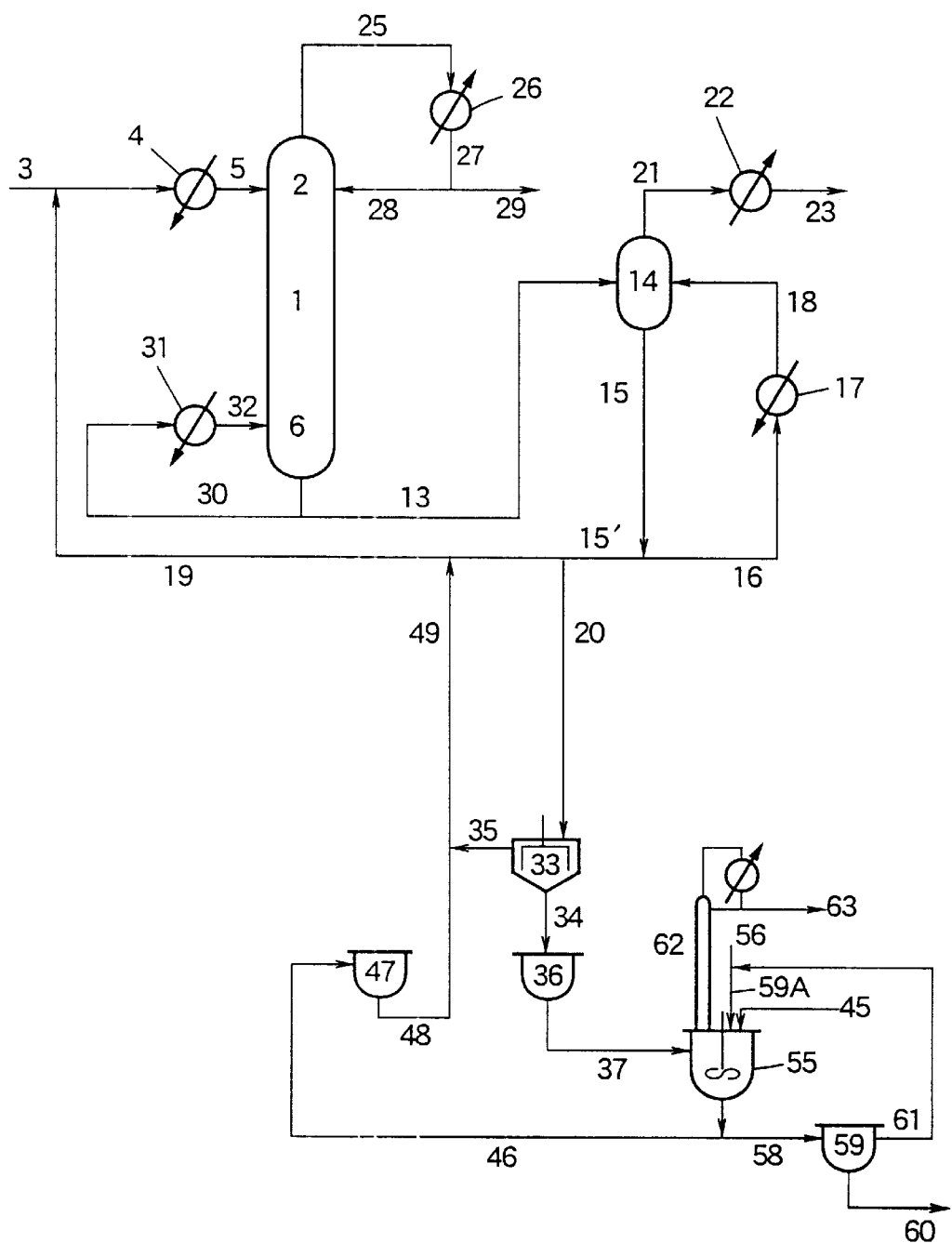
FIG. 4 is a diagram showing still a further example of systems for practicing the process of the present invention.

The production of an aromatic carbonate was conducted in substantially the same manner as in Example 2, except that the system as shown in FIG. 4 was used instead of the system as shown in FIG. 2. As shown in FIGS. 4 and 2, the difference between the system as shown in FIG. 4 and the system as shown in FIG. 2 resides in the region into which the concentrated liquid stored in storage vessel 36 is introduced through conduit 37 and from which a reaction mixture obtained from the above concentrated liquid is transferred to storage vessel 47 through conduit 46.

During the period of time of 400 hours to 5,000 hours after the start of the operation, a portion of the concentrated liquid formed in evaporator 14 was continuously withdrawn through conduit 20 at a rate of 0.05 kg/hr and led into thin-film evaporator 33. At a point in time of 1,000 hours after the start of the operation, a sample (of the concentrated liquid withdrawn from evaporator 14) was taken through a sampling nozzle (not shown) provided on conduit 15', and was analyzed to determine the composition of the concentrated liquid by the above-mentioned methods. The concentrated liquid had the following composition: Pb (which is the metal component of catalyst I): 0.7% by weight; the total concentration of high boiling point substances: 4.0% by weight; and phenyl salicylate (which is a high boiling point substance): 0.15% by weight. The evaporated gas formed in thin-film evaporator 33 was continuously withdrawn therefrom through conduit 35 at a rate of 0.04 kg/hr and recycled through conduit 49 into the system for the transesterification. On the other hand, an evaporation-concentrated liquid containing the catalyst and high boiling point substances was continuously withdrawn from the bottom of thin-film evaporator 33 through conduit 34 at a rate of 0.01 kg/hr and led into storage vessel 36. A sample (of the evaporation-concentrated liquid withdrawn from thin-film evaporator 33) was taken through a sampling nozzle (not shown) provided on conduit 34 at a point in time of 1,000 hours after the start of the operation, and was analyzed to determine the composition of the evaporation-concentrated liquid by the above-mentioned methods. The evaporation-concentrated liquid had the following composition: Pb (which is the metal component of catalyst I): 3.5% by weight; the total concentration of high boiling point substances: 19.8% by weight; and phenyl salicylate (which is a high boiling point substance): 0.75% by weight.

At a point in time of 550 hours after the start of the reaction, 1 kg of the concentrated liquid stored in storage vessel 36 was withdrawn through conduit 37 and led into reaction vessel 55 which had a capacity of 10 liters and which was provided with distillation column 62, a jacket (not shown) for circulating a heating medium, and an agitator. 5 kg of water was introduced into reaction vessel 55, and the temperature of reaction vessel 55 was elevated to and maintained at 200° C. (as measured at the jacket) while stirring. The internal pressure of reaction vessel 55 rose to $3.0 \times 10^6$ Pa. After continuing the stirring at 200° C. for 4 hours, the stirring was stopped, and the temperature of reaction vessel 55 (as measured at the jacket) was lowered to 100° C. and allowed to stand for 1 hour. The internal pressure of reaction vessel 55 was lowered to atmospheric pressure by discharging gas from reaction vessel 55 through conduit 63. From the resultant reaction mixture in reaction vessel 55, a liquid phase was withdrawn and led to storage vessel 59 through conduit 58, leaving a white precipitate in reaction vessel 55. The white precipitate left in reaction vessel 55 was analyzed, and the results of the analysis showed that the white precipitate was a solid comprised mainly of lead(II) carbonate. On the other hand, when the liquid phase introduced into storage vessel 59 was allowed to cool to room temperature, it was separated into upper and lower liquid layers. The upper layer had the following composition: water: 93.5% by weight; PhOH: 6.5% by weight; and no high boiling point substance was detected. The lower layer had the following composition: PhOH: 57.3% by weight; the total concentration of high boiling point substances: 14.3% by weight; Pb: 100 ppm by weight; and phenyl salicylate was not detected at all. From the mass balance of PhOH, phenyl salicylate and high boiling point substances, it was found that phenyl salicylate had been converted into PhOH by hydrolysis and decarboxylation. The lower layer in storage vessel 59 was withdrawn therefrom through conduit 60. The weight of the lower layer withdrawn from storage vessel 59 was 603 g. The lead(II) carbonate in reaction vessel 55 was converted into diphenoxy lead in substantially the same manner as in Example 2, i.e., by a method in which PhOH is introduced into reaction vessel 55 through conduits 56 and 59A, and the resultant mixture in reaction vessel 55 is subjected to a reaction while stirring at 180° C. (as measured at the jacket) and distilling off by-produced water and carbon dioxide together with unreacted PhOH. 1 kg of a reaction mixture, which remained in reaction vessel 55 after performing the above reaction for 2 hours, was withdrawn from reaction vessel 55 and transferred through conduit 46 and introduced into storage vessel 47.

Thereafter, every 100 hours after the point in time of 550 hours from the start of the operation (i.e., the point in time at which 1 kg of the concentrated liquid was withdrawn from storage vessel 36 and led into reaction vessel 55 as mentioned above), a sequence of the above operations using storage vessel 36 (from which 1 kg of the concentrated liquid was withdrawn), reaction vessel 55, storage vessel 59 and storage vessel 47 (into which 1 kg of the remaining reaction mixture obtained in reaction vessel 55 was introduced) was repeated in the same manner as described above. With respect to each of the second-time to last-time practices of the above-mentioned sequence of the operations using storage vessel 36, reaction vessel 55, storage vessel 59 and storage vessel 47, as the 5 kg of water which is introduced into reaction vessel 55 (so as to be mixed with 1 kg of the concentrated liquid transferred from storage vessel 36), use was made of an aqueous mixture obtained by a method in which the above-mentioned upper layer obtained in storage vessel 59 is taken out and water is added thereto in an amount such that the weight of the resultant aqueous mixture becomes 5 kg.

On the other hand, from a point in time of 600 hours after the start of the operation, the reaction mixture stored in storage vessel 47 was continuously withdrawn at a rate of 0.01 kg/hr through conduit 48, and the reaction mixture withdrawn from storage vessel 47 was caused to meet the evaporated gas which was withdrawn from thin-film evaporator 33 and which was led through conduit 35, and the resultant mixture (i.e., a mixture of the products withdrawn through conduits 48 and 35) was recycled into the system for the transesterification through conduit 49.

The condensate withdrawal rate from condenser 22 through conduit 23 during the period of time of from 400 hours to 600 hours after the start of the operation was 5.55 kg/hr, and the condensate withdrawal rate from condenser 22 through conduit 23 during the period of time of from 600 hours to 5,000 hours after the start of the operation was 5.6 kg/hr. During the period of time of from 400 hours to 600 hours after the start of the operation, catalyst I was added to distillation column 1 through conduit 3 at such a feeding rate as to compensate for the catalyst withdrawal rate at which the catalyst was withdrawn through conduit 20, i.e., catalyst I was added through conduit 3 at a feeding rate such that the Pb concentration of 0.19% by weight in conduit 13 was able to be maintained.

The operation was conducted for 5,000 hours. From the point in time of 600 hours after the start of the operation, i.e., from the point in time at which the recycling of the catalyst into the system for the transesterification through conduit 49 was started, the feeding rate of catalyst I into the system for the transesterification through conduit 3 was as small as 0.0006 g/hr, in terms of the weight of Pb contained in catalyst I. Further, during the operation, the above-mentioned lower layer (containing Pb) withdrawn from storage vessel 59 through conduit 60 was subjected to burning to thereby obtain lead monoxide and the obtained lead monoxide was used for producing catalyst I. The amount of catalyst I which was prepared from the thus obtained lead monoxide (recovered Pb) was sufficient to be used as catalyst I which was to be introduced in an amount as small as 0.0006 g/hr through conduit 3 (from the point in time of 600 hours after the start of the operation, i.e., from the point in time at which the recycling of the catalyst into the system for the transesterification through conduit 49 was started). Therefore, from the point in time of 600 hours after the start of the operation, all need for the catalyst was met by both the recycled catalyst and the catalyst prepared from the Pb recovered from the lower layer withdrawn from storage vessel 59 (wherein the lower layer withdrawn from storage vessel 59 is a portion of the liquid phase withdrawn from reaction vessel 55).

In addition, as mentioned above, the lower layer withdrawn from storage vessel 59 through conduit 60 was subjected to burning to obtain lead monoxide, and the obtained lead monoxide was recovered and used for preparing catalyst I. Therefore, a waste liquid containing a spent catalyst did not occur at all.

From the evaporation-concentrated liquid which was formed in evaporator 14 and which contained the catalyst and high boiling point substances, samples were taken through a sampling nozzle provided on conduit 15', wherein the samples were, respectively, withdrawn at points in time of 1,000 hours, 2,500 hours and 5,000 hours after the start of the operation. The determination of the total concentration of the high boiling point substances in each sample was conducted by the above-mentioned method. With respect to these samples withdrawn at points in time of 1,000 hours, 2,500 hours and 5,000 hours after the start of the operation, the total concentrations of the high boiling point substances were 4.0% by weight, 4.1% by weight and 4.1% by weight, respectively.

During the 5,000 hour operation time, the operation could be stably conducted (for example, both the flow and the composition in each conduit were stable) without suffering disadvantageous phenomena, such as the deposition of the catalyst from a catalyst-containing liquid and the adherence of the deposited catalyst to the inside surfaces associated with the equipment employed for the operation. During the operation, samples of the reaction mixture withdrawn from the bottom of continuous multi-stage distillation column 1 were taken through the sampling nozzle provided on conduit 13, and the samples were analyzed. With respect to the reaction mixture which was taken from conduit 13 at a point in time of 3,000 hours after the start of the operation, the composition of the reaction mixture was as follows: MPC: 23.9% by weight; DPC: 74.8% by weight; and Pb: 0.19% by weight. The purity of the aromatic carbonate (which was a mixture of MPC and DPC) in the condensate withdrawn from condenser 22 through conduit 23 was 99.99% or more, and no high boiling point substance was detected in the condensate. After the operation was terminated, the inside surfaces associated with the equipment employed for the operation were examined. No adherence of the catalyst to any of the inner walls of continuous multi-stage distillation column 1, evaporator 14, reboiler 17, conduits and the like was observed.

EXAMPLE 5

Preparation of Catalyst

A mixture of 30 kg of PhOH, 10 kg of methyl phenyl carbonate and 8 kg of dibutyltin oxide was heated to and maintained at 180° C. for 10 hours, there-by performing a reaction. After that period of time, water formed in the resultant reaction mixture was distilled off together with unreacted PhOH. Then, most of the remaining PhOH and methyl phenyl carbonate were distilled off from the reaction mixture under reduced pressure, and the resultant mixture was allowed to cool in a nitrogen atmosphere, to thereby obtain catalyst II.

Production of Aromatic Carbonate

Figure 5:
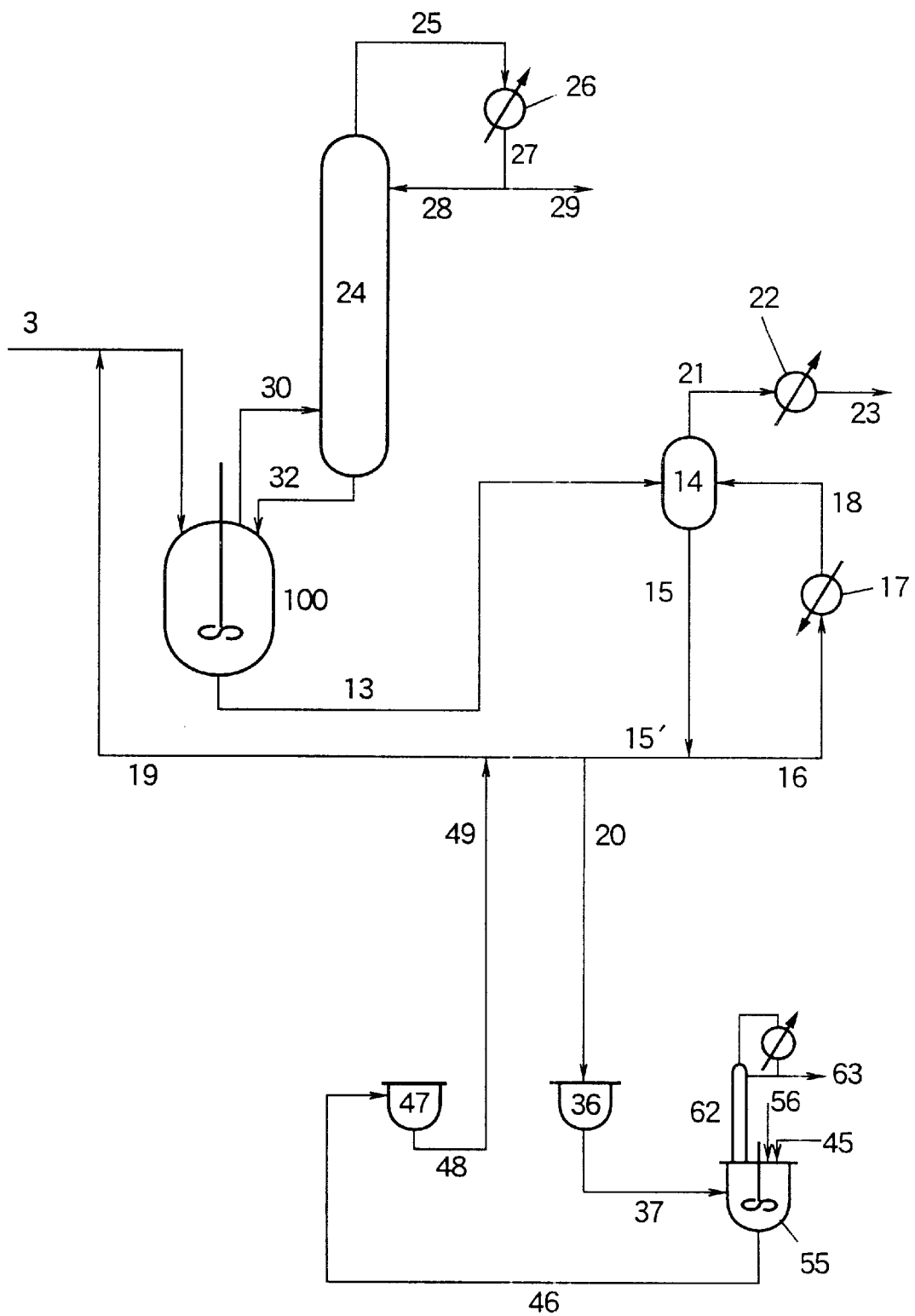
FIG. 5 is a diagram showing still a further example of systems for practicing the process of the present invention.

The production of an aromatic carbonate was conducted using the system as shown in FIG. 5, which comprises distillation column 24 having a height of 1 m and a diameter of 4 inches and containing Dixon packing (6 mmϕ), and reaction vessel 100 having a capacity of 200 liters and equipped with an agitator.

A mixture of dimethyl carbonate, PhOH and catalyst II was continuously fed in liquid form from conduit 3 into reaction vessel 100 at a rate of 20 kg/hr, thereby performing a reaction. The weight ratio of the dimethyl carbonate to the PhOH in the mixture was 50/50, and catalyst II was used in an amount such that the Sn concentration of the reaction mixture in conduit 13 became 0.4% by weight, wherein the Sn concentration can be confirmed using a sample withdrawn through a sampling nozzle (not shown) provided on conduit 13. The reaction conditions of the above reaction were such that the temperature in reaction vessel 100 was 204° C. and the pressure at the top of distillation column 24 was $7.5 \times 10^5$ Pa. Gas (containing methanol and dimethyl carbonate) formed in reaction vessel 100 was led into distillation column 24 through conduit 30. From distillation column 24, dimethyl carbonate was recycled to reaction vessel 100 through conduit 32, while the gas (containing methanol and dimethyl carbonate) distilled from the top of distillation column 24 was led through conduit 25 into condenser 26, in which the gas was condensed. A portion of the resultant condensate was recycled into distillation column 24 at a reflux ratio of 5.0 through conduits 27 and 28, and the remainder of the condensate was continuously withdrawn at a rate of 2.3 kg/hr through conduit 29. A reaction mixture [containing methyl phenyl carbonate (as a desired reaction product), the catalyst, and high boiling point substances] was continuously withdrawn from the bottom of reaction vessel 100 at a rate of 17.7 kg/hr through conduit 13 and led into evaporator 14, from which an evaporated gas containing the methyl phenyl carbonate was withdrawn and led through conduit 21 into condenser 22, in which the evaporated gas was condensed. The resultant condensate was withdrawn from condenser 22 through conduit 23 at a rate of 16.7 kg/hr. On the other hand, an evaporation-concentrated liquid containing the catalyst and the high boiling point substances was formed in evaporator 14. A portion of the concentrated liquid was led into reboiler 17 through conduits 15 and 16 and recycled into evaporator 14 through conduit 18. The remainder of the concentrated liquid in evaporator 14 was recycled into reaction vessel 100 at a rate of 1 kg/hr through conduits 15, 19 and 3. During the period of time of from 400 hours to 2,000 hours after the start of the operation, a portion of the concentrated liquid formed in evaporator 14 was continuously withdrawn through conduit 20 at a rate of 0.05 kg/hr and led into storage vessel 36 having a capacity of 10 liters. At a point in time of 1,000 hours after the start of the operation, a sample (of the concentrated liquid withdrawn from evaporator 14) was taken through a sampling nozzle (not shown) provided on conduit 15', and was analyzed to determine the composition of the concentrated liquid by the above-mentioned methods. The concentrated liquid had the following composition: Sn (which is the metal component of catalyst II): 6.7% by weight; the total concentration of high boiling point substances: 2.2% by weight; and phenyl salicylate (which is a high boiling point substance): 0.7% by weight.

At a point in time of 500 hours after the start of the operation, 2 kg of the concentrated liquid stored in storage vessel 36 was withdrawn through conduit 37 and led into reaction vessel 55 which had a capacity of 10 liters and which was equipped with distillation column 62, a jacket (not shown) for circulating a heating medium, and an agitator. 4 kg of dimethyl carbonate was introduced into reaction vessel 55 from conduit 56, and the temperature of reaction vessel 55 was elevated to and maintained at 200° C. (as measured at the jacket) while stirring. The pressure in reaction vessel 55 rose to $7.2 \times 10^5$ Pa. After continuing the stirring at 200° C. for 4 hours, the temperature of reaction vessel 55 (as measured at the jacket) was lowered to 80° C. Then, the composition of the resultant reaction mixture in reaction vessel 55 was analyzed. The analysis of the composition showed that phenyl salicylate was not present at all and, instead, methyl salicylate was present (wherein the methyl salicylate is presumed to have been formed by the reaction of phenyl salicylate with dimethyl carbonate).

Thereafter, distillation was started by elevating the temperature of reaction vessel 55 to 200° C. (as measured at the jacket) under atmospheric pressure, and a distillate begun to come out through conduit 63. The distillation was continued while gradually lowering the pressure in reaction vessel 55 from atmospheric pressure to reduced pressure. When the amount of the distillate obtained through conduit 63 became 4.32 kg, the distillation was terminated. Subsequently, the pressure in reaction vessel 55 was adjusted to atmospheric pressure by introducing nitrogen gas, and the weight of the reaction mixture in reaction vessel 55 was adjusted to 2 kg by introducing PhOH. The reaction mixture, which remained in reaction vessel 55 after performing the above distillation, was withdrawn from reaction vessel 55 and transferred through conduit 46 and introduced into storage vessel 47 having a capacity of 10 liters. The composition of the reaction mixture was analyzed. The analysis of the composition showed that phenyl salicylate was not present at all and the total concentration of high boiling point substances had decreased to 0.8% by weight.

Thereafter, every 40 hours after the point in time of 500 hours from the start of the operation (i.e., the point in time at which 2 kg of the concentrated liquid was withdrawn from storage vessel 36 and led into reaction vessel 55 as mentioned above), a sequence of the above operations using storage vessel 36 (from which 2 kg of the concentrated liquid was withdrawn), reaction vessel 55 and storage vessel 47 (into which the remaining reaction mixture obtained in reaction vessel 55 was introduced) was repeated in the same manner as described above.

On the other hand, from a point in time of 600 hours after the start of the operation, the reaction mixture stored in storage vessel 47 was continuously withdrawn at a rate of 0.05 kg/hr through conduit 48 and recycled into the system for the transesterification through conduit 49.

The condensate withdrawal rate from condenser 22 through conduit 23 during the period of time of from 400 hours to 600 hours after the start of the operation was 16.65 kg/hr, and the condensate withdrawal rate from condenser 22 through conduit 23 during the period of time of from 600 hours to 2,000 hours after the start of the operation was 16.7 kg/hr. During the period of time of from 400 hours to 600 hours after the start of the operation, catalyst II was added to reaction vessel 100 through conduit 3 at such a feeding rate as to compensate for the catalyst withdrawal rate at which the catalyst was withdrawn through conduit 20, i.e., catalyst II was added through conduit 3 at a feeding rate such that the above-mentioned Sn concentration of 0.4% by weight in conduit 13 was able to be maintained.

The operation was carried out for 2,000 hours. From the period of time of from 600 hours after the start of the operation, i.e., from the point in time at which the recycling of the catalyst into the system for the transesterification through conduit 49 was started, there was no need for introducing a fresh catalyst into the system for the transesterification. In addition, since the catalyst-containing liquid containing both the catalyst and high boiling point substances was withdrawn from the system for the transesterification and subjected to the above-described treatments according to the present invention, a waste liquid containing a spent catalyst did not occur at all.

From the evaporation-concentrated liquid which was formed in evaporator 14 and which contained the catalyst and high boiling point substances, samples were taken through the above-mentioned sampling nozzle provided on conduit 15', wherein the samples were, respectively, withdrawn at points in time of 1,000 hours, 1,500 hours and 2,000 hours after the start of the operation. The determination of the total concentration of the high boiling point substances in each sample was conducted by the above-mentioned method. With respect to these samples withdrawn at points in time of 1,000 hours, 1,500 hours and 2,000 hours after the start of the operation, the total concentrations of the high boiling point substances were 2.2% by weight, 2.2% by weight and 2.2% by weight, respectively.

During the 2,000 hour operation time, the operation could be stably conducted (for example, both the flow and the composition in each conduit were stable) without suffering disadvantageous phenomena, such as the deposition of the catalyst from a catalyst-containing liquid and the adherence of the deposited catalyst to the inside surfaces associated with the equipment employed for the operation. During the operation, samples of the reaction mixture withdrawn from the bottom of reaction vessel 100 were taken through the above-mentioned sampling nozzle provided on conduit 13, and the samples were analyzed. With respect to the reaction mixture which was taken from conduit 13 at a point in time of 2,000 hours after the start of the operation, the composition of the reaction mixture was as follows: PhOH: 51% by weight; methyl phenyl carbonate (MPC): 6% by weight; diphenyl carbonate (DPC): 0.4% by weight; anisole (ANS): 0.6% by weight; and Sn: 0.4% by weight. The purity of the aromatic carbonate (which was a mixture of MPC and DPC) in the condensate withdrawn from condenser 22 through conduit 23 was 99.99% or more, and no high boiling point substance was detected in the condensate. After the operation was terminated, the inside surfaces associated with the equipment employed for the operation were examined. No adherence of the catalyst to any of the inner walls of reaction vessel 100, evaporator 14, reboiler 17, conduits and the like was observed.

EXAMPLE 6

Preparation of Catalyst

A mixture of 40 kg of PhOH and 8 kg of titanium tetrachloride was heated to and maintained at 50° C. for 10 hours under a flow of nitrogen gas, thereby performing a reaction. After that period of time, hydrogen chloride formed in the resultant reaction mixture was distilled off together with unreacted PhOH. Then, most of the remaining PhOH was distilled off from the reaction mixture under reduced pressure, and the resultant mixture was allowed to cool in a nitrogen atmosphere, to thereby obtain catalyst III.

Production of Aromatic Carbonate

Substantially the same procedure as in Example 5 was repeated, except that catalyst III was used in an amount such that the Ti concentration of the reaction mixture in conduit 13 became 0.2% by weight. The operation was continued for 2,000 hours. During the 2,000 hour operation time, the operation could be stably conducted (for example, both the flow and the composition in each conduit were stable) without suffering disadvantageous phenomena, such as the deposition of the catalyst from a catalyst-containing liquid and the adherence of the deposited catalyst to the inside surfaces associated with the equipment employed for the operation. From the evaporation-concentrated liquid which was formed in evaporator 14 and which contained the catalyst and high boiling point substances, samples were taken through the sampling nozzle provided on conduit 15', wherein the samples were, respectively, withdrawn at points in time of 1,000 hours, 1,500 hours and 2,000 hours after the start of the operation. The determination of the total concentration of the high boiling point substances in each sample was conducted by the above-mentioned method. With respect to these samples withdrawn at points in time of 1,000 hours, 1,500 hours and 2,000 hours after the start of the operation, the total concentrations of the high boiling point substances were 2.8% by weight, 2.9% by weight and 2.9% by weight, respectively. During the operation, samples of the reaction mixture withdrawn from the bottom of reaction vessel 100 were taken through the sampling nozzle provided on conduit 13, and the samples were analyzed. With respect to the reaction mixture which was taken from conduit 13 at a point in time of 2,000 hours after the start of the operation, the composition of the reaction mixture was as follows: PhOH: 51% by weight; methyl phenyl carbonate (MPC): 6% by weight; diphenyl carbonate (DPC): 0.4% by weight; anisole (ANS): 0.4% by weight; and Ti: 0.2% by weight. The purity of the aromatic carbonate (which was a mixture of MPC and DPC) in the condensate withdrawn from condenser 22 through conduit 23 was 99.99% or more, and no high boiling point substance was detected in the condensate. After the operation was terminated, the inside surfaces associated with the equipment employed for the operation were examined. No adherence of the catalyst to any of the inner walls of reaction vessel 100, evaporator 14, reboiler 17, conduits and the like was observed.

EXAMPLE 7

235 g of diphenyl carbonate obtained in Example 3 and 228 g of bisphenol A were placed in a vacuum reaction apparatus equipped with an agitator, and the resultant mixture was heated to 180° C. while stirring and gradually evacuating the reaction apparatus with nitrogen gas. Then, the temperature of the mixture was slowly elevated from 180 to 220° C. while stirring and evacuating the reaction apparatus with nitrogen gas. Subsequently, the reaction apparatus was sealed, and a polymerization was effected at 8,000 Pa for 30 minutes while stirring at 100 rpm, and then, at 4,000 Pa for 90 minutes while stirring at 100 rpm. Thereafter, the temperature of the reaction apparatus was elevated to 270° C., and a polymerization was effected at 70 Pa for one hour, thereby obtaining an aromatic polycarbonate. The obtained aromatic polycarbonate was colorless and transparent, and had a number average molecular weight of 10,200.

Comparative Example 5

Substantially the same procedure as in Example 7 was repeated, except that the diphenyl carbonate obtained in Comparative Example 4 was used (instead of the diphenyl carbonate obtained in Example 3). The obtained aromatic polycarbonate had suffered yellowing and had a number average molecular weight of 8,800.

INDUSTRIAL APPLICABILITY

By the process of the present invention, an aromatic carbonate having high purity can be produced stably for a prolonged period of time. Therefore, the process of the present invention can be advantageously employed in a commercial-scale mass production of an aromatic carbonate. An aromatic carbonate produced by the process of the present invention is used as a raw material for producing aromatic polycarbonates, use of which as engineering plastics has been increasing in recent years.

What is claimed is:

1. In a process for producing aromatic carbonates, which comprises the steps of:
   (1) transesterifying a starting material selected from the group consisting of a dialkyl carbonate represented by the formula (1)

an alkyl aryl carbonate represented by the formula (2)

and a mixture thereof with a reactant selected from the group consisting of an aromatic monohydroxy compound represented by the formula (3)

an alkyl aryl carbonate represented by the formula (4)

and a mixture thereof,
   wherein each of $R^1$, $R^2$ and $R^3$ independently represents an alkyl group having 1 to 10 carbon atoms, an alicyclic group having 3 to 10 carbon atoms or an aralkyl group having 6 to 10 carbon atoms, and each of $Ar^1$, $Ar^2$ and $Ar^3$ independently represents an aromatic group having 5 to 30 carbon atoms,
in the presence of a metal-containing catalyst which is soluble in a reaction system comprising said starting material and said reactant and which is present in a state dissolved in said reaction system, to thereby obtain a high boiling point reaction mixture comprising said metal-containing catalyst and at least one aromatic carbonate which is produced by the transesterification and which corresponds to the starting material and the reactant and is selected from the group consisting of an alkyl aryl carbonate represented by the formula (5)

and a diaryl carbonate represented by the formula (6)

wherein R and Ar are, respectively, selected from the group consisting of $R^1$, $R^2$ and $R^3$ and selected from the group consisting of $Ar^1$, $Ar^2$ and $Ar^3$ in correspondence to the starting material and the reactant, while withdrawing a low boiling point reaction mixture which contains a low boiling point by-product comprising an aliphatic alcohol, a dialkyl carbonate or a mixture thereof corresponding to the starting material and the reactant and represented by at least one formula selected from the group consisting of ROH and

wherein R is as defined above,
(2) separating said high boiling point reaction mixture into a product fraction comprising said produced aromatic carbonate and a liquid catalyst fraction comprising said metal-containing catalyst, and
(3) recycling said liquid catalyst fraction to said reaction system while withdrawing said product fraction,
the improvement which comprises the steps of:
(1') taking out at least one type of catalyst-containing liquid which is selected from the group consisting of:
a portion of said high boiling point reaction mixture before the separation of said high boiling point reaction mixture into said product fraction and said liquid catalyst fraction, and
a portion of the separated liquid catalyst fraction,
each portion containing (A) at least one high boiling point substance having a boiling point higher than the boiling point of said produced aromatic carbonate and containing (B) said metal-containing catalyst,
(2') adding to the taken-out catalyst-containing liquid a functional substance (C) capable of reacting with at least one component selected from the group consisting of said component (A) and said component (B), to thereby obtain a reaction mixture containing an (A)/(C) reaction product and a (B)/(C) reaction product,
wherein:
when said functional substance (C) is capable of reacting with said component (A), said (A)/(C) reaction product is a product formed by the reaction between said component (A) and said component (C),
when said functional substance (C) is not capable of reacting with said component (A), said (A)/(C) reaction product is unreacted component (A) present in said reaction mixture,
when said functional substance (C) is capable of reacting with said component (B), said (B)/(C) reaction product is a product formed by the reaction between said component (B) and said component (C), and
when said functional substance (C) is not capable of reacting with said component (B), said (B)/(C) reaction product is unreacted component (B) present in said reaction mixture, and
(3') recycling said (B)/(C) reaction product to said reaction system directly or indirectly, while withdrawing said (A)/(C) reaction product.
2. The process according to claim 1, wherein said portion of the high boiling point reaction mixture is from 0.01 to 10% by weight, based on the weight of said high boiling point reaction mixture, and wherein said portion of the separated liquid catalyst fraction is from 0.01 to 40% by weight, based on the weight of said separated liquid catalyst fraction.

3. The process according to claim 1 or 2, wherein said high boiling point substance (A) originates from at least one compound selected from the group consisting of said starting material, said reactant, impurities contained in said starting material and said reactant, and by-products of the transesterification reaction.

4. The process according to claim 1 or 2, wherein said high boiling point substance (A) is at least one substance selected from the group consisting of an aromatic hydroxy compound (7), a compound (8) derived from said compound (7), an aromatic carboxy compound (9), a compound (10) derived from said compound (9), and xanthone,
wherein:
compound (7) is represented by the formula (7):

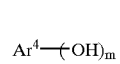

(7)

wherein $Ar^4$ represents an aromatic group having a valence of m, m represents an integer of 2 or more, and each —OH group is independently bonded to an arbitrary ring-carbon position of the $Ar^4$ group,
compound (8) contains a residue represented by the formula (8):

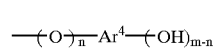

(8)

wherein $Ar^4$ and m are as defined for formula (7), n represents an integer of from 1 to m, and each of the -OH group and the —O— group is independently bonded to an arbitrary ring-carbon position of the $Ar^4$ group, compound (9) is represented by the formula (9):

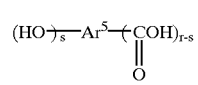

(9)

wherein $Ar^5$ represents an aromatic group having a valence of r, r represents an integer of 1 or more, s represents an integer of from O to (r–1), and each of the —OH group and the —COOH group is independently bonded to an arbitrary ring-carbon position of the $Ar^5$ group, and
compound (10) contains a residue represented by the formula (10):

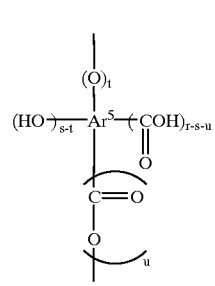

(10)

wherein $Ar^5$, r and s are as defined for formula (9), t is an integer of from O to s, u is an integer of from O to (r—s), with the proviso that t and u are not simultaneously O, and each of the —OH group, the —COOH group, the —O— group and the —(COO)— group is independently bonded to an arbitrary ring-carbon position of the $Ar^5$ group.

5. The process according to claim 1 or 2, wherein said functional substance (C) is an oxidizing agent, so that said (A)/(C) reaction product is a low boiling point oxidation product and said (B)/(C) reaction product is a metal oxide.

6. The process according to claim 1 or 2, wherein said functional substance (C) is a precipitant, so that said (B)/(C) reaction product is a metal-containing substance which precipitates.

7. The process according to claim 6, wherein said metal-containing substance is a metal compound selected from the group consisting of a metal carbonate, a metal hydroxide, a metal oxide, a metal sulfide and a metal sulfate.

8. The process according to claim 1 or 2, wherein said functional substance (C) is a reactive solvent, so that said (A)/(C) reaction product is a low boiling point product obtained by the solvolysis of component (A).

9. The process according to claim 8, wherein said reactive solvent is water, so that said (A)/(C) reaction product is an aromatic monohydroxy compound obtained by the hydrolysis of component (A).

10. The process according to claim 1 or 2, wherein said steps (1), (2) and (3) are continuously performed, thereby continuously producing an aromatic carbonate.

11. The process according to claim 10, wherein said starting material and said reactant are continuously fed to a continuous multi-stage distillation column to effect a transesterification reaction therebetween in at least one phase selected from the group consisting of a liquid phase and a gas-liquid phase in the presence of said metal-containing catalyst in said distillation column, while continuously withdrawing a high boiling point reaction mixture containing the produced aromatic carbonate in a liquid form from a lower portion of the distillation column and continuously withdrawing a low boiling point reaction mixture containing the low boiling point by-product in a gaseous form from an upper portion of the distillation column by distillation.

12. A process for producing aromatic polycarbonates, which comprises subjecting to transesterification no polymerization an aromatic carbonate produced by the process according to any one of claims 1 to 11 and an aromatic dihydroxy compound.

* * * * *